United States Patent
Eggers et al.

(10) Patent No.: US 7,613,523 B2
(45) Date of Patent: Nov. 3, 2009

(54) AESTHETIC THERMAL SCULPTING OF SKIN

(75) Inventors: Philip E. Eggers, Dublin, OH (US); Annette Campbell-White, Oakland, CA (US); Bryant A. Toth, San Francisco, CA (US)

(73) Assignee: Apsara Medical Corporation, San Mateo, CA (US)

( * ) Notice: Subject to any disclaimer, the term of this patent is extended or adjusted under 35 U.S.C. 154(b) by 849 days.

(21) Appl. No.: 11/298,420

(22) Filed: Dec. 9, 2005

(65) Prior Publication Data

US 2006/0095103 A1 May 4, 2006

Related U.S. Application Data

(63) Continuation-in-part of application No. 10/733,970, filed on Dec. 11, 2003, now Pat. No. 7,048,756.

(60) Provisional application No. 60/677,955, filed on May 5, 2005.

(51) Int. Cl.
*A61F 2/00* (2006.01)
(52) U.S. Cl. .................. 607/103; 128/898; 607/113
(58) Field of Classification Search ........... 607/96–103, 607/113
See application file for complete search history.

(56) References Cited

U.S. PATENT DOCUMENTS

| | | | |
|---|---|---|---|
| 4,485,810 A | 12/1984 | Beard | |
| 4,979,948 A | 12/1990 | Geddes et al. | |
| 5,419,769 A | 5/1995 | Devlin et al. | |
| 5,569,242 A | 10/1996 | Lax et al. | |
| 5,755,753 A | 5/1998 | Knowlton | |
| 5,957,920 A * | 9/1999 | Baker | 606/33 |
| 6,001,090 A | 12/1999 | Lenhart | |
| 6,041,260 A | 3/2000 | Stern et al. | |
| 6,203,540 B1 | 3/2001 | Weber | |
| 6,241,753 B1 | 6/2001 | Knowlton | |
| 6,277,116 B1 | 8/2001 | Utely et al. | |
| 6,306,119 B1 | 10/2001 | Weber et al. | |
| 6,311,090 B1 | 10/2001 | Knowlton | |
| 6,375,672 B1 * | 4/2002 | Aksan et al. | 607/96 |
| 6,381,498 B1 | 4/2002 | Knowlton | |
| 6,391,023 B1 | 5/2002 | Weber et al. | |
| 6,405,090 B1 | 6/2002 | Knowlton | |
| 6,432,101 B1 | 8/2002 | Weber et al. | |
| 6,440,121 B1 | 8/2002 | Weber et al. | |
| 6,589,067 B1 | 7/2003 | Kolton et al. | |

(Continued)

OTHER PUBLICATIONS

Lawrence, et al., "History of Dermabrasion" Dermaton Surg 2000; 26:95-101.

(Continued)

*Primary Examiner*—Roy D Gibson
(74) *Attorney, Agent, or Firm*—Mueller Smith & Okuley, LLC

(57) ABSTRACT

Method, system and apparatus for carrying out a controlled heating of dermis to achieve a percentage of linear collagen shrinkage. Implants are employed which preferably are configured as a thermal barrier defining support of an outwardly disposed support surface which carries one or more heater segments. Located along heating channels at the interface between dermis and next adjacent subcutaneous tissue, the structure protects the latter from thermally induced damage while directing heat energy into the former.

50 Claims, 46 Drawing Sheets

U.S. PATENT DOCUMENTS

| | | | |
|---|---|---|---|
| 6,663,618 | B2 | 12/2003 | Weber et al. |
| 6,668,197 | B1 * | 12/2003 | Habib et al. ............ 607/101 |
| 6,699,237 | B2 | 3/2004 | Weber et al. |
| 6,726,693 | B2 | 4/2004 | Weber et al. |
| 6,764,493 | B1 | 7/2004 | Weber et al. |
| 6,786,904 | B2 | 9/2004 | Doscher et al. |
| 6,920,883 | B2 | 7/2005 | Bessette et al. |
| 2004/0127895 | A1 | 7/2004 | Flock et al. |
| 2005/0021088 | A1 | 1/2005 | Schuler et al. |
| 2005/0049658 | A1 | 3/2005 | Connors et al. |
| 2005/0059940 | A1 | 3/2005 | Weber et al. |
| 2005/0171581 | A1 | 8/2005 | Connors et al. |

OTHER PUBLICATIONS

Moy, et al., "Comparison of the Effect of Various Chemical Peeling Agents in a Mini-Pig Model" Dermatol Surg 1996; 22:429-432.

Manstein, et al., "Fractional Photothermolysis: A New Concept for Cutaneous Remodeling Using Microscopic Patterns of Thermal Injury"; Lasers in Surgery and Medicine 34:426-4.

Rasmussen, et al., "Isotonic and Isometric Thermal Contraction of Human Dermis I. Technic and Controlled Study", J. Invest Derm. 1964; 43:333-9.

Fitzpatrick, et al., "Collagen Tightening Induced by Carbon Dioxide Lasr Versus Erbium: YAG Laser" Lasers in Surgery and Medicine 27: 395-403 (2000).

Fitzpatrick, et al., "multicenter Study of Noninvasive Radiofrequency for Periorbital Tissue Tightening", Lasers in Surgery in Medicine 33:232-242 (2003).

Abraham, et al., "Current Concepts in Nonablative Radiofrequency Rejuvenation of the Lower Face and Neck" Facial Plastic Surgery, vol. 21 No. 1 (2005).

Lycka, et al., The Emerging Technique of the antiptosis Subdermal Suspension Thread:, Dermatol Surg; 30:41-44 (2004).

Wall, et al., "Thermal Modification of Collagen" Journal of Shoulder and Elbow Surgery; 8:339-344 (1999).

Matsuki, et al., "Temperature-sensitive amorphous magnetic flakes for intratissue hyperthermia" Mat'ls Sci and Eng. A181/A182 (1994) 1366-1368.

Brown, et al., "Observations On The Shrink Temperature Of Collagen And Its Variations With Age And Disease", Ann. rheum, Dis. (1958) 17, 196.

Pankhurst, "'Incipient Shrinkage' of Collagen and Gelatin" Nature, vol. 159, 538.

Sulamanidze, et al., "Removal of Facial Soft Tissue Ptosis With Special Threads" Dermaton Surg; 28:367-371 (2002).

EI-Domyati, "Trichloroacetic Acid Peeling Versus Dermabrasion: A Histometric, Immunohistochemical, and Ultrastructural Comparison", Dermaton. Surg 2004;30:179-188.

* cited by examiner

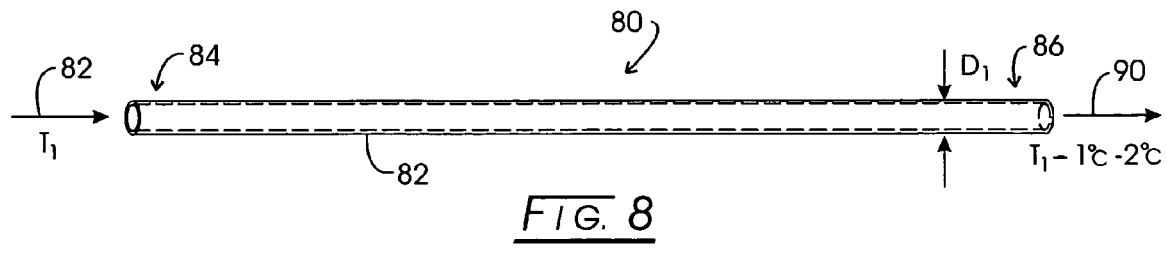
FIG. 8
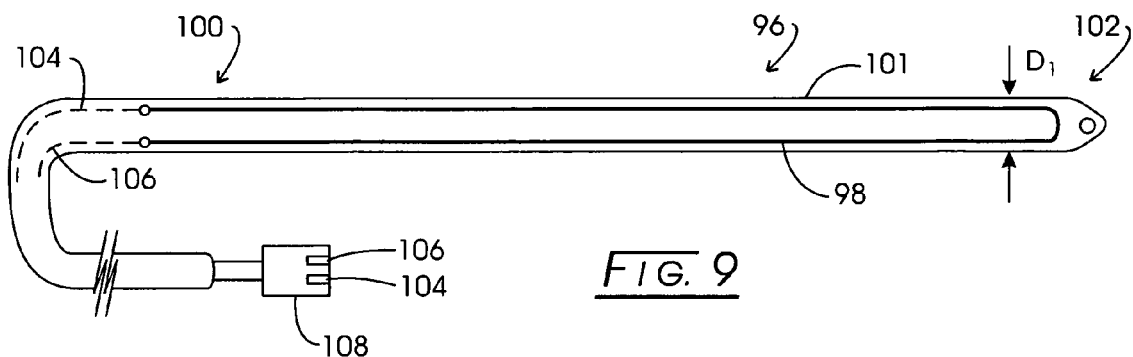
FIG. 9
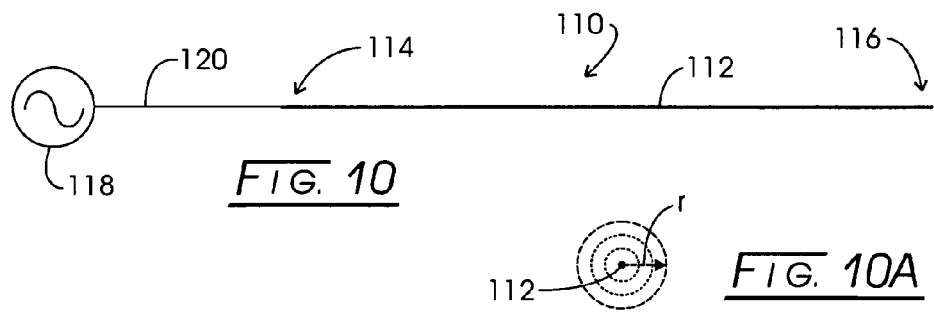
FIG. 10
FIG. 10A
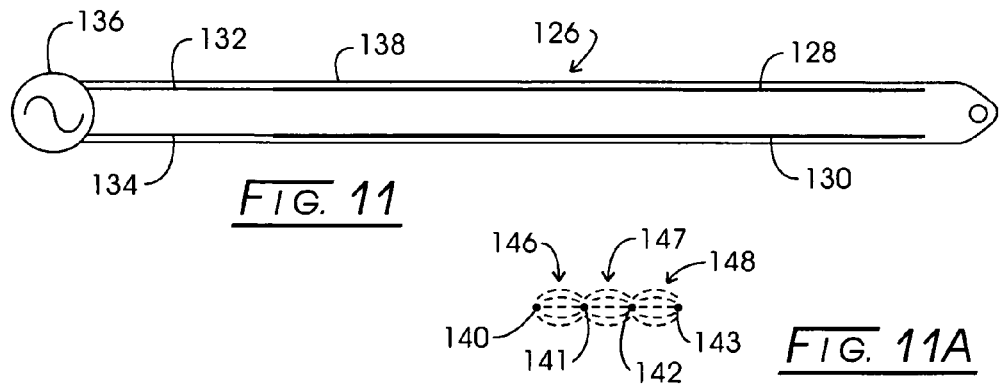
FIG. 11
FIG. 11A

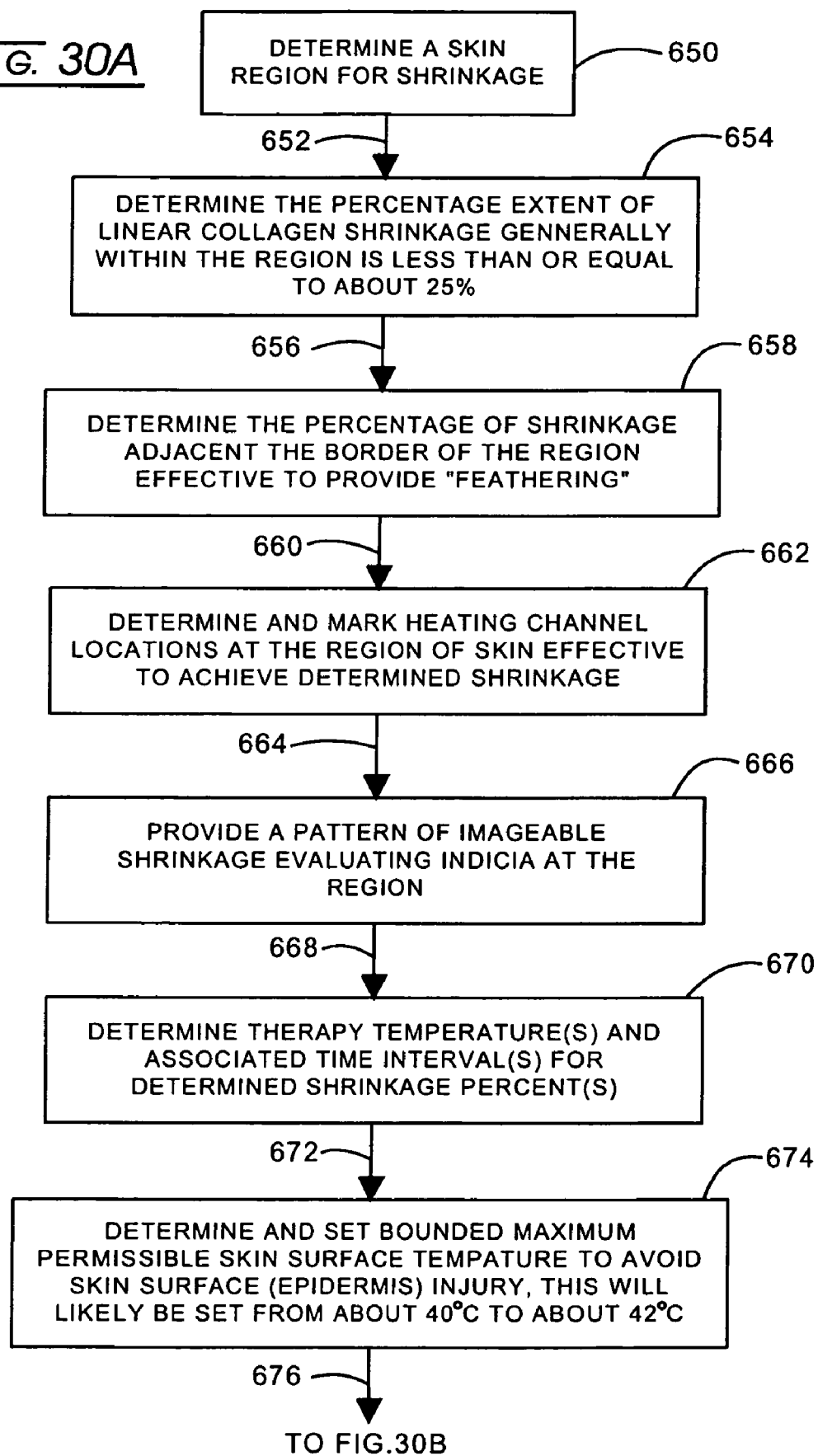

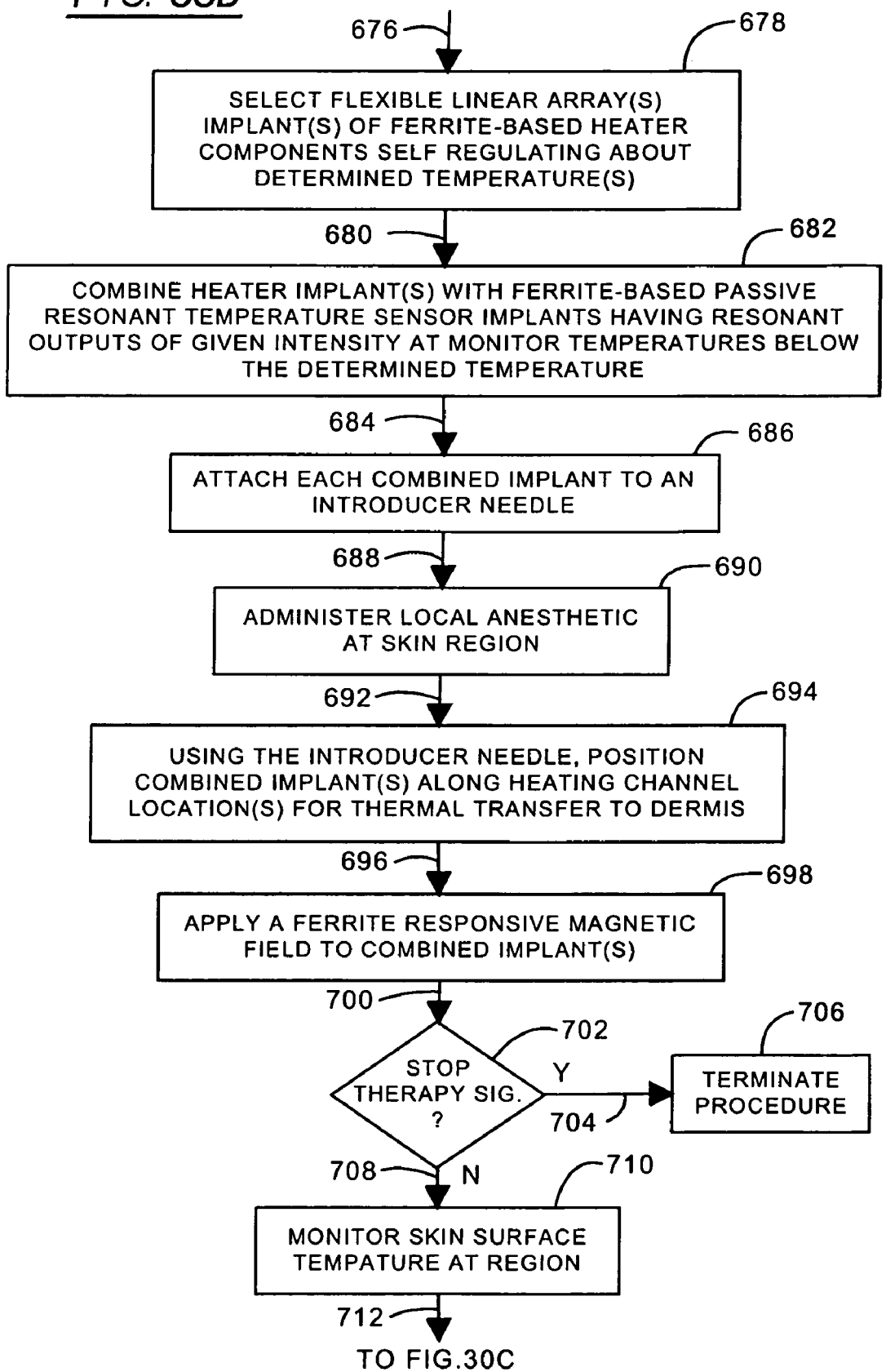

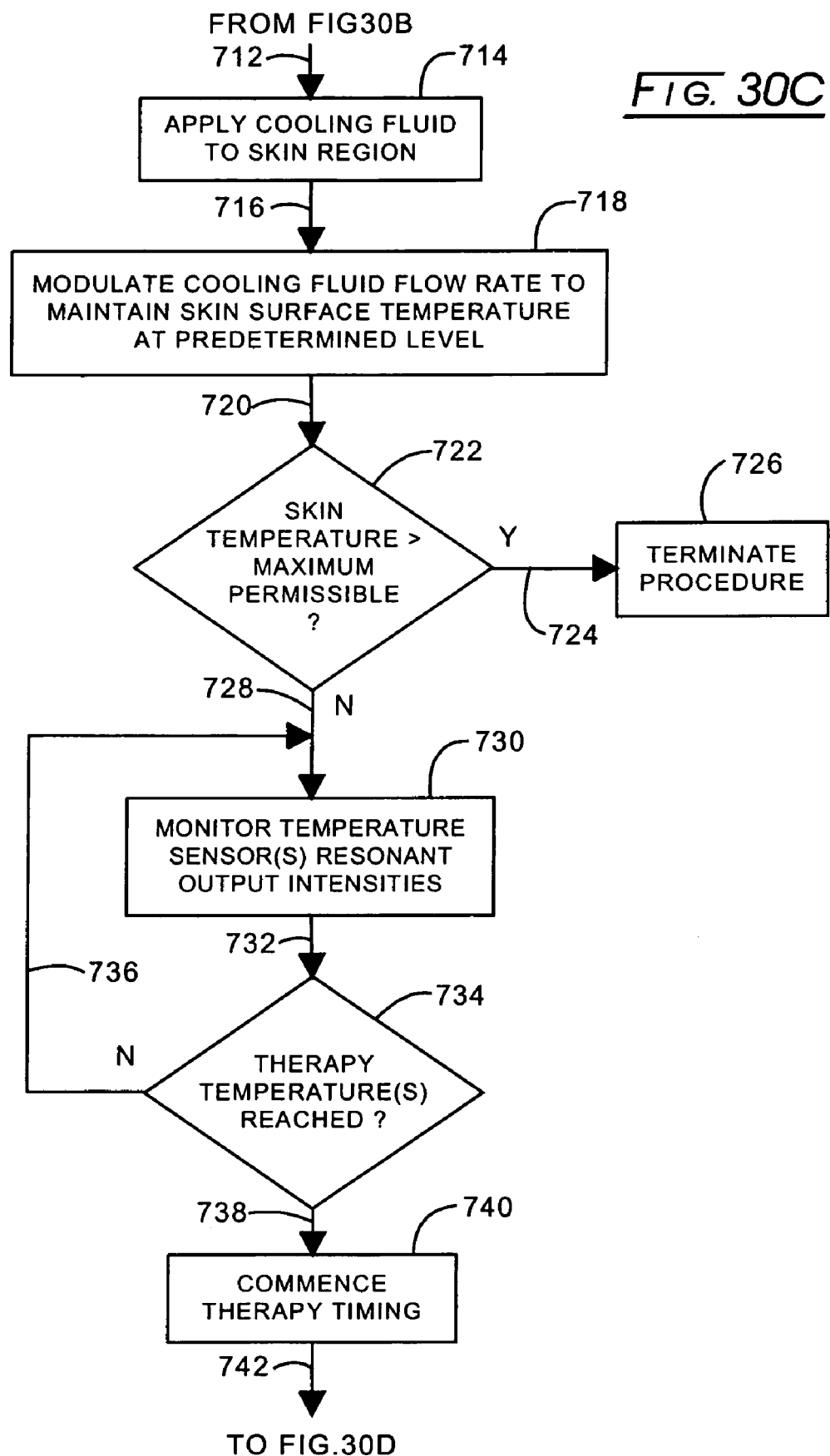

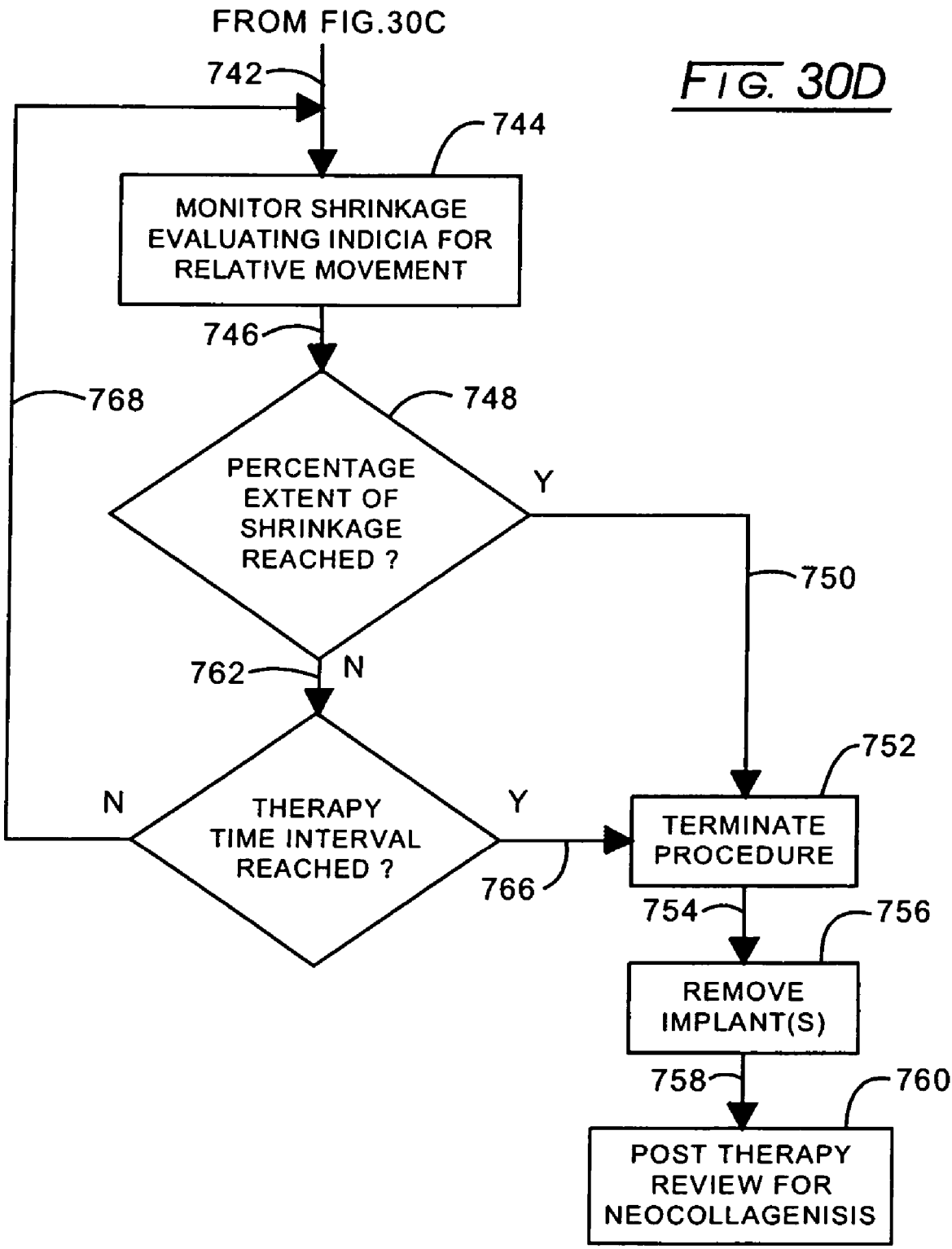

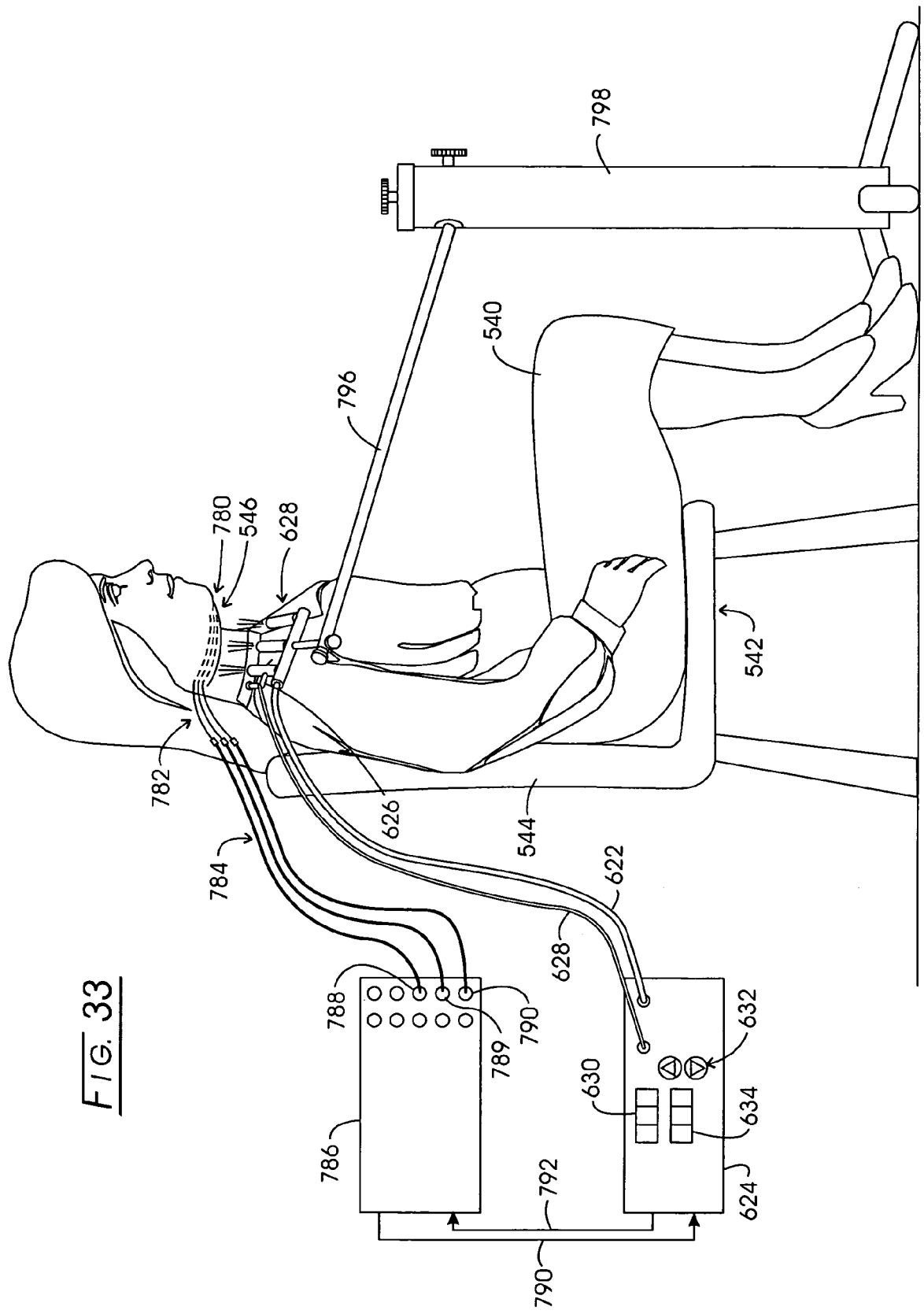

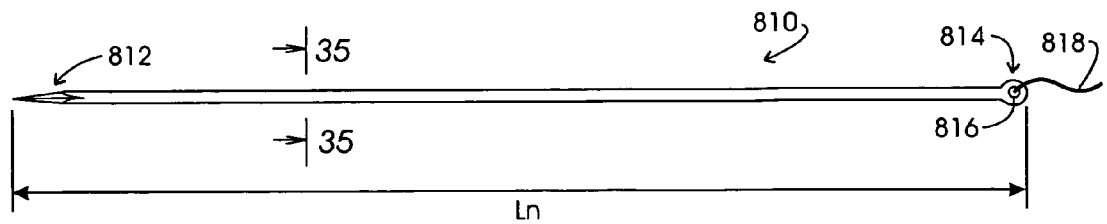
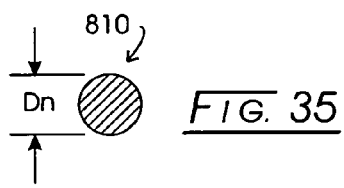
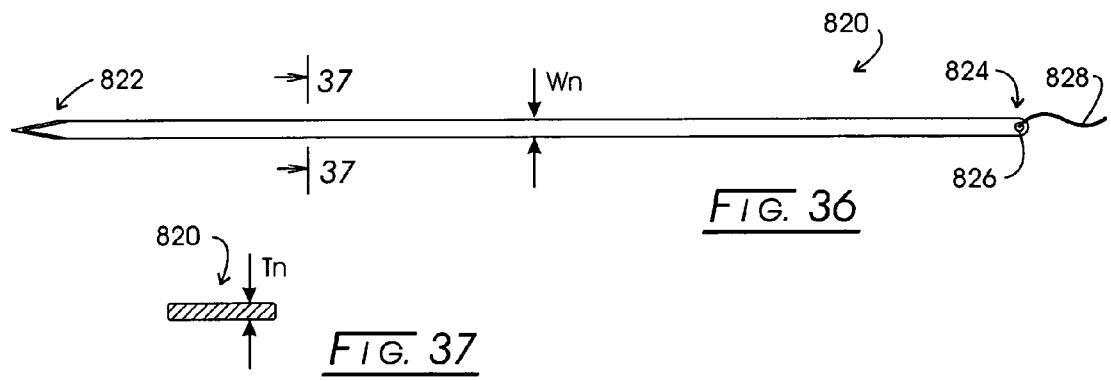
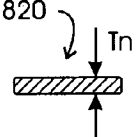
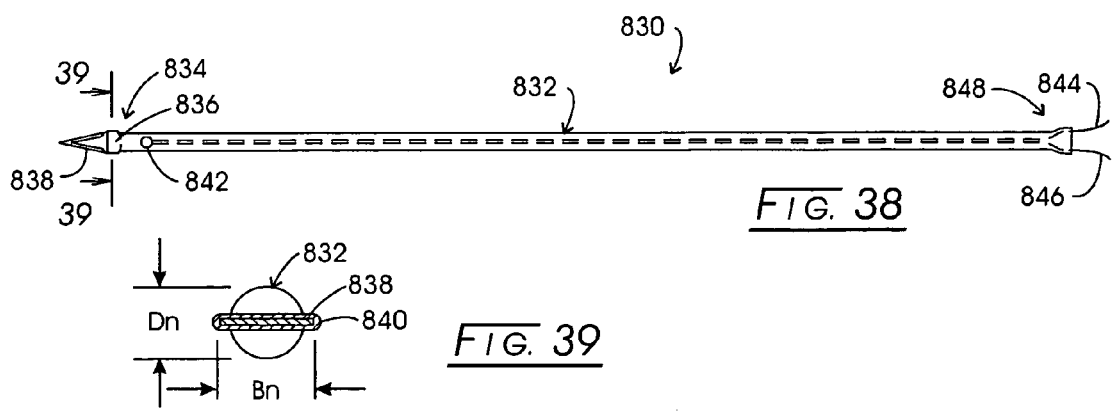
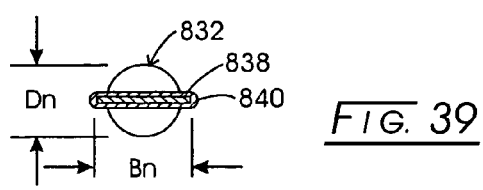

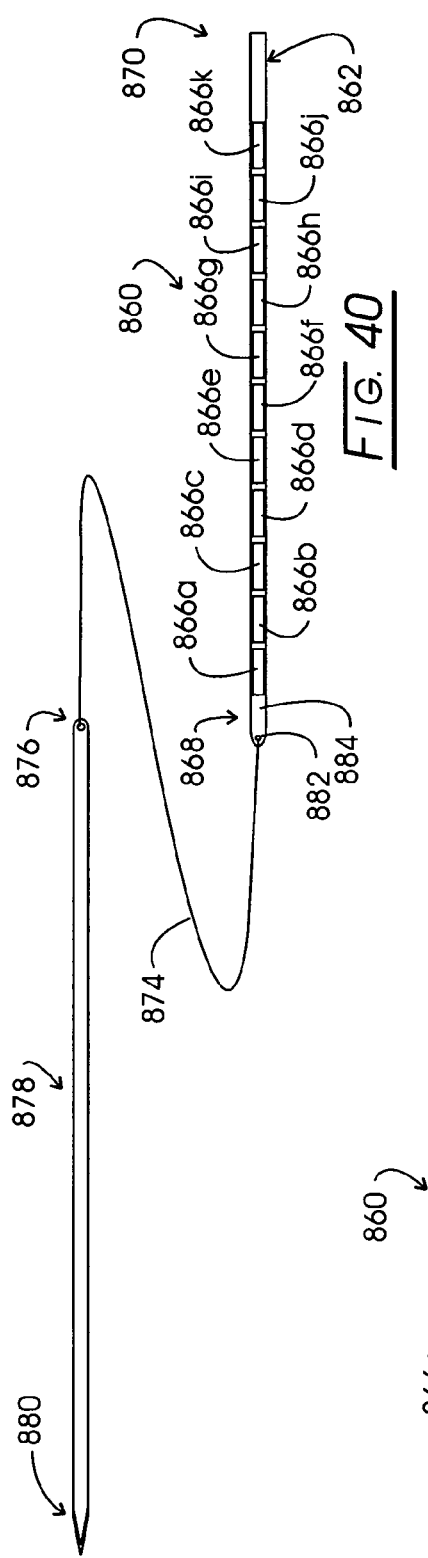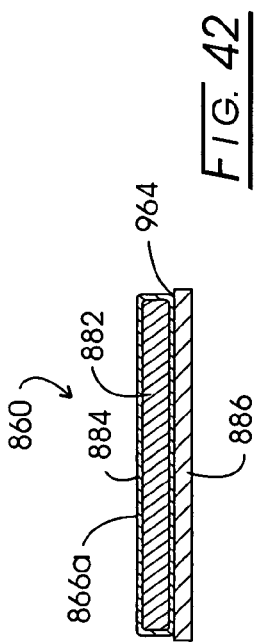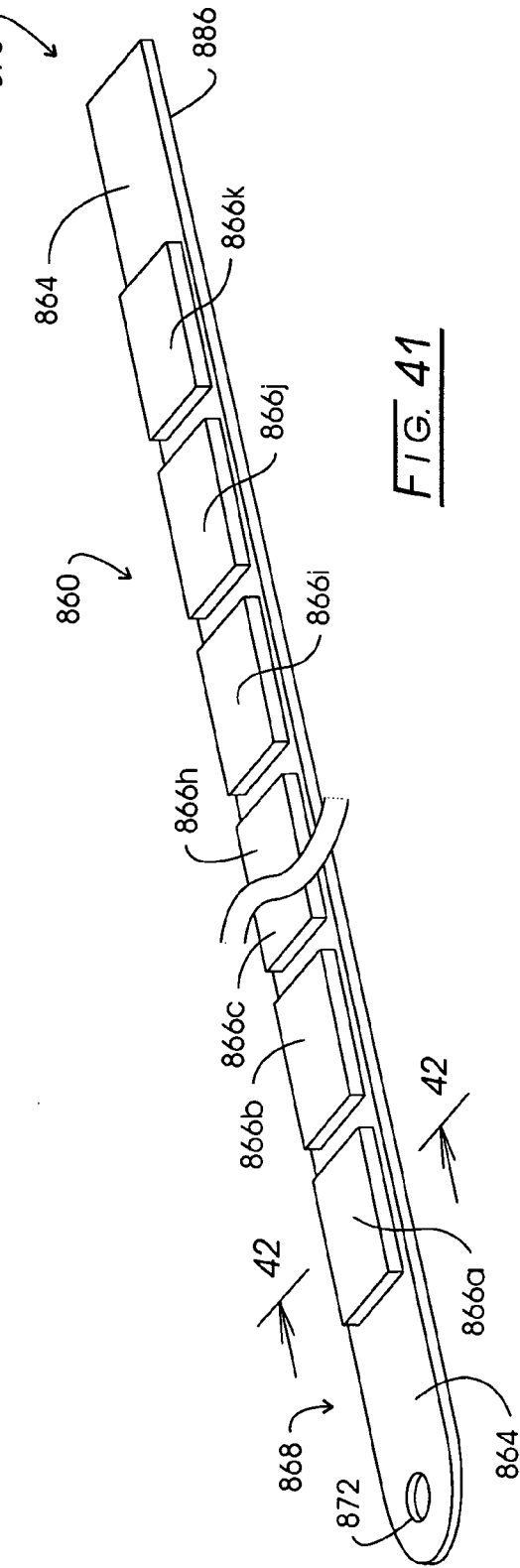

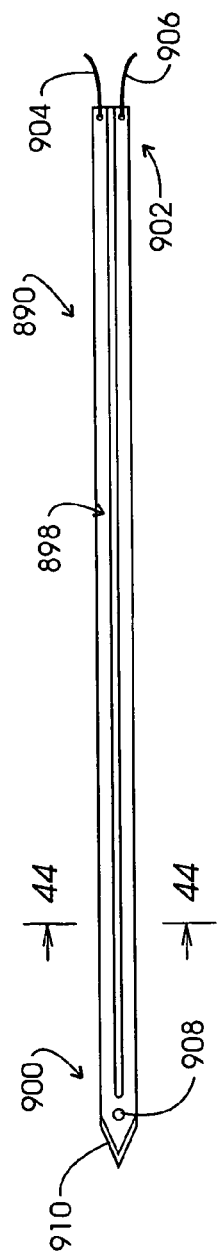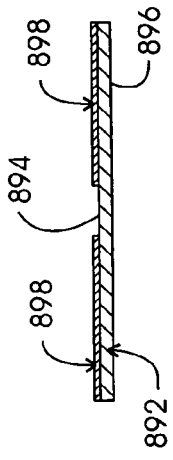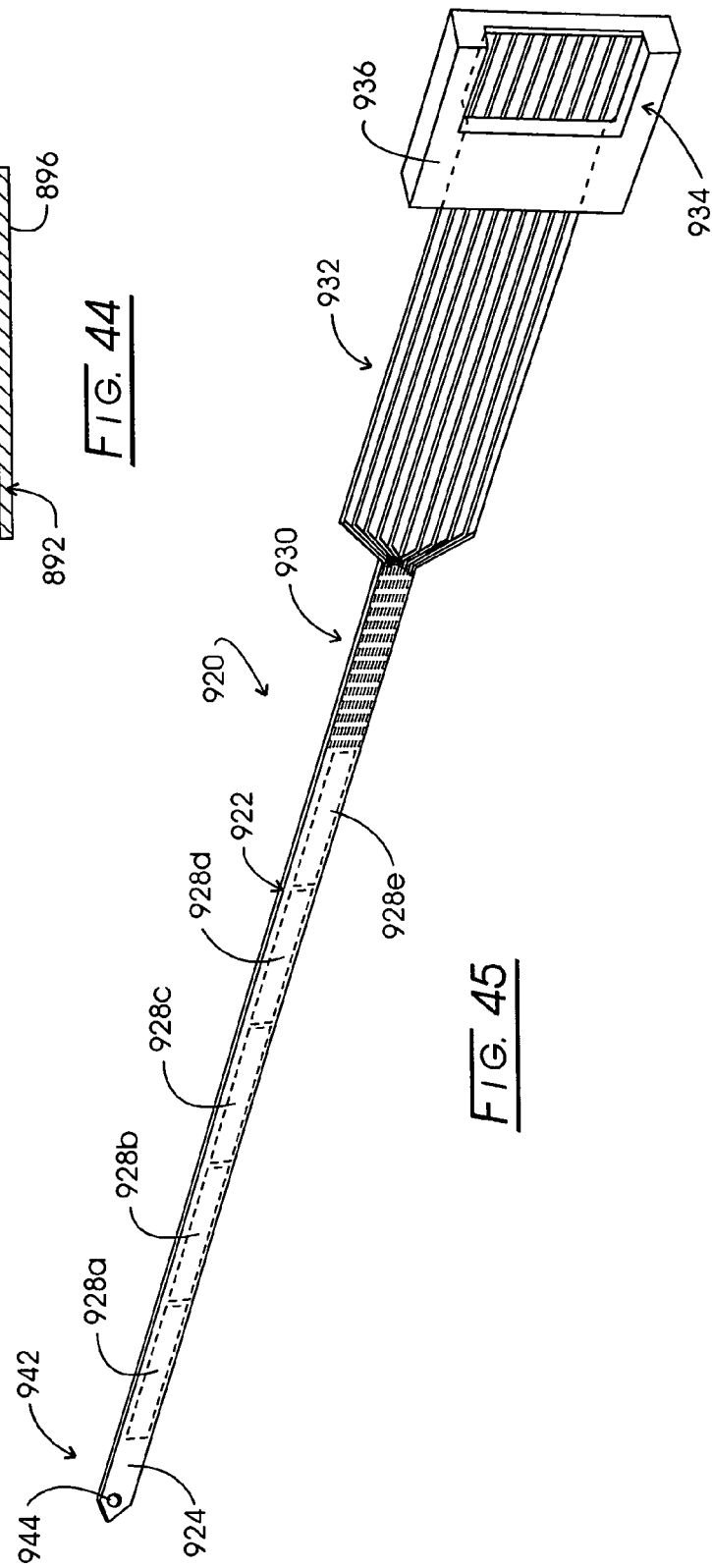

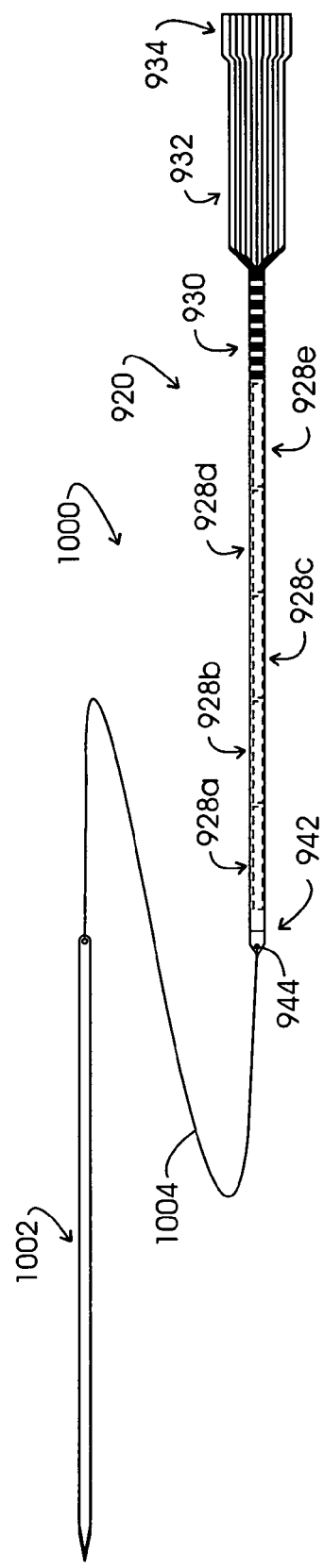
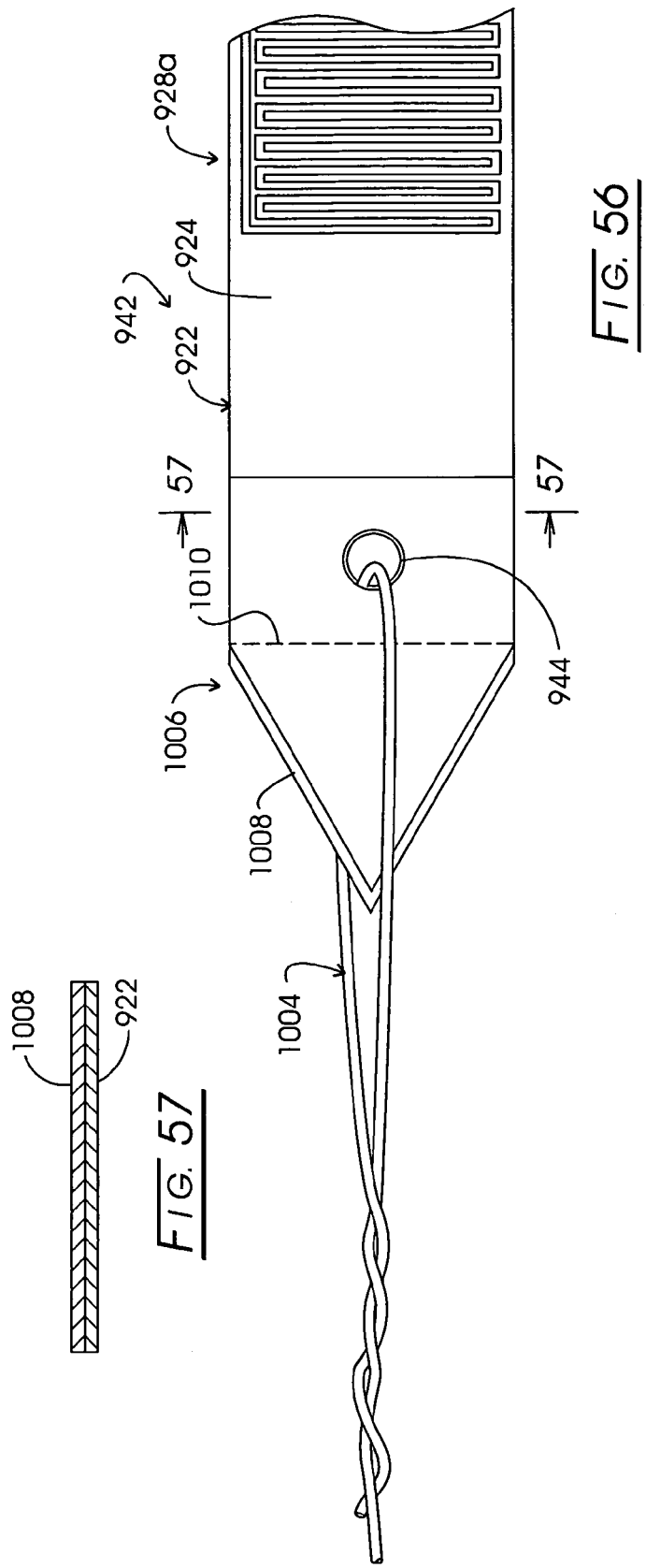
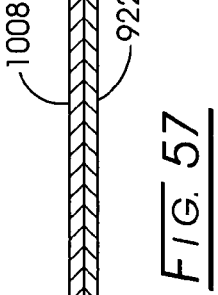
FIG. 55
FIG. 56
FIG. 57

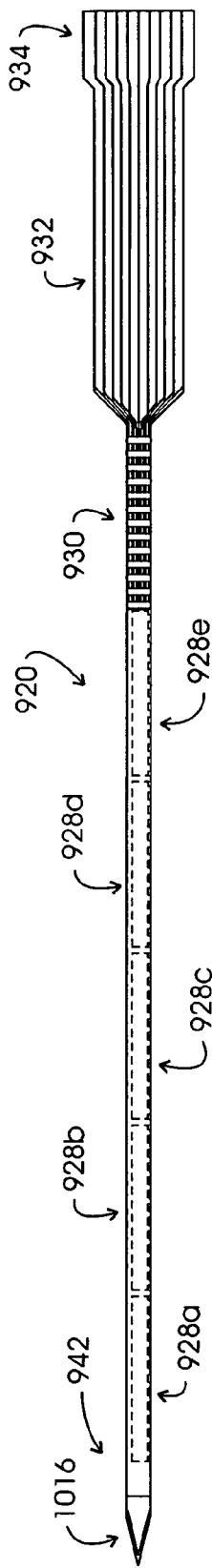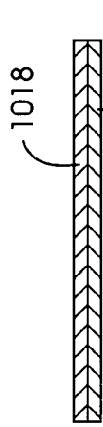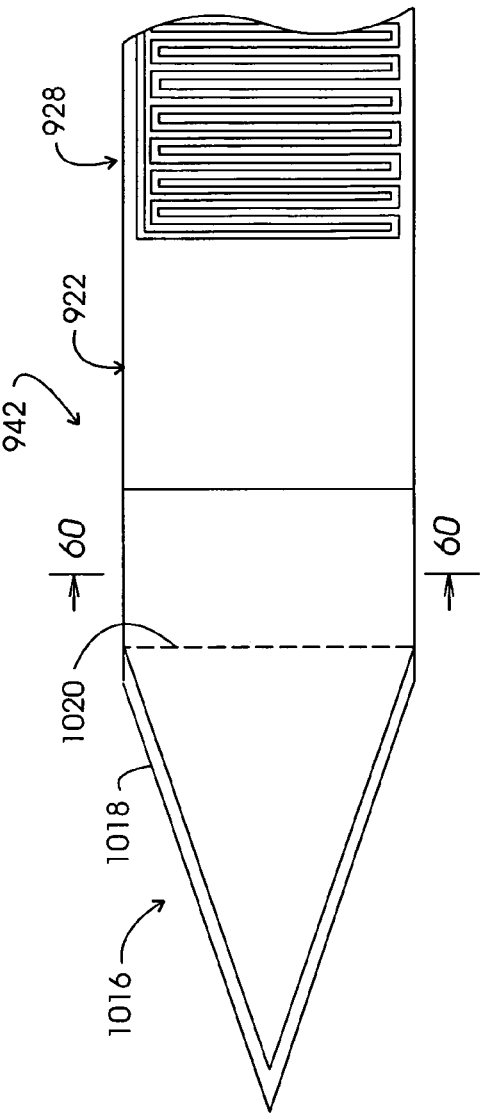
FIG. 58
FIG. 60
FIG. 59

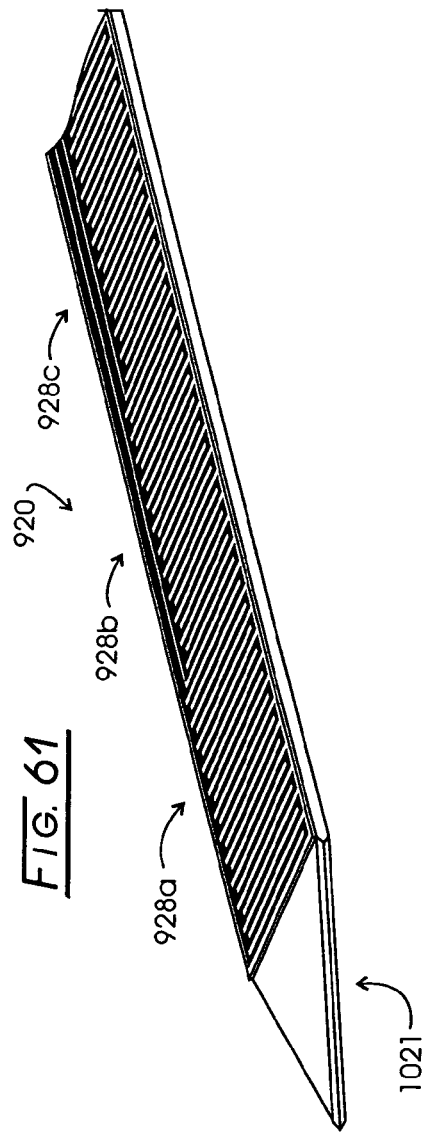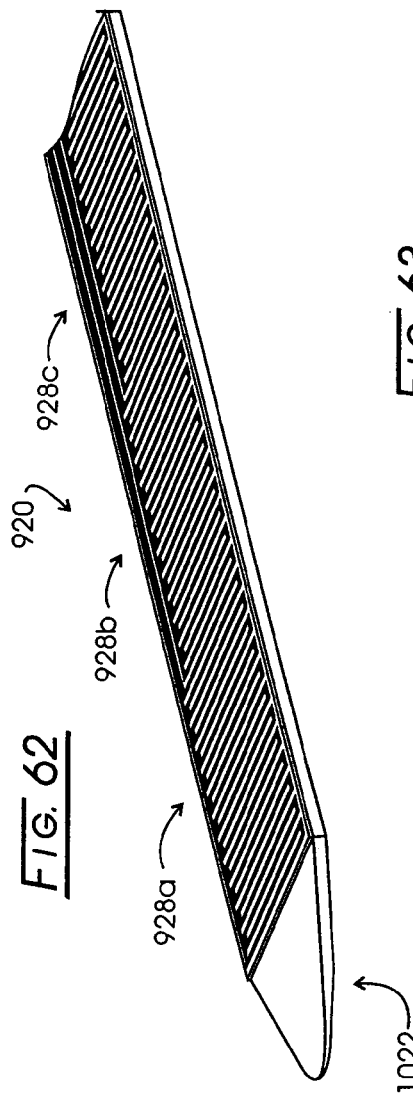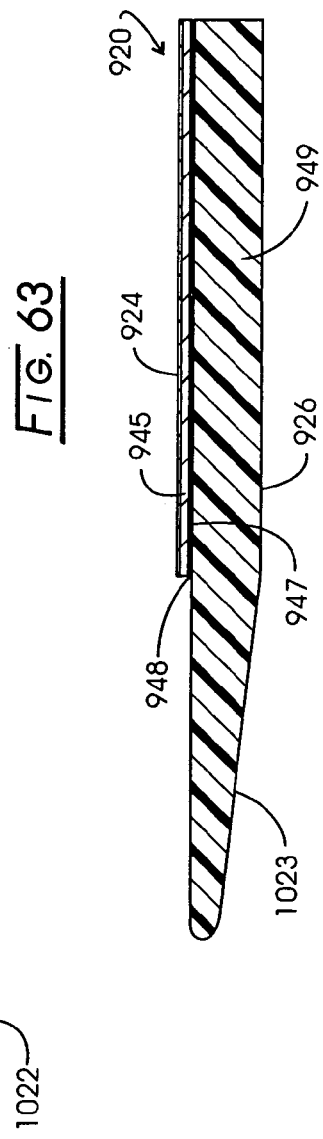

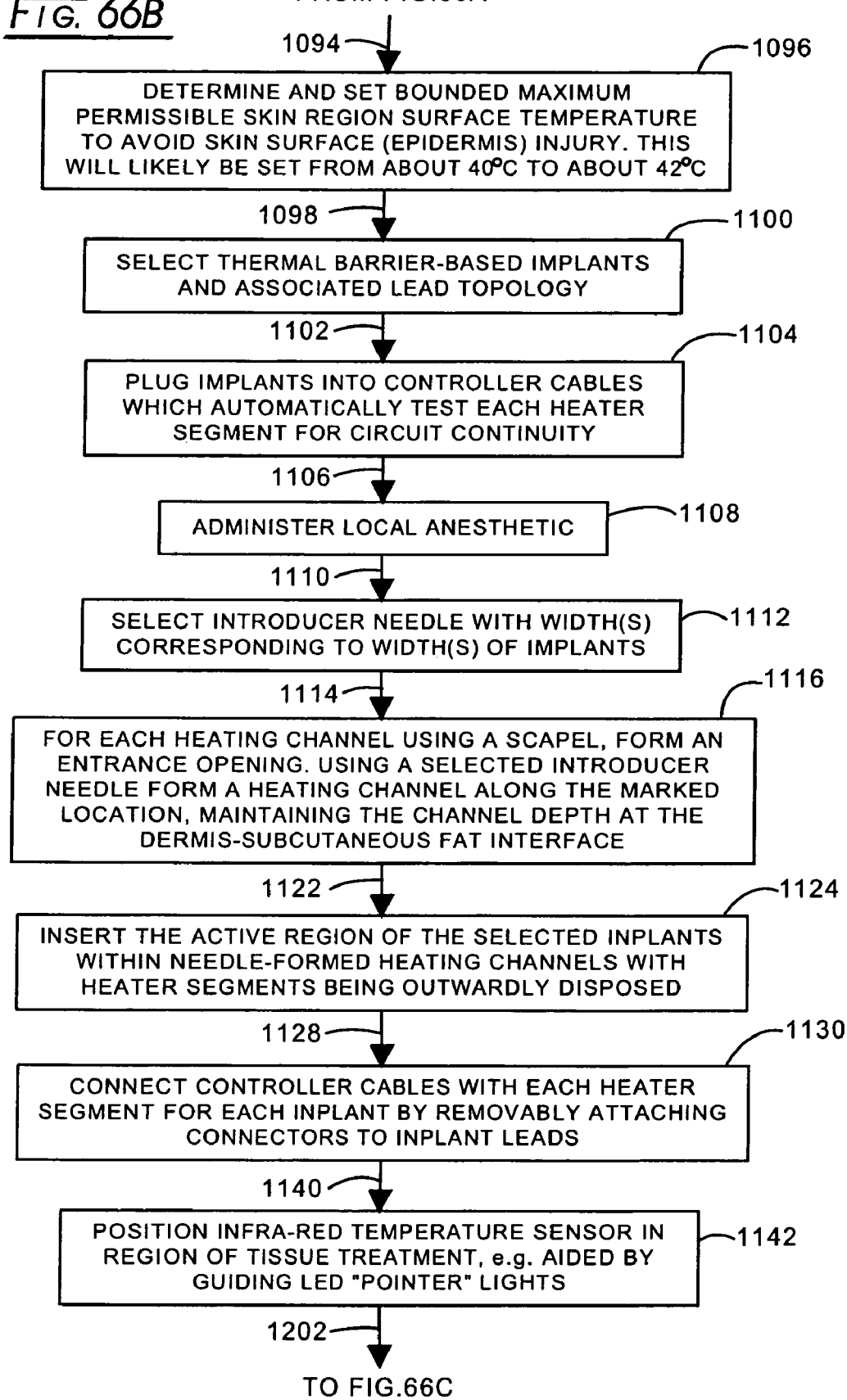

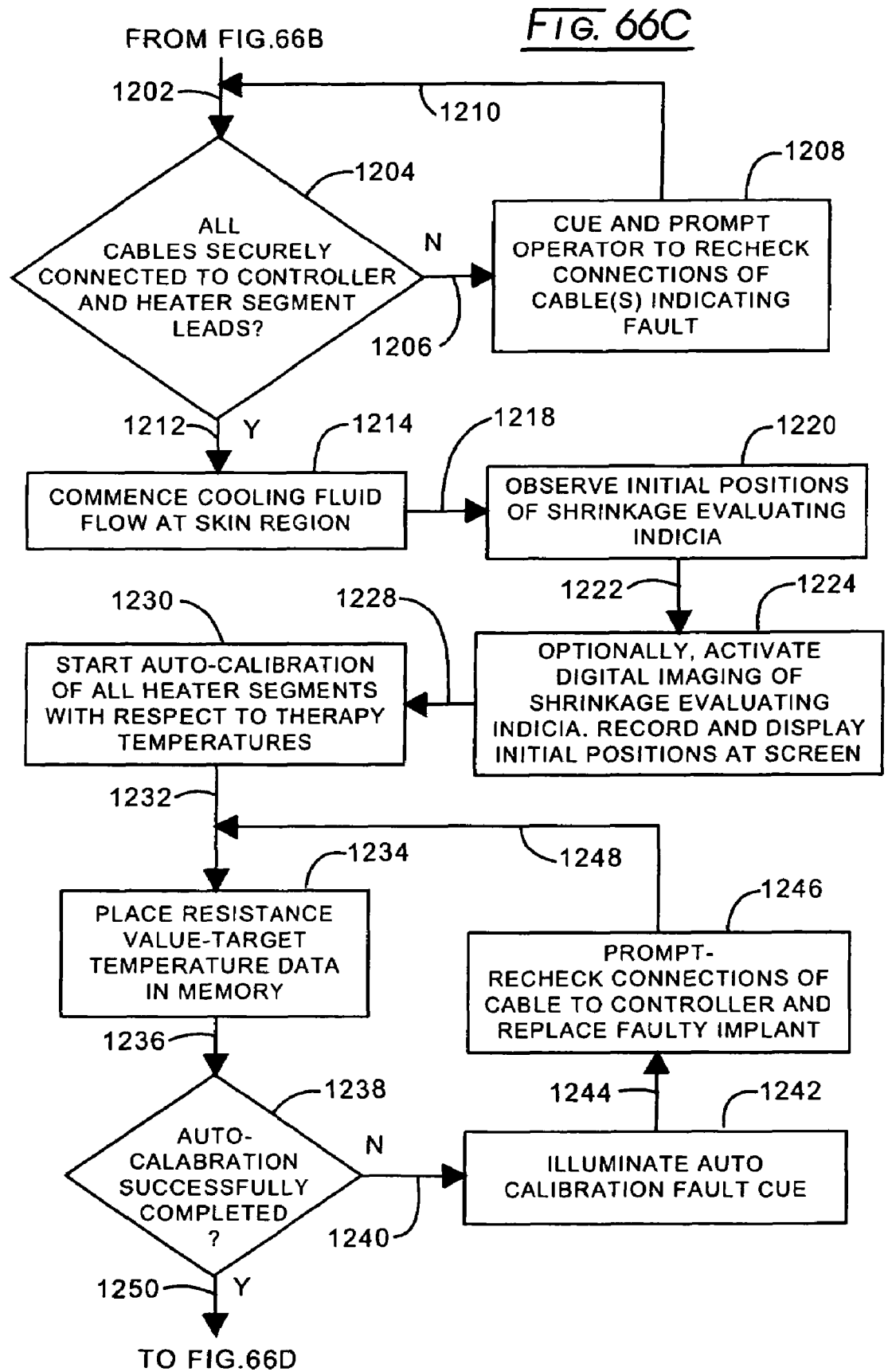

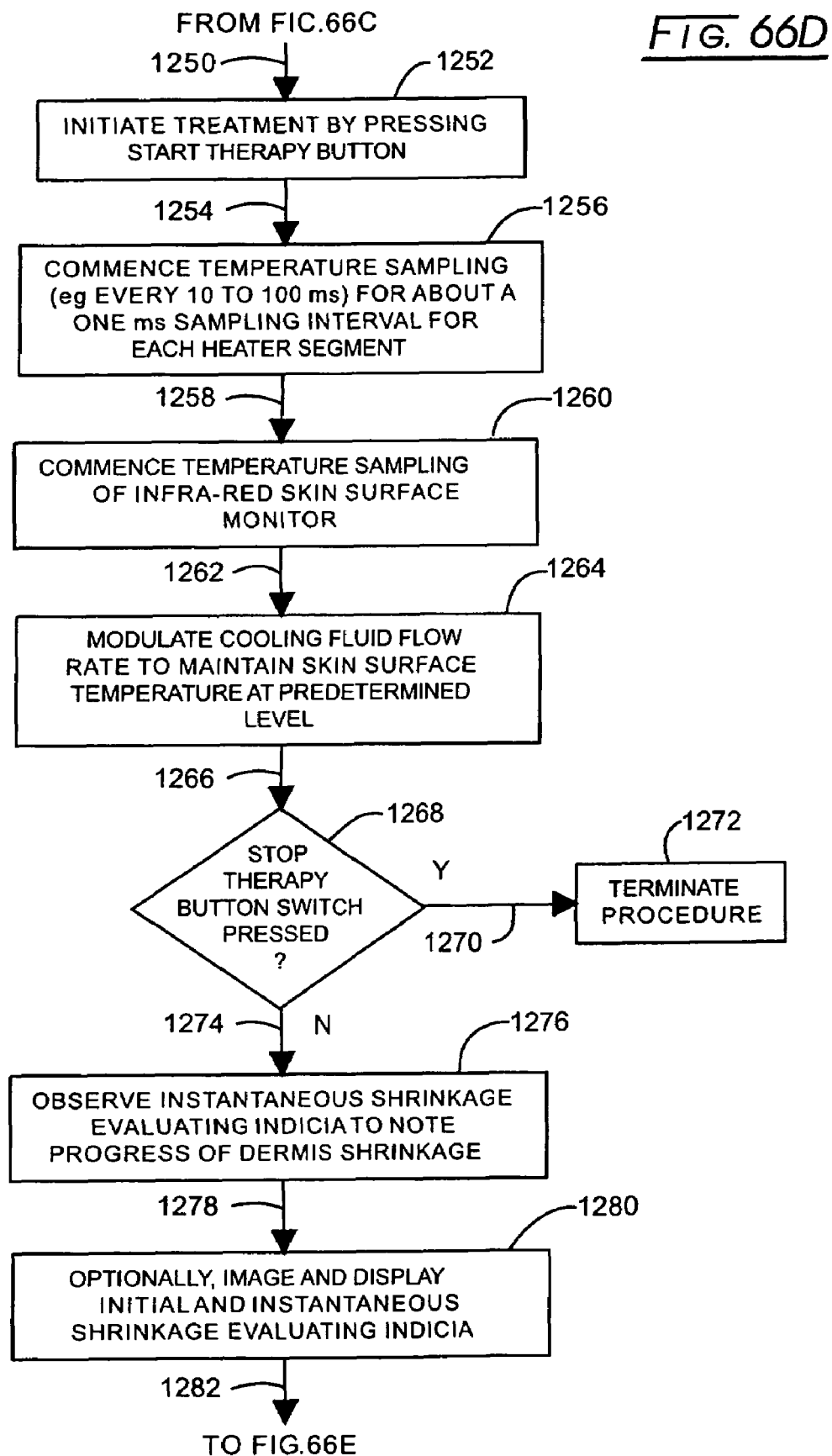

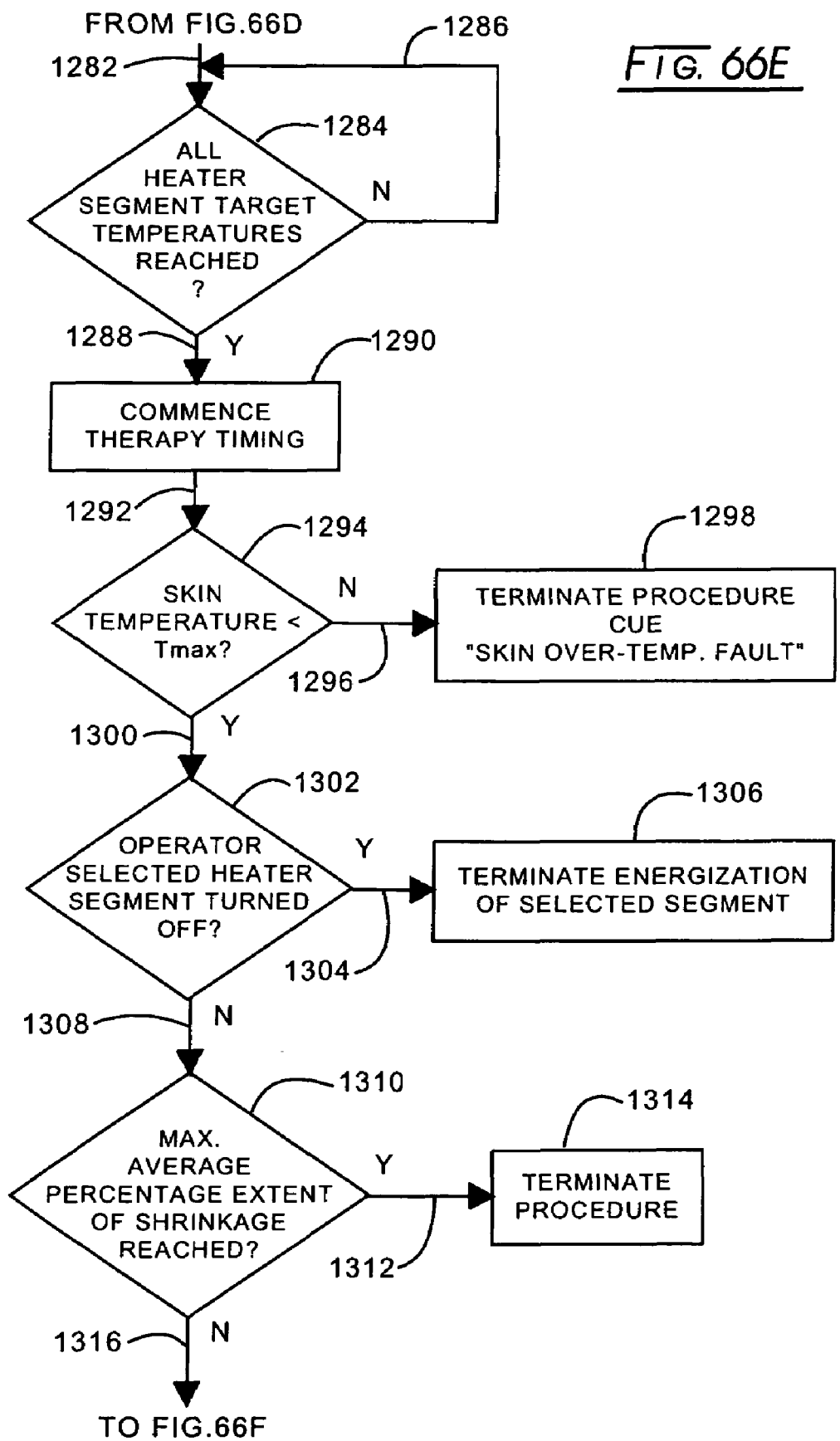

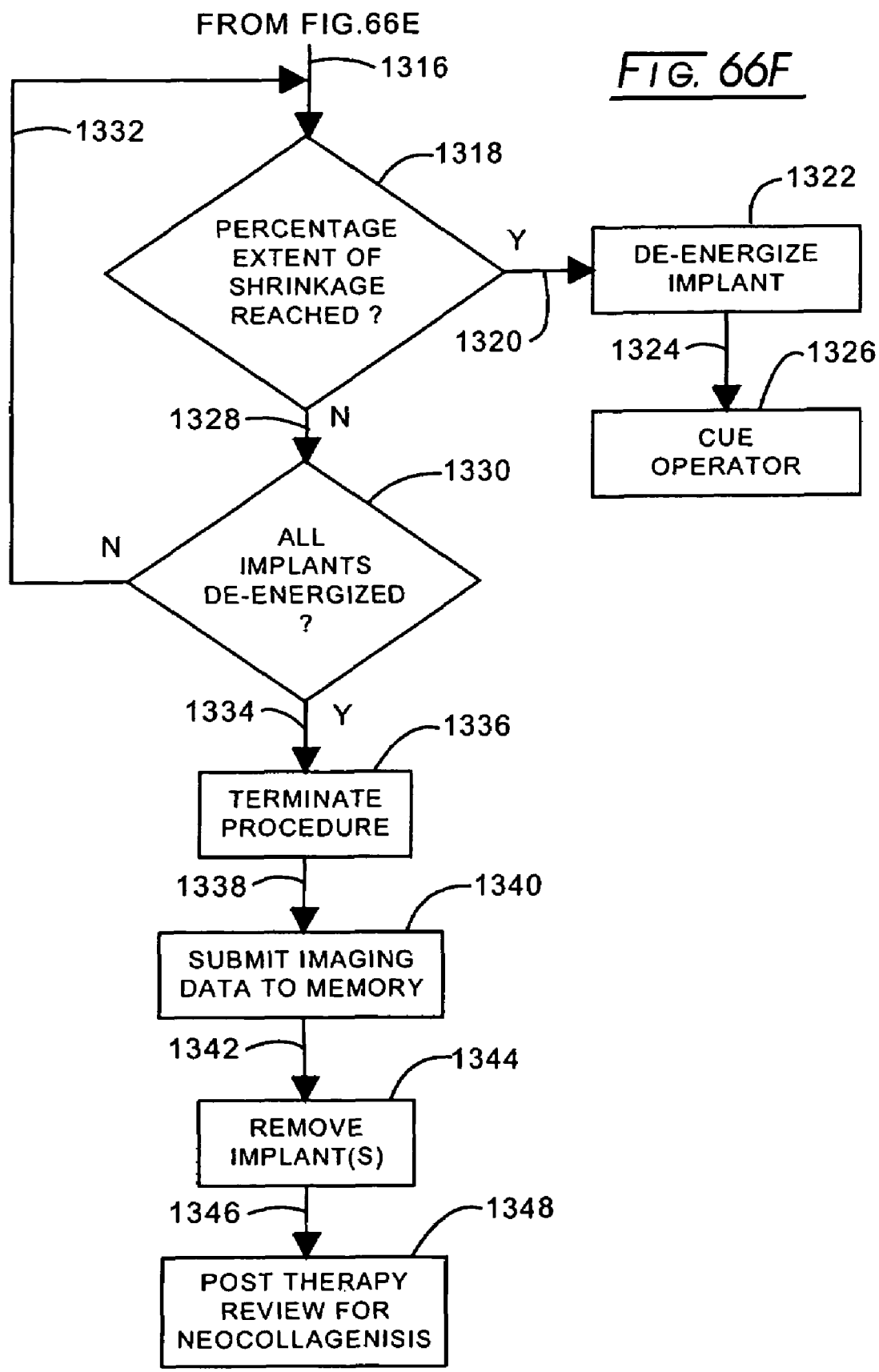

AESTHETIC THERMAL SCULPTING OF SKIN

CROSS-REFERENCE TO RELATED APPLICATIONS

This application is a continuation-in-part of application for U.S. patent Ser. No. 10/733,970 filed Dec. 11, 2003, now U.S. Pat. No. 7,048,756, and is derived from U.S. Provisional application No. 60/677,955 filed May 5, 2005.

STATEMENT REGARDING FEDERALLY SPONSORED RESEARCH

Not applicable.

BACKGROUND OF THE INVENTION

The skin or integument is a major organ of the body present as a specialized boundary lamina. It forms about 8% of the body mass with a thickness ranging from about 1.5 to about 4 mm. Structurally, the skin organ is complex and highly specialized as is evidenced by wound healing wherein the epidermis responds by regeneration and the underlying dermis responds by repair (inflammation, proliferation, and remodeling).

Medical specialties have evolved with respect to the skin, classically in connection with restorative and aesthetic (plastic) surgery. Such latter endeavors typically involve human aging. The major features of the skin are essentially formed before birth and within the initial two to three decades of life are observed to not only expand in surface area but also in thickness. From about the third decade of life onward there is a gradual change in appearance and mechanical properties of the skin which reflect natural aging processes. See generally:

1. Gray's Anatomy, 37$^{th}$ Edition, Churchill Livingstone, New York (1989)

A substantial population of individuals seeking to ameliorate this aging process has evolved over the decades. For instance, beginning in the late 1980s researchers who had focused primarily on treating or curing disease began studying healthy skin and ways to improve it and as a consequence, a substantial industry has evolved. See: "Time Style & Design", Fall 2005 pp 82-85". By reducing and inhibiting wrinkles and minimizing the effects of ptosis (skin laxity and sagging skin) caused by the natural aging of collagen fibrils within the dermis, facial improvements have been realized with the evolution of a broad variety of corrective approaches.

Considering its structure from a microscopic standpoint, the skin is composed of an outer epidermis which is a keratinized stratified squamous epithelium. In this tissue there is a continuous replacement of cells, a mitotic layer at the base replacing cells shed at the surface. Beneath the epidermis is the dermis, a moderately dense connective tissue with greater thickness formed as a collagen fibre which is considered a Type I collagen having an attribute of shrinking under certain chemical or heat influences. Lastly, the dermis resides generally over a layer of contour defining subcutaneous fat. Early and some current approaches to the rejuvenation have looked to treatments directed principally to the epidermis, an approach generally referred to ablative resurfacing of the skin. Ablative resurfacing of the skin has been carried out with a variety of techniques. One approach, referred to as "dermabrasion" in effect mechanically grinds off components of the epidermis.

Mechanical dermabrasion activities reach far back in history. It is reported that about 1500 B.C. Egyptian physicians used sandpaper to smooth scars. In 1905 a motorized dermabrasion was introduced. In 1953 powered dental equipment was modified to carry dermabrasion practices. See generally:

2. Lawrence, et al., "History of Dermabrasion" Dermatol Surg 2000; 26:95-101

A corresponding chemical approach is referred to by dermatologists as "chemical peel". See generally:

3. Moy, et al., "Comparison of the Effect of Various Chemical Peeling Agents in a Mini-Pig Model" Dermatol Surg 1996; 22:429-432

Another approach, referred to as "laser ablative resurfacing of skin" initially employed a pulsed $CO_2$ laser to repair photo-damaged tissue which removed the epidermis and caused residual thermal damage within the dermis. It is reported that patients typically experienced significant side effects following this ablative skin resurfacing treatment. Avoiding side effects, non-ablative dermal remodeling was developed wherein laser treatment was combined with timed superficial skin cooling to repair tissue defects related to photo-aging. Epidermal removal or damage thus was avoided, however, the techniques have been described as having limited efficacy. More recently, fractional photothermolysis has been introduced wherein a laser is employed to fire short, low energy bursts in a matrix pattern of non-continuous points to form a rastor-like pattern. This pattern is a formation of isolated non-continuous micro-thermal wounds creating necrotic zones surrounded by zones of viable tissue. See generally:

4. Manstein, et al., "Fractional Photothermolysis: A New Concept for Cutaneous Remodeling Using Microscopic Patterns of Thermal Injury"; Lasers in Surgery and Medicine 34:426-438 (2004)

These ablative techniques (some investigators consider fractional photothermolysis as a separate approach) are associated with drawbacks. For instance, the resultant insult to the skin may require 4-6 months or more of healing to evolve newer looking skin. That newer looking skin will not necessarily exhibit the same shade or coloration as its original counterpart. In general, there is no modification of the dermis in terms of a treatment for ptosis or skin laxity through collagen shrinkage.

To treat patients for skin laxity, some investigators have looked to procedures other than plastic surgery. Techniques for induced collagen shrinkage at the dermis have been developed. Such shrinkage qualities of collagen have been known and used for hundreds of years, the most classic example being the shrinking of heads by South American headhunters. Commencing in the early 1900s shrinking of collagen has been used as a quantative measure of tanning with respect to leather and in the evaluation of glues See:

5. Rasmussen, et al., "Isotonic and Isometric Thermal Contraction of Human Dermis I. Technic and Controlled Study", J. Invest. Derm. 1964; 43:333-9

Dermis has been heated through the epidermis utilizing laser technology as well as intense pulsed light exhibiting various light spectra or single wavelength. The procedure involves spraying a burst of coolant upon the skin such as refrigerated air, whereupon a burst of photons penetrates the epidermis and delivers energy into the dermis.

Treatment for skin laxity by causing a shrinkage of collagen within the dermis generally involves a heating of the dermis to a temperature of about 60° C. to 70° C. over a designed treatment interval. Heat induced shrinkage has been observed in a course of laser dermabrasion procedures. However, the resultant energy deposition within the epidermis has caused the surface of the skin to be ablated (i.e., burned off the surface of the underlying dermis) exposing the patient to painful recovery and extended healing periods which can be as long as 6-12 months. See the following publication:

6. Fitzpatrick, et al., "Collagen Tightening Induced by Carbon Dioxide Laser Versus Erbium: YAG Laser" Lasers in Surgery and Medicine 27: 395-403 (2000)

Dermal heating in consequence of the controlled application of energy in the form of light or radio frequency electrical current through the epidermis and into the dermis has been introduced. To avoid injury to the epidermis, cooling methods have been employed to simultaneously cool the epidermis while transmitting energy through it. In general, these approaches have resulted in uncontrolled, non-uniform and often inadequate heating of the dermis layer resulting in either under-heating (insufficient collagen shrinkage) or over heating (thermal injury) to the subcutaneous fat layer and/or weakening of collagen fibrils due to over-shrinkage. See the following publication:

7. Fitzpatrick, et al., "Multicenter Study of Noninvasive Radiofrequency for Periorbital Tissue Tightening", Lasers in Surgery in Medicine 33:232-242 (2003)

The RF approach described in publication 7 above is further described in U.S. Pat. Nos. 6,241,753; 6,311,090; 6,381, 498; and 6,405,090. Such procedure involves the use of an electrode capacitively coupled to the skin surface which causes radiofrequency current to flow through the skin to a much larger return electrode located remotely upon the patient. The radiofrequency current density caused to flow through the skin is selected to be sufficiently high to cause resistance heating within the tissue and reach temperatures sufficiently high to cause collagen shrinkage and thermal injury, the latter result stimulating beneficial growth of new collagen, a reaction generally referred to as "neocollagenasis".

To minimize thermal energy to the underlying subcutaneous fat layer these heating methods also attempt to apply energy periods with pulse durations on the order of several nanoseconds to several thousand microseconds for laser based methods and several seconds for radiofrequency electrical current based methods. This highly transient approach to heating the collagen within the dermis also leads to a wide range of temperature variations due to natural patient-to-patient differences in the optical and electrical properties of their skin including localized variations in electrical properties of skin layers. It may be observed that the electrical properties of the dermis are not necessarily homogenous and may vary somewhat within the treatment zone, for example, because of regions of concentrated vascularity. This may jeopardize the integrity of the underlying fat layer and damage it resulting in a loss of desired facial contour. Such unfortunate result at present appears to be uncorrectable. Accordingly, uniform heating of the dermal layer is called for in the presence of an assurance that the underlying fat layer is not affected while minimal injury to the epidermis is achieved. A discussion of the outcome and complications of the noted non-ablative mono-polar radiofrequency treatment is provided in the following publication:

8. Abraham, et al., "Current Concepts in Nonablative Radiofrequency Rejuvenation of the Lower Face and Neck" Facial Plastic Surgery, Vol 21 No. 1 (2005)

In the late 1990s, Sulamanidze developed a mechanical technique for correcting skin laxity. With this approach one or more barbed non-resorbable sutures are threaded under the skin with an elongate needle. The result is retention of the skin in a contracted state and, over an interval of time, the adjacent tissue will ingrow around the suture to stabilize the facial correction. See the following publications:

9. Sulamanidze, et al., "Removal of Facial Soft Tissue Ptosis With Special Threads", Dermatol Surg; 28:367-371 (2002)
10. Lycka, et al., "The Emerging Technique of the Antiptosis Subdermal Suspension Thread", Dermatol Surg; 30:4144 (2004)

BRIEF SUMMARY OF THE INVENTION

The present invention is addressed to method, system and apparatus for carrying out an aesthetic sculpting of skin by an accurately controlled heating of dermis. Heating is accomplished by a controlled contact with dermis using parameters of target temperature and corresponding interval of treatment selected to achieve or approach a determined extent or percentage of collagen shrinkage. Collagen shrinkage evokes or develops a collagen matrix having tensile strength integrity effective to support neocollagenisis. While dermis collagen heating is underway with the method, the subcutaneous fat layer adjacent the dermis, as well as the epidermis are maintained at atraumatic temperature levels. Assurance that the epidermis is maintained at properly low temperature levels can be made by directing a cooling fluid to the skin surface at the region of thermal treatment. Such fluid may, for instance, be a mist or combination of liquid and gas such as water and air.

In a preferred embodiment the subcutaneous tissue (fat) layer next adjacent the dermis is protected by virtue of a heater implant structure having a flat support functioning on one surface as a heater segment support and as a thermal barrier to its opposite side. By locating the support at the junction or interface of the dermis and fat layer, heat energy is directed into the dermis and blocked from migration into the adjacent fat layer. Where electrically resistive heater segments are employed, control over their temperature may be achieved by correlating target temperature with electrical resistance and maintaining the latter while controlling the former. As a consequence of accurate and dermis-confined heat application, practical linear shrinkage percentages can be achieved over quite short intervals of therapy. The extent or percentage of linear shrinkage may be elected by the practitioner along with a desired temperature and associated treatment time by looking to iso-shrinkage temperature and therapy time relationships which may be manifested as a sequence of curves. Time-to-target shrinkage or therapy time may be selected as being sufficiently short such that the practitioner may determine the amount of shrinkage by observing the skin surface at the region of skin being treated.

Those implant embodiments which locate heater component directly within dermis may be provided as a string-like assemblage of discrete heater components which auto-regulate about a target temperature or temperatures under the influence of an extra-body applied magnetic field. Such components may be structured as a generally cylindrical ferrite core exhibiting a very sharp Curie transition at the elected target temperatures. The cores are surmounted by a non-magnetic metal sheath. This string-like assemblage of heater components is tethered with a suture or the like to an introducer needle which functions to draw the auto-regulating heaters within the dermis along a predetermined heater channel. Such implants also may incorporate a temperature sensor such as a ferrite-based passive resonant sensor which may be interrogated by an extra-body excitation system.

This same auto-regulating ferrite-based heater system also may be mounted upon a thermal barrier support and implanted along a heating channel at the noted interface between dermis and next adjacent subcutaneous (fat) tissue. For such an arrangement, the heater components may be provided in a flat form.

Other objects of the invention will, in part, be obvious and will, in part, appear hereinafter.

The invention, accordingly, comprises the apparatus, system and method possessing the construction, combination of elements, arrangement of parts and steps which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 8 is a schematic representation of a heater implant structure formed as a flexible tube;

FIG. 9 is a schematic representation of a heater implant configured with a generally loop-shaped ferromagnetic alloy wire heater;

FIG. 10 is a schematic representation of a heating implant configured as a single electrically conductive electrode which is electrosurgically excited in monopolar fashion;

FIG. 10A is a schematic representation of current density;

FIG. 11 is a schematic representation of an electrosurgically energized heater implant configured for bipolar operation;

FIG. 11A is a schematic representation of parallel, adjacently disposed electrodes of alternating polarity showing current paths;

FIGS. 30A-30D combine as labeled thereon to provide a flow chart of the utilization of the system shown in FIG. 29;

FIG. 33 is a schematic representation of the system of the invention similar to FIG. 29 but utilizing electrical resistance heating implants;

FIG. 34 is a schematic representation of an introducer needle having a circular cross-section;

FIG. 35 is a sectional view taken through the plane 35-35 shown in FIG. 34;

FIG. 36 is a schematic representation of an introducer needle having a generally flat configuration;

FIG. 37 is a sectional view taken through the plane 37-37 shown in FIG. 36;

FIG. 38 is a schematic representation of an introducer needle which is hollow, contains a bladed tip as well as a tip located light emitting diode;

FIG. 39 is a sectional view taken through the plane 39-39 in FIG. 38;

FIG. 40 is a schematic representation of a ferrite-based auto-regulating heater implant combined with a flat polymeric thermal barrier and tethered to an introducer needle;

FIG. 41 is a perspective, broken away view of the heater implant of FIG. 40;

FIG. 42 is a sectional view taken through the plane 42-42 shown in FIG. 41;

FIG. 43 is a schematic top view of a thermal barrier configured electrically resistive heater implant;

FIG. 44 is a sectional view taken through the plane 44-44 shown in FIG. 43;

FIG. 45 is a perspective view of a thermal barrier supported multiple electrical heater segment implant;

FIG. 55 is a schematic representation of a heater implant similar to that shown in FIG. 45 and showing it tethered with an introducer needle;

FIG. 56 is an enlarged partial view of the implant shown in FIG. 55 illustrating a bladed tip configuration;

FIG. 57 is a sectional view taken through the plane 57-57 shown in FIG. 56;

FIG. 58 is a top view of an implant similar to that shown in FIG. 45 but showing an untethered bladed tip;

FIG. 59 is an enlarged partial view of the tip of the implant of FIG. 58;

FIG. 60 is a sectional view taken through the plane 60-60 shown in FIG. 59;

FIG. 61 is a partial view of the tip region of an implant according to the invention;

FIG. 62 is a partial view of the tip region of another implant according to the invention;

FIG. 63 is a schematic partial view of the tip region of an implant according to the invention;

FIGS. 66A-66F combine as labeled thereon to provide a flow chart illustrating the system and method of the invention wherein electrical heater segment and thermal barrier-based implants are employed;

DETAILED DESCRIPTION OF THE INVENTION

Figure 1:
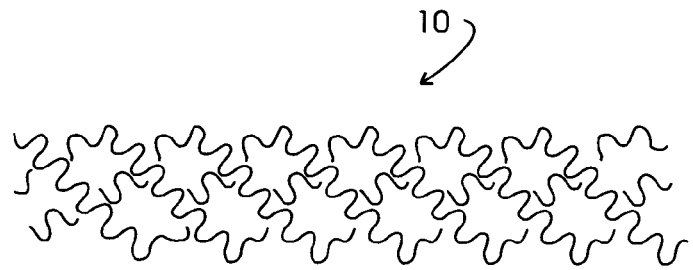
FIG. 1 is a schematic diagram of the helical conformation of tropocollagen.

The secondary structure of collagen is that of an α-helix. A basic tropocollagen is a structure consisting of three polypeptide (procollagen) chains coiled around each other to form a spiral in which the individual collagen molecules are held in an extended conformation (see publication 1 supra at pp 63-66). Molecular forces stabilizing the extended conformation consist of hydrogen bonds, salt links and covalent cross-links. Looking to FIG. 1, a schematic representation of tropocollagen is represented generally at 10. Such tropocollagen is aggregated in parallel form to form collagen fibrils.

Experimental studies have reported that collagen shrinkage is, in fact, dependent upon the thermal dose (i.e., combination of time and temperature) in a quantifiable manner. Looking to FIG. 2, a plot of linear shrinkage versus time for various constant temperatures is revealed in association with plots or lines 12-16. For instance, at line 14, linear shrinkage is seen to be about 30% for a temperature of 62.5° C. held for a ten minute duration. Curve 14 may be compared with curve 12 where shrinkage of about 36% is achieved in very short order where the temperature is retained at 65.5° C. Correspondingly, curve 16 shows a temperature of 59.5° C. and a very slow rate of shrinkage, higher levels thereof not being reached. Clinicians generally would prefer a shrinkage level or on the order of 10 to 20% in dealing with skin laxity.

In general, the dermis is comprised of a matrix of collagen fibrils sometimes referred to as a "scaffold". This scaffold, or matrix plays an important role in the treatment of skin laxity in that once shrunk, it must retain it's position or tensile strength long enough for new collagen evolved in the healing process to infiltrate the matrix. Immediately after the collagen is heated and shrunk it is no longer vital because it has been exposed to a temperature evoking an irreversible cell death. Where the scaffold retains adequate structural integrity in opposition to forces that would tend to pull it back to its original shape, a healing process requiring about four months will advantageously occur. A study has been carried out wherein the mechanical properties of collagen as heated were measured as a function of the amount of shrinkage induced. The results of this study indicated that when the amount of linear shrinkage exceeds about 20%, the tensile strength of the collagen matrix or scaffold is reduced to a level that the contraction may not be maintained in the presence of other natural restorative forces present in tissue. Hence, with excessive shrinkage, the weakened collagen fibrils return from their now temporary contracted state to their original extended state, thereby eliminating any aesthetic benefit of attempted collagen shrinkage.

Figure 3:
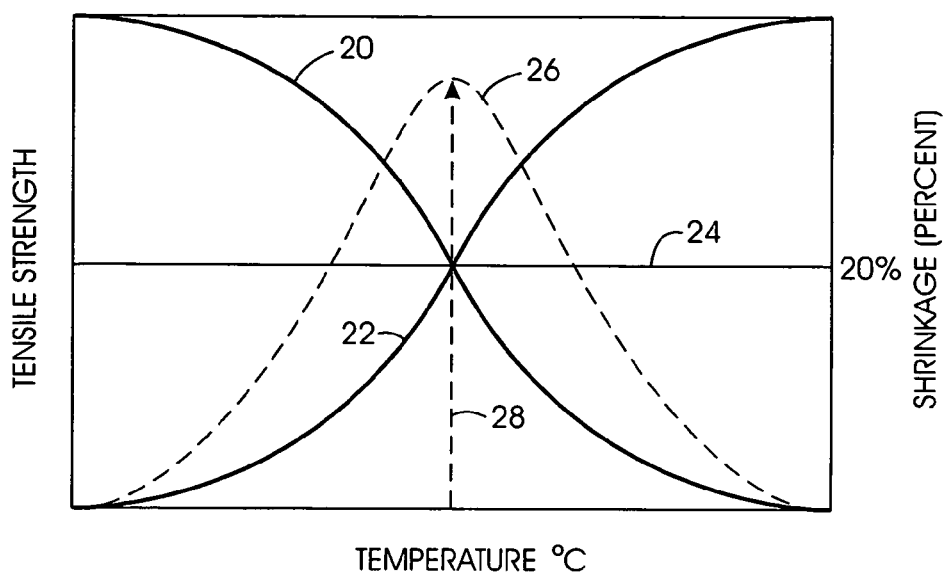
FIG. 3 is a representation of the studied association of shrinkage with tensile strength and temperature over a ten minute interval.

Referring to FIG. 3, a representation of the studied association of shrinkage with tensile strength and temperature over, for example, a ten minute interval is revealed. In the figure, tensile strength is represented at curve 20 as it varies with temperature. Correspondingly, curve 22 plots an exemplary percent shrinkage with respect to temperature. The curves 20 and 22 are seen to cross at the level represented at line 24 which corresponds with about a 20% shrinkage. That 20% shrinkage represents essentially an optimum value wherein sufficient collagen tensile strength to retain scaffold integrity is provided. That integrity will be of sufficient duration to permit neocollagenisis. Dashed curve 26 is a conceptually derived plot illustrating sustainable shrinkage within the collagen matrix or scaffold with respect to temperature. Note, as represented by vertical line 28, that maximum sustainable shrinkage of 20% occurs in alignment with the intersection of curves 20 and 22. That component of the curve 26 to the left of line 28 represents effective available shrinkage and, for example, further represents sustainable shrinkage availability as might be used along the borders of the given treated region to "feather" the collagen shrinkage treatment.

The above studies, inter alia, evolved a 7-parameter logistic equation (sigmoidal function) modeling experimental data for shrinkage, S, in percent as a function of time, t, in minutes and temperature, T, in degrees centigrade. That equation may be expressed as follows:

$$S(t, T) = \frac{[a_0(T - 62) + a_1] - a_2}{1 + \left(\frac{t}{a_3 e^{-a[T-62]}}\right)^{(a_4(T-62)+a_5)}} + a_2 \quad (1)$$

where $a$, $a_0$, $a_1$, $a_2$, $a_3$, $a_4$ and $a_5$ are constant coefficients.

The 7-parameter logistic equation above was utilized to carry out a parametric analysis relating treatment time and temperature with respect to preordained percentages of shrinkage. Looking to FIG. 4, a semi-log plot of treatment time in minutes versus treatment temperature in degrees Centigrade is represented at plot 30. Plot 30 provides an analysis with an assigned 20% contraction or shrinkage of collagen fibril length. Correspondingly, plot 32 provides data for a 10% contraction or shrinkage of linear collagen fibril length. Accordingly, where the clinician wishes to evoke a given percentage of shrinkage, resort to a family of curves as at 30 and 32 may be made to establish the initial parameters for treatment. Plots 30 and 32 are, in effect isoshrinkage lines. Families of curves as at 30 and 32 have particular importance when considering the thermal gradient between a dermis imbedded heat source and distances therefrom. For a further discourse with respect to collagen matrix shrinkage, temperature and treatment time, reference is made to the following publication:

11. Wall, et al., "Thermal Modification of Collagen" Journal of Shoulder and Elbow Surgery; 8:339-344 (1999)

Figure 5:
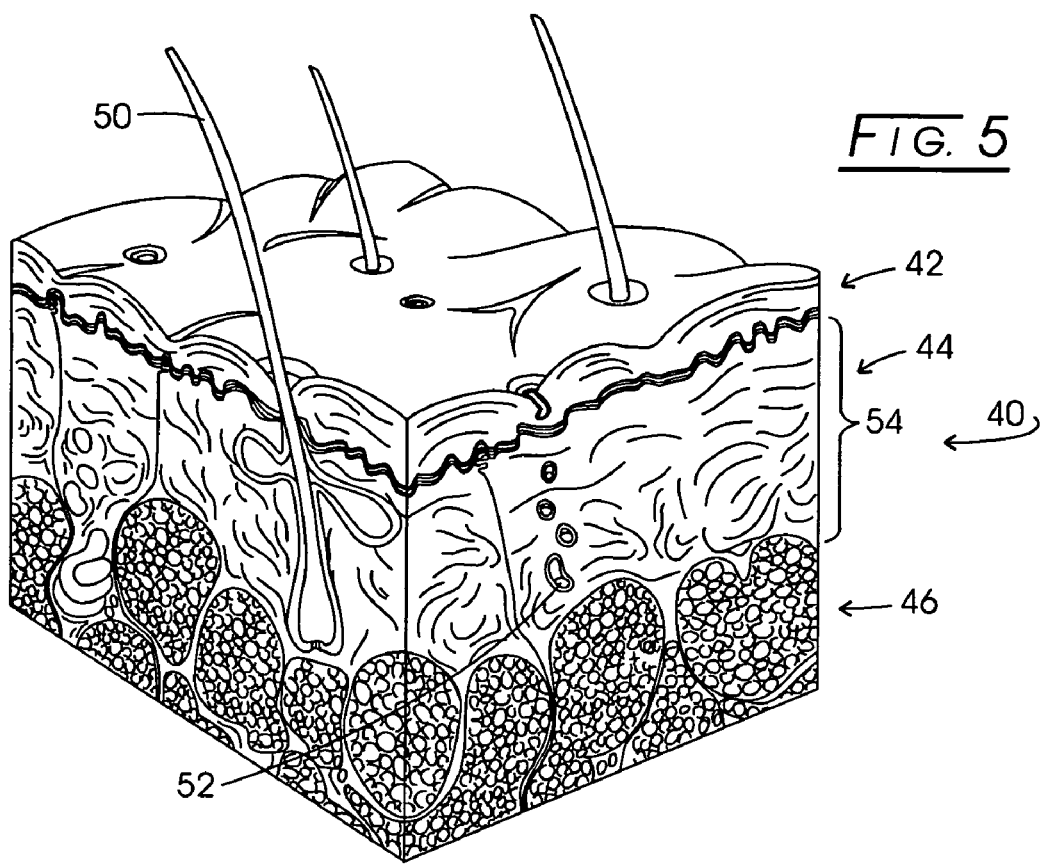
FIG. 5 is a schema representing the organization of skin.

FIG. 5 reveals a schema representing the organization of skin. Shown generally at 40, the illustrated skin structure is one of the two major skin classes of structure and functional properties representing thin, hairy (hirsute) skin which constitutes the great majority of the body's covering. This is as opposed to thick hairless (glabrous) skin from the surfaces of palms of hands, soles of feet and the like. In the figure, the outer epidermis is shown generally at 42 extending over the dermis 44. Dermis 44, in turn, completes integument and is situate over a fat layer represented generally at 46. The figure also reveals a hair follicle and an associated shaft of hair 50 and a sweat duct 52. Heating devices according to the system of the invention will be seen to be in contact with the dermis 44 at a location substantially only between the epidermis 42 and subcutaneous tissue as represented at 46. That region is represented at bracket 54 and may have a thickness of from about 1.5 mm to about 4.0 mm.

Figure 6:
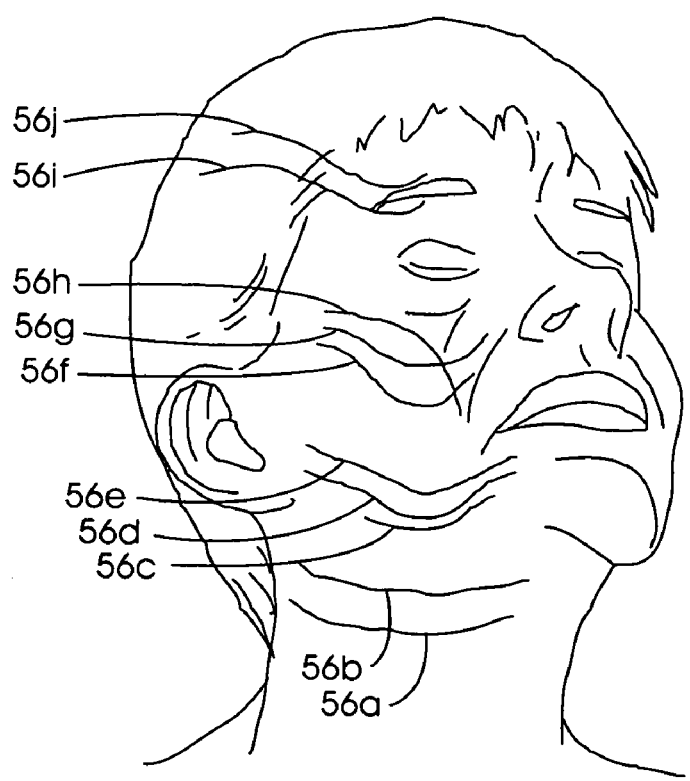
FIG. 6 is a prior art schematic representation of the human head and neck region showing the paths for the location of barbed sutures.

The method at hand for deriving a controlled shrinkage of collagen within the dermis is one which may involve the utilization of elongate introducer needles which are tethered to a corresponding elongate flexible heater implant. The utilization of such needles in conjunction with nonresorbable barbed sutures was developed by Sulamanidze, et al., and is described in connection with publications 9 and 10 above. FIG. 6 is taken from publication 9 and shows the paths or channels developed by the elongate needles and subsequent location of barbed sutures as represented at markings 56a-56j. The present methodology in certain embodiments draws tethered heater implants within the dermis with such introducer needles along predetermined heating channel locations within a determined skin region selected for collagen shrinkage and neocollagenisis.

A variety of heater implant structures may be employed with the instant method. However, the implants for the case of initially discussed embodiments, will have a cross-section or effective cross-section such that they may be located at dermis substantially only between the lower extent of the epidermis and next adjacent subcutaneous tissue. Accordingly, the heater implants are cross-sectionally dimensioned to effectively heat the dermis while avoiding the heating of subcutaneous tissue such as fatty layer 46 shown in FIG. 5. The epidermis as at 42 can be maintained at atraumatic temperature levels by exteriorly developed cooling techniques.

Figure 7:
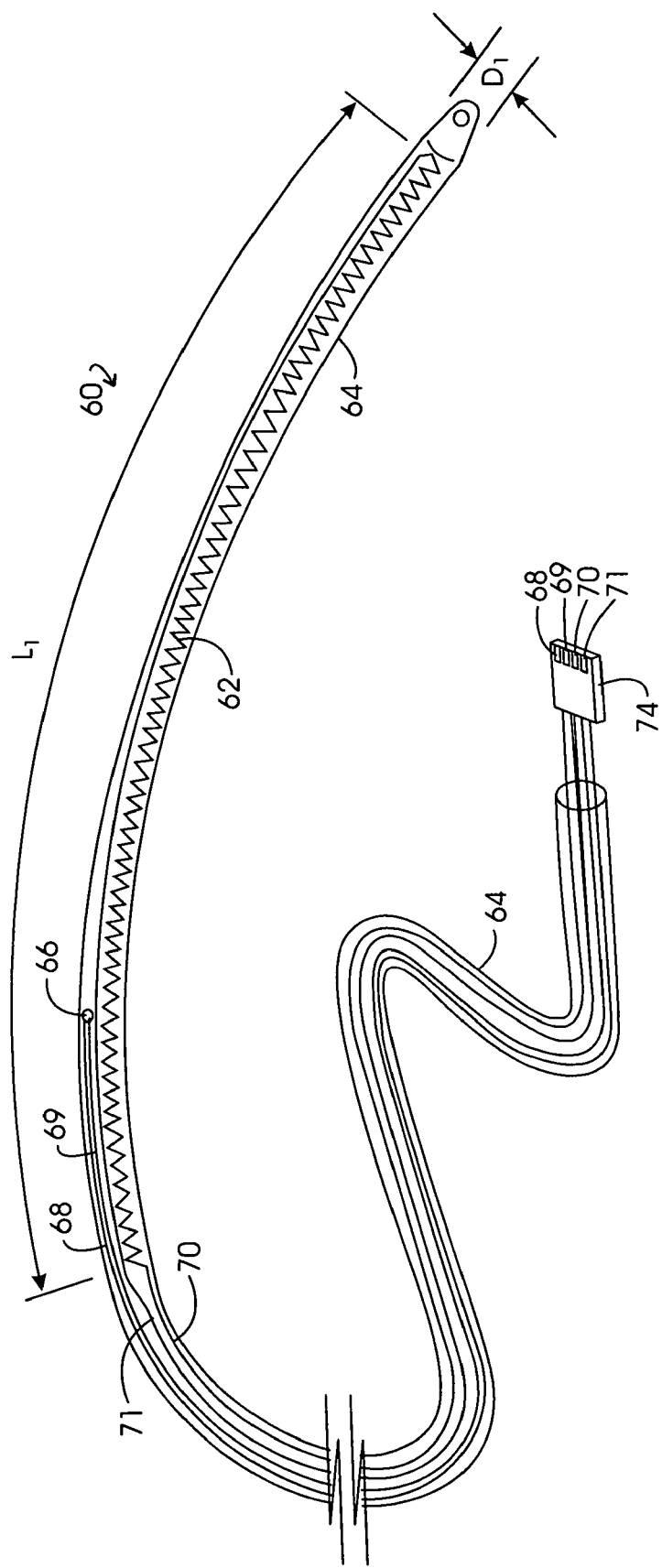
FIG. 7 is a schematic representation of an embodiment for a heater implant utilizing a coil-shaped resistive heating element.

Referring to FIG. 7, an initial embodiment for a heater implant is represented in general at 60. Flexible implant 60 is configured with a long winding coil-shaped resistive heating element 62 which extends along active heating length, $L_1$. Implant 60 is covered with a flexible sleeve 64 formed of a biocompatible material such as Teflon, polyurethane, silicone or the like. A temperature sensor is shown at 66 within the sleeve 64 from which extend leads 68 and 69, while the input and return leads to the resistive element 62 are shown respectively at 70 and 71. These leads extend as terminals to an electrical connector 74.

As an alternative arrangement, the resistant element 62 may be constructed using a bifilar winding configuration such that both ends of the heater wire remain at the trailing end of the implant 60. Heating element 62 may be formed, for example, of metals and alloys such as nichrome, stainless steel, nickel, tungsten, and copper. Having an effective diameter, $D_1$, the resistive element 62 will exhibit a constant power per unit length and may be energized from either a d.c. or a.c. power supply.

Where the element 62 is provided as a resistive material having a large temperature coefficient of electrical resistance, somewhat accurate control over temperature may be achieved as described in U.S. Pat. No. 4,848,337 which is incorporated herein by reference. Such resistive element candidate materials include nickel, copper, tungsten, titanium and silver. Single element heating devices as at 62, however, will be performing in dermis tissue of varying thickness and vascularity. This non-uniform environment may develop non-uniform temperatures along the length, $L_1$.

Referring to FIG. 8, another heater implant structure is represented in general at 80. Implant 80 is formed as a flexible tube 82 having a trailing or input end represented generally at 84 and a leading or output end represented generally at 86. Fluid is inputted to tube 82, for instance, at trailing end 84 as represented at arrow 88. That fluid will have an input temperature, $T_1$. The inputted fluid emerges from leading or output end 86 as represented at arrow 90. In general, the temperature of the output fluid 90 should be within two degrees centigrade of the input temperature, $T_1$. Generally, the diameter of the tube 82, $D_1$, will be about 1 mm and its length, $L_1$, will be about 10 cm to achieve the noted output temperature. The thermal effect within dermis again will depend upon tissue conditions surrounding the implant 80.

Referring to FIG. 9, another heater implant is represented generally at 96. Implant 96 is configured with a generally loop-shaped ferromagnetic alloy wire heater 98 which is flexible. Heater 98 extends from terminals at a trailing end 100 to a leading end shown generally at 102. The element and leads are retained within a flexible sleeve 102. The terminals of element 98 are connected with leads 104 and 106 which emerge at electrical connector 108. Ferromagnetic alloy forming element 98 is selected as having a Curie transition temperature which corresponds with the maximum temperature called for, for heating dermis tissue. For example, that temperature may be about 65° C. The element is energized from a high frequency a.c. supply, for example, a supply providing a constant current within a frequency range of 100 kHz to 30 MHz and more preferably in a range of about 500 kHz to 10 MHz. When the element 98 is below its intrinsic Curie transition temperature current will be confined to flow in a thin layer upon it surface according to well known principals of the "skin effect" associated with the conduction of high frequency current. Where the temperature at any point along the length of heating element 98 reaches its Curie transition temperature, the skin depth for current flow increases substantially and resistive heating decreases accordingly thereby achieving auto regulation along the active elements' length. For a more complete description of skin effect based auto regulation of heating elements, see U.S. Pat. No. 5,480,397 which is incorporated herein by reference. A drawback for auto regulating ferromagnetic alloys resides in a relatively broad temperature response about the Curie transition temperature which may be, for example, a range of about 10° C. to about 15° C. However, the alloys are flexible.

Referring to FIG. 10, another heating implant structure is represented generally at 110. Structure 110 is configured as a single electrically conductive electrode 112 which may be coated with a biocompatible conformal layer (not shown) and is seen to extend from a trailing end represented generally at 114 to a leading end represented generally at 116 which may be coupled via a tether to an elongate needle. Electrode 112 performs in conjunction with a remote relatively large surface area return electrode in a so-called monopolar electrosurgical heating arrangement. In the figure, a coupling between an a.c. RF source 118 and the electrode 112 is shown at 120. This coupling may be an electrically conductive lead wire such as a copper wire covered with an electrically insulative biocompatible coating such as Teflon. A similar connection is directed to the source 118 from the return electrode. Where the electrode 112 is a fine wire, current density will drop off as a function of the radius, r. That radius is represented in FIG. 10A. Inasmuch as power is proportional to $1/r^2$, a decrease in power density of some rapidity is exhibited. Further, the power density in current will vary depending upon the electrical properties of the dermis tissue within which electrode 112 is embedded. For example, some areas of vascularity will be witnessed which will exhibit lower electrical resistance. Care in the use of such monopolar systems also is recommended inasmuch as traumatic current may flow through the vascular components of the fat layer immediately beneath the dermis.

Heater implants also may be configured in a bipolar electrosurgical sense. Referring to FIG. 11, an electrosurgically energized heater implant configured for bipolar operation is represented generally at 126. Device 126 is configured with two electrodes 128 and 130 which are parallel, i.e., uniformly spaced apart. Electrodes 128 and 130 are seen coupled with respective terminals or leads 132 and 134 which are coupled to an RF power supply represented at symbol 136. Terminals 128 and 130 may, for example, be mounted upon a polymeric substrate functioning additionally as a sheath 138. This substrate 138 importantly maintains the noted parallel relationship between the electrodes. Looking additionally to FIG. 11A, parallel, adjacently disposed electrodes of alternating polarity are shown at 140-143 along with dashed regions shown generally at 146-148 representing current paths between these electrodes. By way of example, multiple electrodes as shown in FIG. 10 can be positioned in the dermis having alternating polarities as shown in FIG. 11A.

Figure 12:
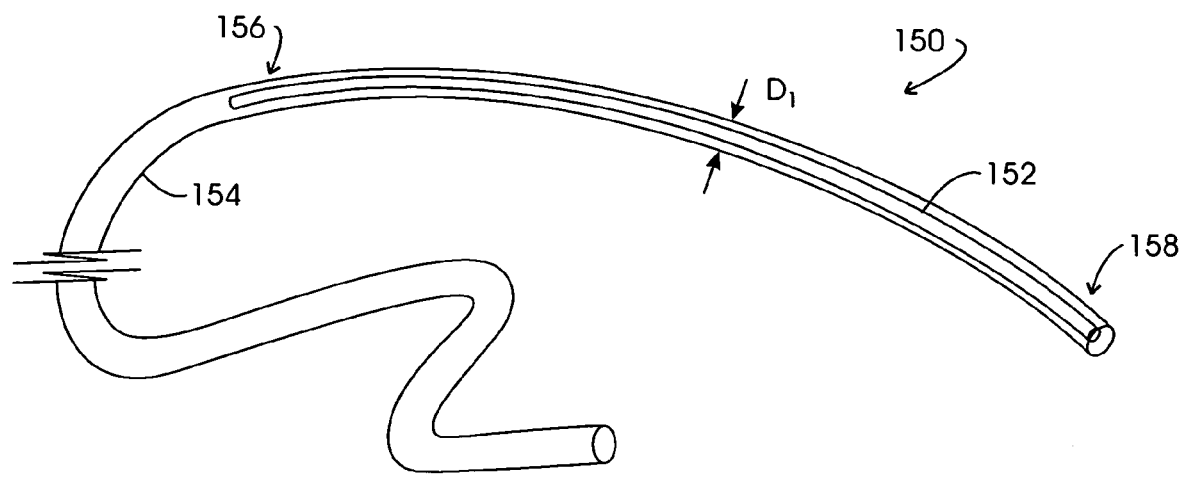
FIG. 12 is a schematic representation of a heater implant formed with a heatable flexible media carried by a flexible sheath.

Referring to FIG. 12, a heater implant is represented generally at 150 which is formed to comprise a heatable flexible media 152 carried by a flexible sheath 154 and extending a length, $L_1$, between its trailing end represented generally at 156 and leading end represented generally at 158. Note that there are no electrical leads or terminals associated with the implant 150. In this regard, energy to effect the heating of media 152 is derived in an extra body manner. For example, the medium 152 may exhibit a high absorptivity to externally applied light, ultrasound or other electromagnetic energy. The media may be a strip or wire of ferromagnetic alloy (e.g., iron/nickel alloy, palladium/cobalt alloy) having a Curie temperature corresponding with the maximum temperature required for the intended heating of dermis tissue. An externally applied electromagnetic field will inductively heat such ferromagnetic material until its temperature approaches a Curie transition temperature whereupon it will auto-regulate its heating rate along its length as discussed above, in connection with FIG. 9.

Figure 13:
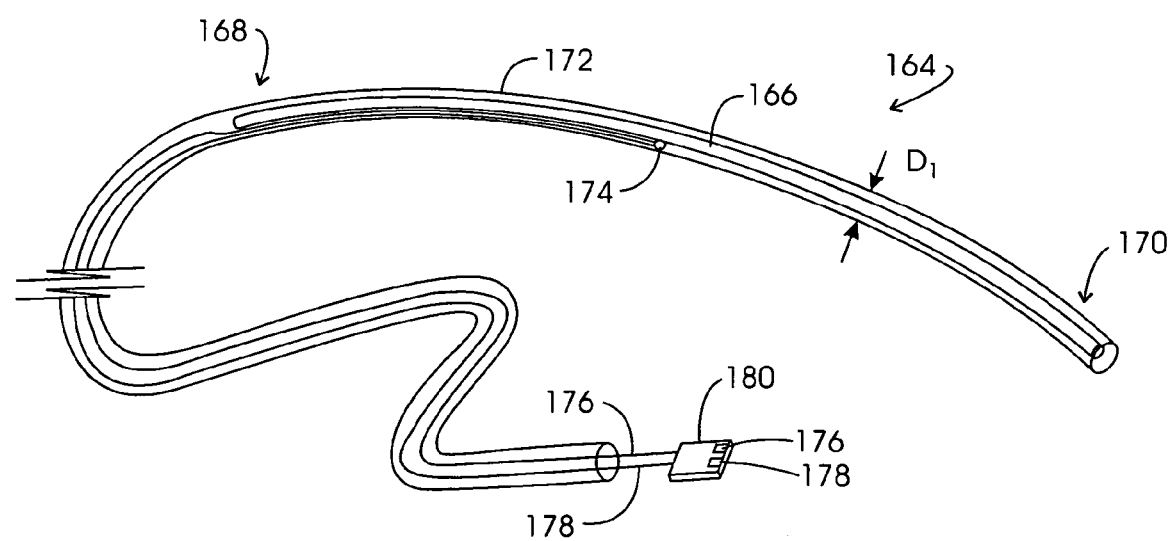
FIG. 13 is schematic representation of a heater implant configured with an elongate flexible heatable media heated from an extra-body source.

Looking to FIG. 13, a heater implant is represented in general at 164. Similar to implant 150, implant 164 is configured with an elongate flexible heatable media 166 and extends from a trailing end represented generally at 168 to a leading end represented generally at 170, a length, $L_1$. Media 166 is heated from an extra body source and thus may be identical to media 152 shown in FIG. 12. It is retained within a flexible sheath 172 in combination with a temperature sensor 174, electrical leads from which at 176 and 178 extend to an electrical connector 180. Sensor 174 may, for example, be provided as a thermocouple, thermistor or the like.

The implants described in connection with FIGS. 7-13 also will be configured for implantation by attachment of their leading ends with an introducer needle, for instance in conjunction with a tethering suture.

Figure 14A:
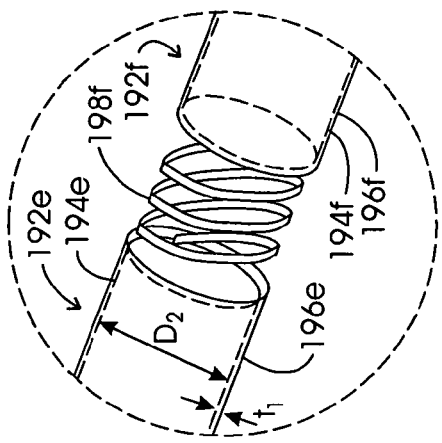
FIG. 14A is an enlarged partial perspective view of an interconnection of components shown in FIG. 14.
Figure 14:
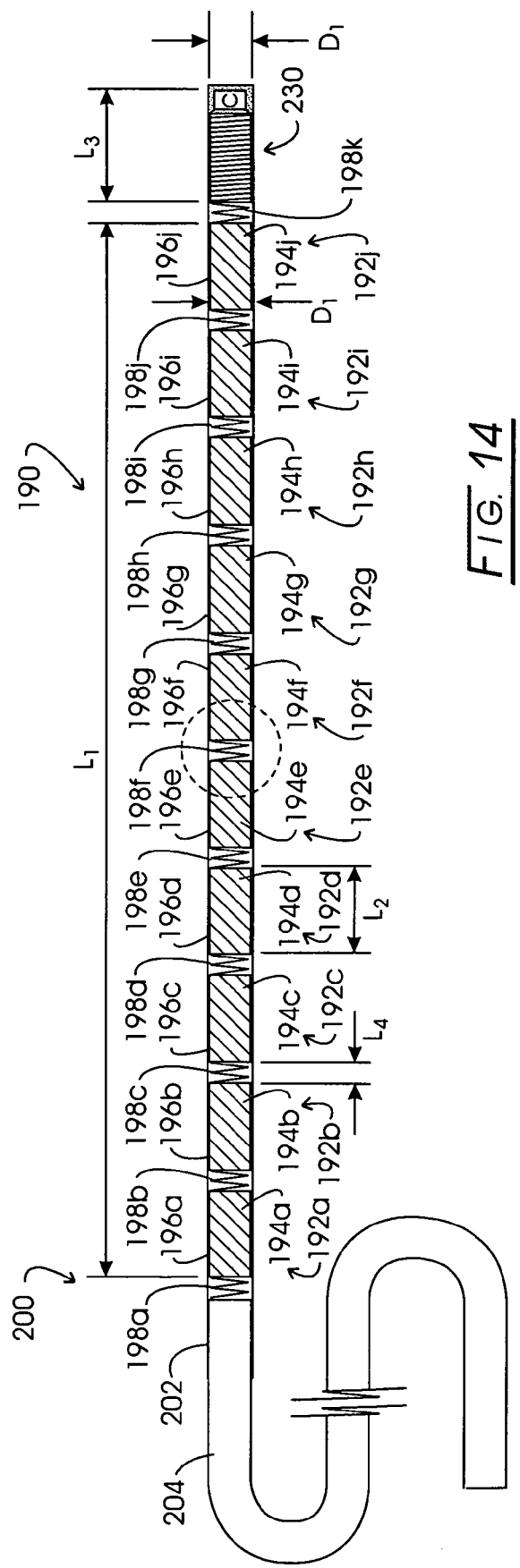
FIG. 14 is a schematic representation of a string-like assemblage of auto-regulating ferrite-based heater segments and passive temperature sensor.

Referring to FIG. 14, a heater implant is represented generally at 190. Implant 190, is, in effect, a flexible, string-like assemblage of auto-regulating components or heater segments represented generally at 192a-192j. Each of the implant components is formed as a carefully formulated ferrite material core shown respectively at 194a-194f. Such ferrite cores are contained within a non-magnetic metal sheath shown respectively at 196a-196j. Looking additionally to FIG. 14A, inasmuch as the ferrite cores 194a-194j are a stiff ceramic material, flexibility is imparted to the implant 190, for example, by providing the sheaths from an elongate length of non-magnetic metal such as stainless steel tubing having an outside diameter, D1, of about 1 mm and a wall thickness, $t_1$, of about 2 mils (0.05 mm for the case of stainless steel). Other non-magnetic metals such as gold may be employed. Where gold sheath material is used, its thickness will be much less than 0.1 mil (0.0025 mm). Each implant or segment will have a length, $L_2$, for example of about 6 mm and their interconnection is by a laser milling of a spaced sequence of helical spring-like connectors as seen at 198*a*-198*k*. The leading end of implant 190 as shown generally at 200 is coupled via connector 198*a* and cylindrical connector sheath 202 by swageing to the end of a flexible suture, for instance, a number 22 suture, represented at 204. The opposite end of suture 204 will be connected typically by swageing with an elongate introducer needle.

Implants or implant components 192*a*-192*j* are represented in FIG. 14 in somewhat schematic fashion. Accordingly, looking to FIG. 15 a more detailed illustration of these auto-regulating heater devices is presented. Here the implant or implant component is represented generally at 210. Device 210 is formed having a cylindrically shaped ferrite core 212. Core 212 is formulated to exhibit a Curie temperature transition at that target temperature determined in connection with the temperature and treatment interval times as discussed above in connection with FIG. 4. The particular ferrite is formulated to exhibit a narrow transition range at that target temperature. Core 212 is surmounted by a cylindrical medical grade non-magnetic metal sheath or tube 214. Such metal may be stainless steel or other metals as discussed above. The internal diameter of sheath 214 is slightly greater than the outer diameter of cylindrical ferrite core 212 to facilitate the manufacturing procedure. Accordingly, a slight gap or annulus configuration is represented at 216.

Note that the ends of sheath 214 at 218 and 220 extend slightly outwardly along the central axis from the respective end surfaces 224 and 226 of ferrite core 212. The spaces defined by these stainless steel sheath extensions are filled or potted with a biocompatible epoxy adhesive. This epoxy adhesive, in addition to filling the outboard region also migrates within the gap 216. The entire implant 190 may be covered with a biocompatible coating represented at 228. Coating 228 may be provided as a Parylene C (poly-monochloro-p-xylylene) coating of thickness ranging from about 0.00025 inch (0.00064 mm) to about 0.010 inch (0.254 mm) and preferably between about 0.0005 inch (0.012 mm) and about 0.001 inch (0.025 mm). These coatings are available from organizations such as Specialty Coating Systems of Indianapolis, Ind.

Notwithstanding the self-regulating nature of the discrete implants as at 210, implants as at 190 also may perform in conjunction with heat sensors. Because of the very shallow depth under the skin surface at which the implants are located, skin surface can be monitored or one or more heat sensors can be incorporated in the multi-component string-like implant as at 190. Returning to FIG. 14, for illustrative purposes, such a sensor is schematically represented at 230. Sensor 230 is a passive resonant implant having an electromagnetic response to an extra-body applied excitation electromagnetic field. More particularly, that response exhibits a predetermined resonant center frequency when the sensor implant is at what is referred to herein as a monitor temperature below a target temperature. In similar fashion, the heater implant components 192*a*-192*j* will produce heat in the presence of a strong electromagnetic field when at such monitor temperatures. While sensors as at 230 may be located at a variety of locations within the implant 190, for convenience, sensor 230 is shown attached to helical connector 198*k*, for example, connection may be provided with a biocompatible epoxy adhesive.

Figure 16:
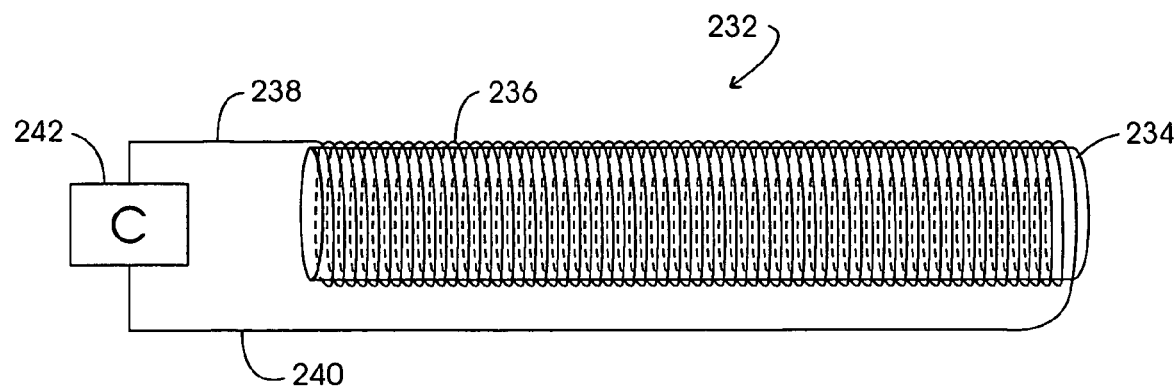
FIG. 16 is a schematic representation of the resonant circuit provided with ferrite-based temperature sensing passive implants.

Referring to FIG. 16, a schematic representation of the resonant circuit provided with each temperature sensing passive implant as at 230 is represented generally at 232. Circuit 232 is configured with a ferrite core component 234 having a Curie transition range extending across the target or setpoint temperature which have been elected. Turns 236 of an inductive winding are shown wound about the core 234 to provide an inductive component. Start and end termini of the windings 236 are seen to extend at leads 238 and 240 to a series coupling with a capacitor 242. The inductance which may be designed for the sensor 232 may be represented by the following expression:

$$L = (\text{const.}) \mu_r A N^2 / l \tag{2}$$

Where L is inductance; $\mu_r$ is relative permeability;
A is the cross-sectional area of the core 234;
N is the number of turns of the windings 236; and
l is the length of the ferrite core component 234.

When excited by an excitation electromagnetic field from an extra body location, the circuit 232 will resonate in accordance with the expression:

$$f_0 = \frac{1}{2\pi\sqrt{LC}} \tag{3}$$

where $f_0$ is the resonant center frequency of the resonant circuit;
L is inductance; and
C is capacitance.

With this arrangement, a plurality of temperature sensing components may be provided, each with a unique resonant center frequency. The particular resonant frequency which is utilized in carrying out temperature sensing in general will fall within a range from about 100 kHz to about 2 MHz. As is apparent from the above two expressions, when the circuit 232 is exposed to temperatures approaching the Curie transition temperature, relative permeability will drop to a value approaching one and, in consequence, the reluctance of the inductor decreases and the associated signal output level issuing from that sensor decreases by 3-fold to 10-fold or more, indicating that the Curie temperature is close at hand. The above expressions also reveal that the various resonant frequencies employed with the system can be adjusted by controlling the number of turns 236 and/or the value of capacitance for capacitor 242. Accordingly, each temperature sensor implant will exhibit its own unique resonant center frequency based signature.

Because the temperature sensing implant circuits as at 232 are excited from an extra body applied excitation electromagnetic field generated as a broad spectrum pulse exhibiting an excitation interval, it is desirable that resonant ringing of circuits as at 232 continue for an interval extending beyond that excitation interval. To achieve this ringing persistence interval it has been found desirable to configure the implant circuits as exhibiting a high quality factor, Q. Q, is a measure of the sharpness of the resonant peak at the −3 dB point. The, Q, of a series RLC circuit may be expressed as follows: Q=$\omega_0$L/R. Accordingly, it is desirable to maintain lower values of resistance which is a factor in the selection of a particular inductive winding wire diameter. It is preferred that the inductive windings 236 be in a single layer in order to avoid a resistance elevating proximity effect and to maintain a minimum overall diameter for the sensor.

Figure 15:
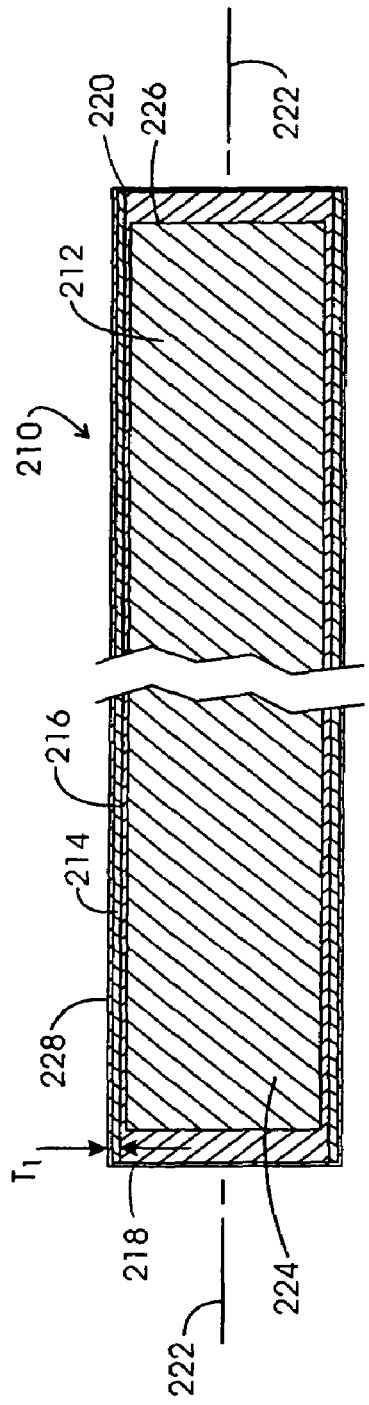
FIG. 15 is a sectional view of the auto-regulating heater components shown in FIG. 14.
Figure 17:
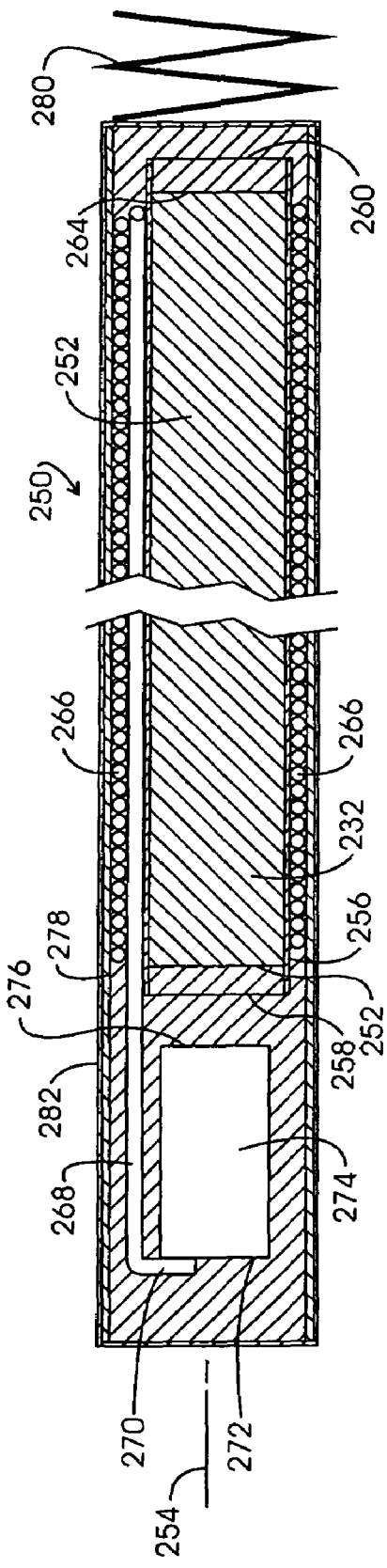
FIG. 17 is a sectional view illustrating the temperature sensing implant components of FIG. 16.

Referring to FIG. 17, a physical structuring of temperature sensing implants as at 230 (FIG. 14) is revealed. Represented generally at 250, the implant includes a ferrite core 252 disposed symmetrically about a core axis 254. Core 252 is selected having a Curie temperature exhibiting a desired transition occurring at a target or elected temperature. Such ferrite cores as well as those described at FIG. 15 are marketed, for example, by Ceramic Magnetics, Inc. of Fairfield N.J. Disposed over the outward surface of core 252 is an electrically insulative polyimide internal sleeve represented at 256. Note that the oppositely disposed ends or edges of sleeve 256 as at 258 and 260 extend axially beyond the corresponding end surfaces 262 and 264 of core 232 to provide support for mounting the ferrite core/sleeve subassembly on an induction coil winding apparatus. Alternatively, the coil may be wound directly on to the ferrite core surface by securing both ends of the core in the induction winding apparatus. The sleeve edges 258 and 260 optionally may be trimmed off, for example, with a scalpel blade prior to further assembly steps. Wound over internal sleeve 256 are the inductive winding turns defining the inductive component of the implant. In this regard, winding 266 commences with an axially extending lead portion 268, the tip 270 of which is bent at a 90° angle to provide for electrical contact with the axially disposed side 272 of capacitor 274. The opposite end of the winding 266 extends axially beneath the winding wrap and is not seen in this figure. However, it is electrically coupled with the axially disposed side 276 of capacitor 274. The windings 266 are retained in position by an epoxy adhesive which is biocompatible with the human body, e.g., Epo-Tek 301 manufactured by Epoxy Technologies, Billerica, Mass. Disposed over the assembly of ferrite core, internal sleeve, inductive winding and capacitor is an electrically insulative polyimide outer sleeve 278. Assembly is completed by potting or filling the voids within sleeve 278 and thus adhesively attaching a helical metal connector as at 280. Connector 280 corresponds with connector 198k described in connection with FIG. 14. As a final step in the implant fabrication process, it's outer surfaces may be covered with a biocompatible coating represented at 282. Coating 282 may be provided as the earlier-described Parylene C.

The ferromagnetic heater implant component, as described in FIG. 14 at 192a-192j may be heated inductively from an excited inductive coil of an alternating current field (ACF) heating assembly. The ferromagnetic heater implants exhibit a temperature-related relative magnetic permeability, $\mu_r$. Such relative permeability may be represented by curve 290 shown in FIG. 18. Relative permeability is expressed as $\mu_r = \mu/\mu_0$, where $\mu$=absolute permeability (Henry/meter), $\mu_0$, is a constant representing the magnetic permeability of free space (Henry/meter) and, $\mu_r$ is therefore dimensionless but ranges from a value of unity to 100 to 5,000 or more. Curve 290 reveals that the relative magnetic permeability, $\mu_r$, decreases as the temperature of a ferrite-based heater approaches its Curie temperature, $T_c$. The ferrite materials at hand advantageously exhibit a sharp transition range commencing with the knee 292 of curve 290. As represented by arrow pair 294, for the materials at hand, the auto regulating heater implant will exhibit a Curie transition range of about 1° C.

Traditionally, the change in magnetic permeability of ferromagnetic alloys with increasing temperature has not been abrupt as would be preferred for precise temperature regulation. Curve 296 is representative of those materials as they perform under the influence of strong electromagnetic fields. The Curie transition range as represented at arrow pair 298 will fall in a range of about 10° C. to 15° C. Such conventional material as has been discussed in connection with FIGS. 9 and 12.

Figure 19:
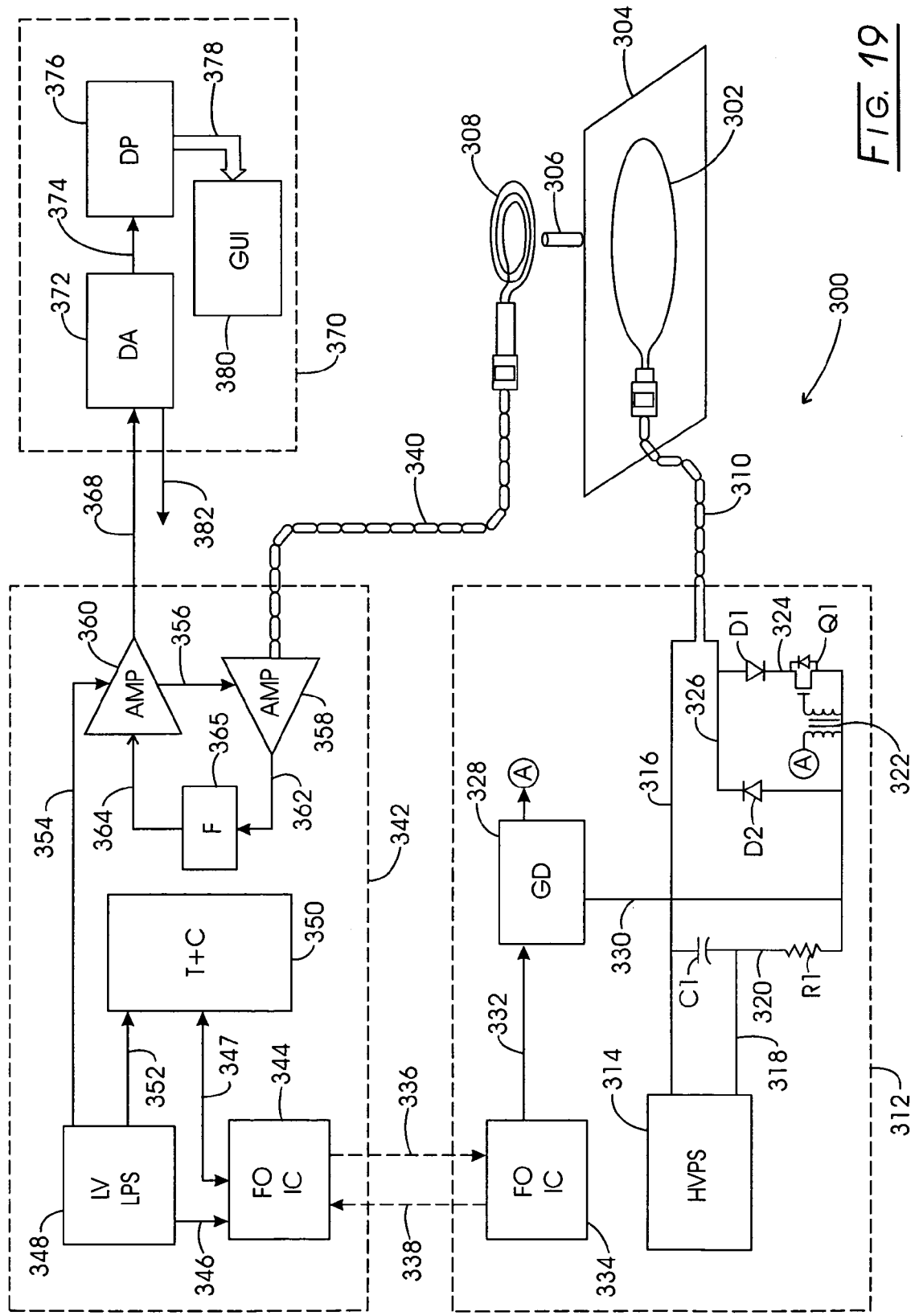
FIG. 19 is a schematic and block diagrammatic illustration of the ferrite-based temperature sensor implant system.

Referring to FIG. 19, a schematic and block diagrammatic illustration of the temperature sensor implant system is presented. Represented generally at 300, the system is shown to include an excitation antenna 302 located in a plane 304 which, in general, will be located somewhat adjacent the neck region of the patient. An exemplary temperature sensing implant is represented at 306. Extending over and about the implant 306 is a sensor antenna 308, having a diameter of about 18 inches. Excitation antenna 302 may, for example, be provided as a single turn of 14 Awg wire having a diameter of about 20 inches. Antenna 302 is seen coupled via a cable 310 to the output of an excitation assembly represented at block 312. Assembly 312 functions to supply an excitation pulse of about one microsecond duration from a 1,000 volt power supply. Accordingly, the excitation antenna 302 may carry a 40 amp peak current with a wave shape of approximately one cycle of a damped sinusoid. In this regard, note that the high voltage power supply is represented at block 314 having a plus output line 316 extending to antenna 302 and a negative output line at 318. A high voltage storage capacitor function, C1, is located between lines 316 and 318 as represented at line 320. Also represented at line 320 is a small sense resistor function, R1. Line 320 also is shown extending to a gate drive transformer 322 which receives a gating input at node, A, and functions to gate a high voltage transistor function, Q1, into conduction. Note that one side of transistor function, Q1, is coupled with line 320, while the opposite side, represented at line 324 extends with steering diode, D1, to a line 326 coupled to antenna 302. Line 326 additionally extends with steering diode, D2, to line 320.

A gate drive circuit is represented at block 328 shown connected to line 320 via line 330 and providing the earlier-noted gating pulse, A. Gate drive circuit 328 is actuated in response to a forward drive input represented at arrow 332. That input is derived at a fiberoptic interface circuit represented at block 334 which is seen responsive to an optical drive input represented at dashed arrow 336. An interface optical output is represented at dashed arrow 338. In operation, when a forward drive gating pulse is applied to transistor, Q1, for about one microsecond, current flows from the storage capacitor function, C1, through excitation antenna 302, then returns through diode, D1, transistor function, Q1, to the storage capacitor function, C1. That represents the forward half-cycle of excitation of antenna 302. When transistor, Q1, is turned off, current flows through diode, D2, through excitation antenna 302 and returns to the capacitor function, C1. The result is a single cycle sinewave excitation. Sense antenna 308 is blocked during this excitation interval, inasmuch as the excitation field generated from excitation antenna 302 will tend to couple with antenna 308. Antenna 308, which may be provided as a paired wire device, is connected through cable 340 to a detector and control function represented at block 342. Function 342 includes fiberoptic interface circuitry represented at block 344. Circuitry 344 is seen to be interactively associated with optical transmission arrows 336 and 338 and is powered as represented at arrow 346 from a low voltage linear power supply represented at block 348. Power supply 348 additionally powers a timing and control logic function shown at block 350 as represented at arrow 352. Function 350 serves to carry out appropriate logic including the duration of excitation pulse, delays before the enablement of antenna 308 and the like and interacts with the excitation function as represented at dual arrow 347.

Also powered from low voltage linear power supply 348, as represented at arrows 354 and 356 is a front-end amplification function represented at 358 and an output amplification function represented at 360. The detected signals from sense antenna 308 are both amplified and filtered following a delay interval occurring subsequent to the excitation interval. That delay interval permits a sufficient dampening of the excitation pulse so as not to interfere with the resonating signals emanating from the temperature sensor implant or implants. Note that cable 340 extends to the input of front-end amplification stage 358. The output of the detector assembly also is seen to be amplified as represented at symbol 360. As part of the signal treatment, as represented at arrows 362 and 364, the sense antenna output is subjected to bandpass filtering as represented at block 366 as well as is stripped of any d.c. term. The bandpass evoked by the filtering function 366 will extend from, for example, about 100 kHz to about 2 MHz.

The amplified sense output is directed, as represented at arrow 368 to a data acquisition and control network represented in general at block 370. Analog signals are sampled at very high rate with a analog-to-digital conversion approach. With this digital approach, the system may apply the full power of signal averaging to lower baseline noise with respect to the associated function of identifying thermal sensor broadcast centerline frequency data. For example, utilizing a point-by-point approach, averaging is carried out and resonant frequency data is derived. For that purpose, Fourier transform approaches are available including the fast Fourier transform (FFT). These functions are represented at dashed boundary 370 as a data acquisition block 372, the output of which is represented at arrow 374. Arrow 374 extends to a data processing algorithmic function represented at block 376. This algorithm is responsive to the center frequency intensity signal and data representing a corresponding unique resonant electromagnetic response of an implant temperature sensor to derive implant status data as detector outputs. These Fourier-type outputs representing a unique resonant center frequency will diminish in amplitude as ferrite core Curie temperature is approached. A ratio of such diminution (instantaneous to maximum amplitude) is used for control and monitoring purposes. As represented at bus arrow 378 and block 380 resultant implant status data is asserted to a graphical user interface or readout assembly to provide visibly discernable information to the operator. Signals to instruct the system to commence carrying out an excitation and sensing sequence may be evolved from the data acquisition function 372. Such signal introduction is represented at arrow 382.

Figure 20A:
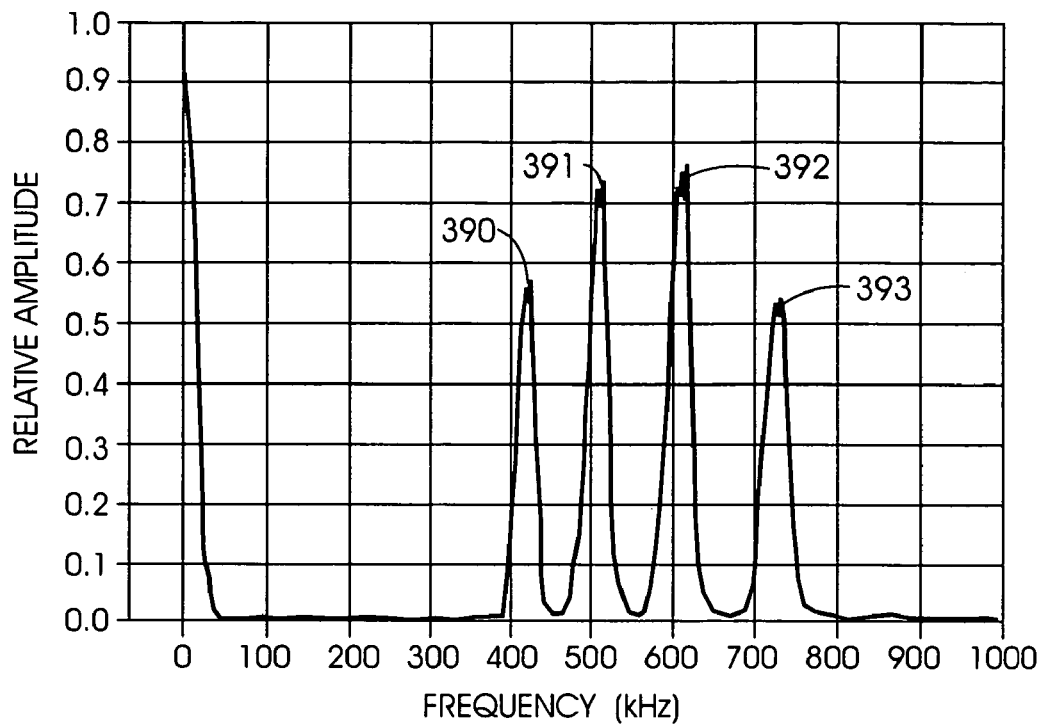
FIG. 20A is a representation of FFT amplitudes of heater sensors shown in FIG. 17 at monitoring temperatures below target temperatures.

An advantageous aspect of the instant system resides in the observation that the resonant center frequency positions do not shift during the temperature interval of Curie transition. As the sensors are heated toward their Curie temperatures, resonant center frequencies remain stable and do not increase or shift. Looking to FIG. 20A, a representation of the FFT amplitudes of core sensors 390-393 having differing resonant center frequencies (kHz) is provided. The figure illustrates typically encountered FFT relative amplitudes corresponding with the intensity of the resonant output of the sensors when at monitoring temperatures well below Curie temperatures.

Figure 20B:
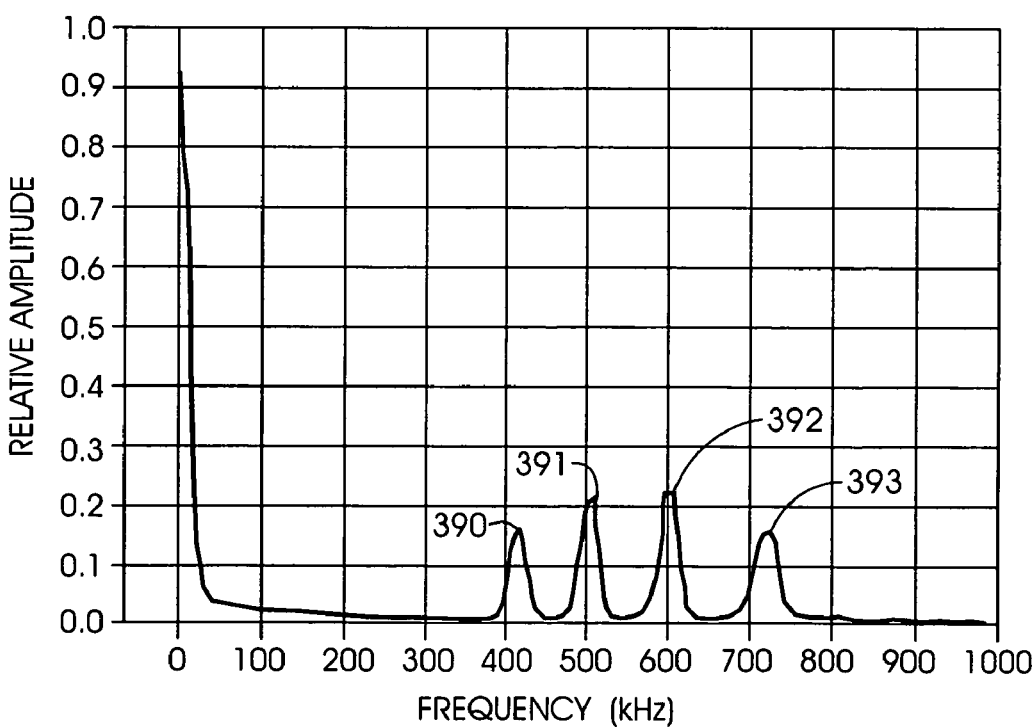
FIG. 20B is an FFT portrayal of the sensors associated with FIG. 20A but showing their FFT amplitudes as monitoring temperatures approach target temperature.

Now referring to FIG. 20B, the FFT relative amplitudes of the same four sensors 390-393 are illustrated during the course of a Curie temperature transition. Note that the resonant center frequencies have remained stable, but the detector output FFTs have diminished in relative amplitude as the temperatures monitored by the sensors approached but did not reach Curie temperature. When the target temperature or Curie temperature is fully reached, these resonant center frequencies shift to an extent that they become off scale.

Figure 18:
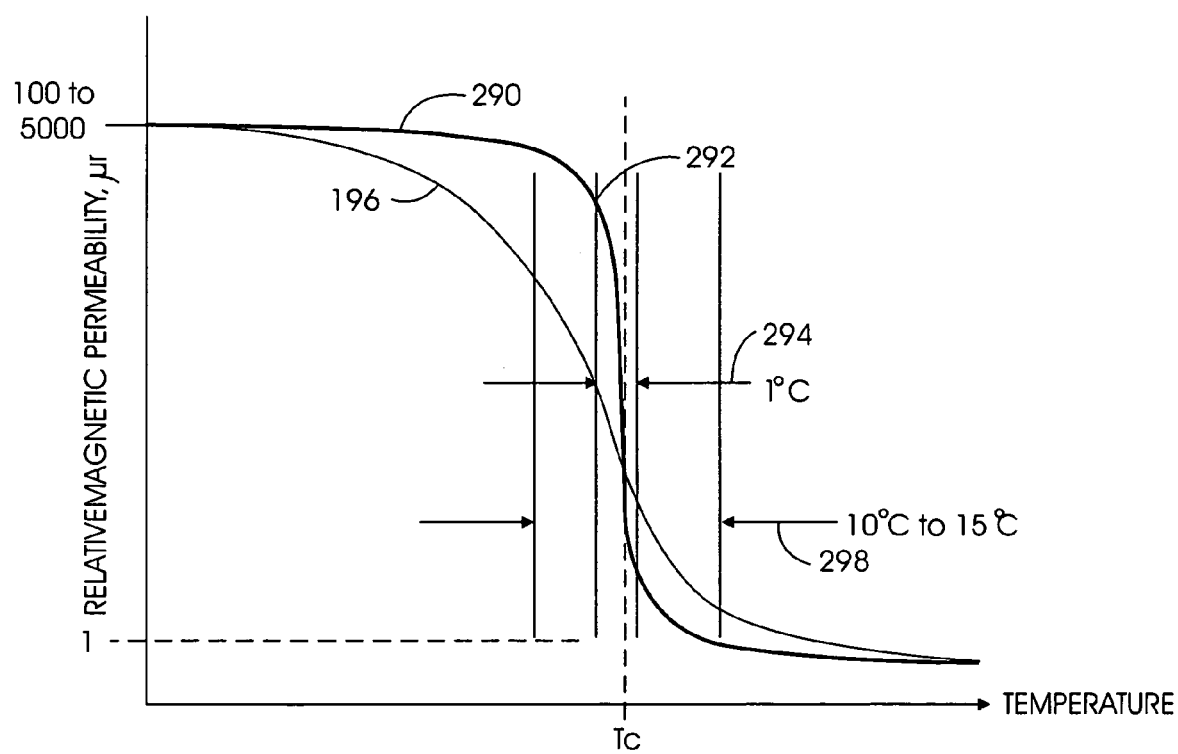
FIG. 18 is a curve relating relative magnetic permeability with temperature for ferrite implants according to the invention and ferromagnetic heater implants.

As discussed in connection with curve 290 in FIG. 18, auto-regulating heater implants as described at 210 in connection with FIG. 15 will be affected in the presence of an inductive excutatuib modality. However, for the materials employed in the instant system and method, Curie temperature transitions will be within much narrower temperature ranges than heretofore have been observed. Looking to FIG. 21, curves relating relative magnetic permeability, $\mu_r$, with temperature, again are revealed. In the figure, curve 400 shows the performance of this ferromagnetic material under the influence of low level applied magnetic field intensities as may be encountered in connection with the temperature sensor implants. As seen at arrow pair 402, the temperature transition range will be about 0.1° C. Where necessary high level applied magnetic field intensities are utilized with the auto-regulating devices as described in connection with FIG. 15, an adequate but not as sharp Curie transition occurs as represented at curve 404 and described earlier in FIG. 18 at curve 290. Represented at arrow pair 406, the temperature range within the Curie transition for this curve is about 1° C. While that auto-regulating transition temperature range is quite acceptable, a very precise control over temperature may be realized where the auto-regulator heater implants are combined with one or more temperature sensor implants.

Figure 22:
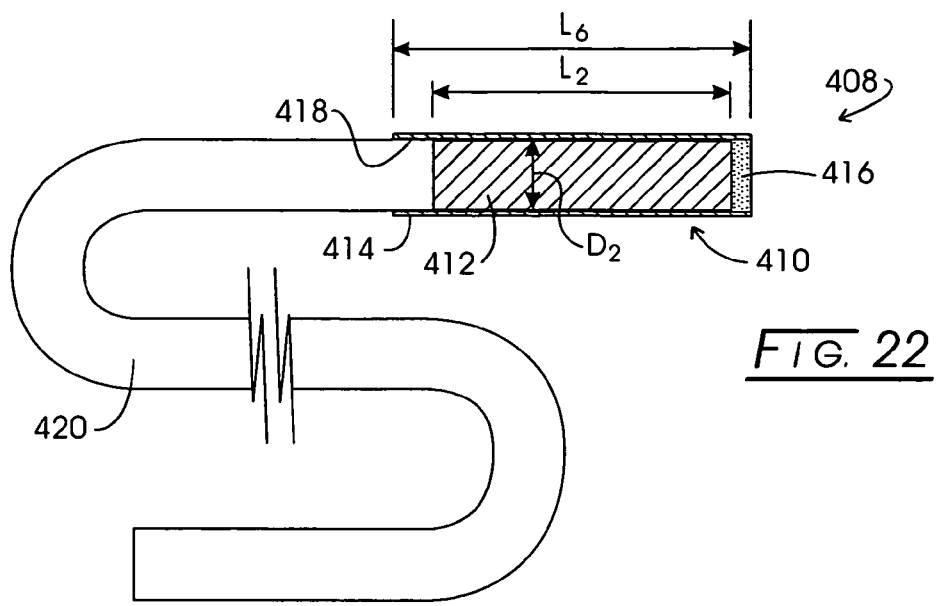
FIG. 22 is a schematic drawing of an implant having a single auto-regulating, ferrite-based heater component.

Returning now to implant configuration, reference is made to FIG. 22 wherein a heater implant is represented generally at 408. Implant 408 contains a single heater implant or component represented generally at 410. Self regulating device 410 is formed with a ferrite core 412 surmounted by a non-magnetic metal sheath. Sheath and core 414 and 412 are potted with a biocompatible epoxy material at end 416. The opposite end 418 of the sheath 414 is attached, for example, by swageing to the end of an elongate suture 420 which, in turn, is employed with an introducer needle. While a temperature sensing modality is not present with the implant 408, it is self regulating about its Curie transition temperature. Supplementary temperature sensing may be provided with adjacently disposed temperature sensing implants as well as more conventional temperature evaluating approaches including infrared sensing at the surface of adjacent epidermis.

Figure 23:
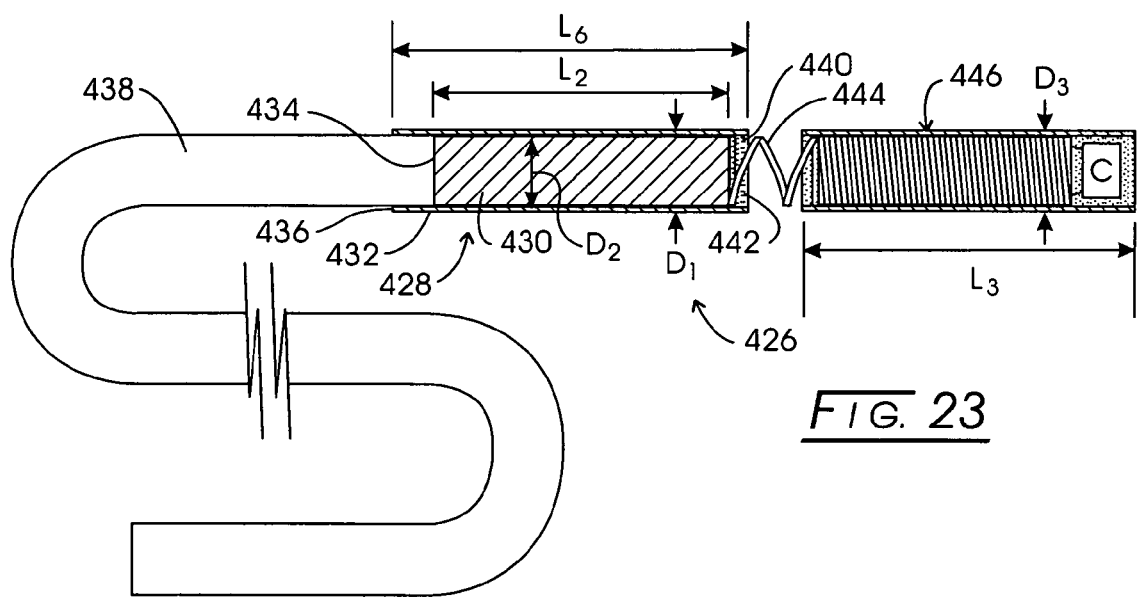
FIG. 23 is a schematic representation of an implant containing a single auto-regulating, ferrite-based heater implant combined with a ferrite-based passive temperature sensor.

A single temperature sensing component may be combined with a singular auto-regulating component. Looking to FIG. 23, such an implant is represented generally at 426. Implant 426 includes an auto-regulating heater component or implant represented generally at 428 which, as before, is configured with a cylindrical ferrite core 430. Core 430 will exhibit a Curie transition temperature corresponding with a desired heating level. The core is surmounted by a non-magnetic metal sheath 432 which extends from the core face 434 to an edge 436 so as to receive one end of a pull thread or suture 438. Connection of that suture 438 with the component 428 generally may be by swaging or adhesive bonding. Sheath 432 also extends beyond the opposite core face 440 to define an attachment cavity 442 carrying a biocompatible epoxy functioning both to encapsulate core 430 and to retain a flexible helical metal connector 444 which, in turn, is adhesively joined with one end of a passive resonant temperature sensor component represented generally at 446. Shown schematically, the temperature sensor 446 is configured in the manner described in connection with FIGS. 16 and 17.

Figure 24A:
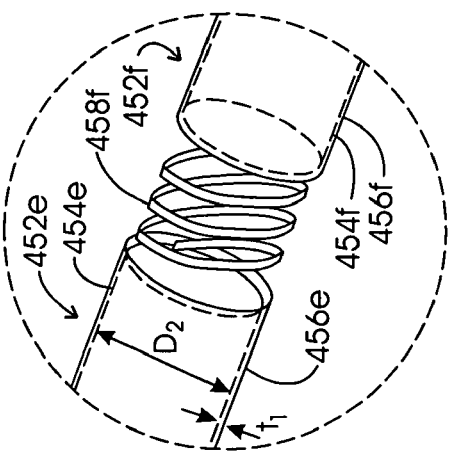
FIG. 24A is a partial perspective drawing showing the interconnection of the heater components of FIG. 24.
Figure 24:
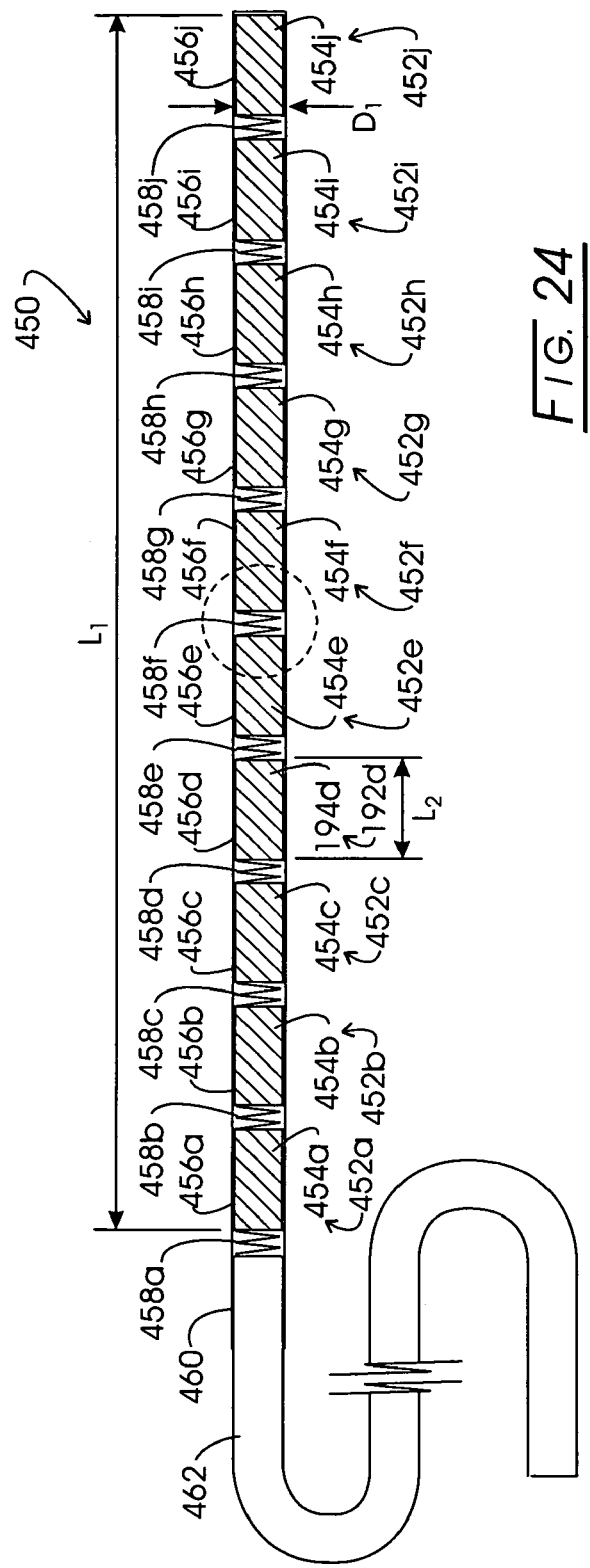
FIG. 24 is a schematic drawing of a string-like linear array of ferrite-based auto-regulating heater components.

Referring to FIG. 24, a string-like linear array of auto-regulating heater components is represented in general at 450. Implant 450 is configured with auto-regulating heater components 452a-452j. Each of these components is configured with a ferrite core shown respectively at 454a-454j. Those cores are retained within non-magnetic metal sheaths shown respectively at 456a-456j. Looking additionally to FIG. 24A it may observed that, as with the structure of FIG. 14, the implant components are flexibly interconnected with integrally formed helical connectors as seen at 458a. Connector 458a is configured with a connector sheath 460 which, in turn, is coupled, for example, by swageing to one end of a pull thread or suture 462. As before, suture 462 is employed in connection with a somewhat elongate introducer needle.

Figure 25:
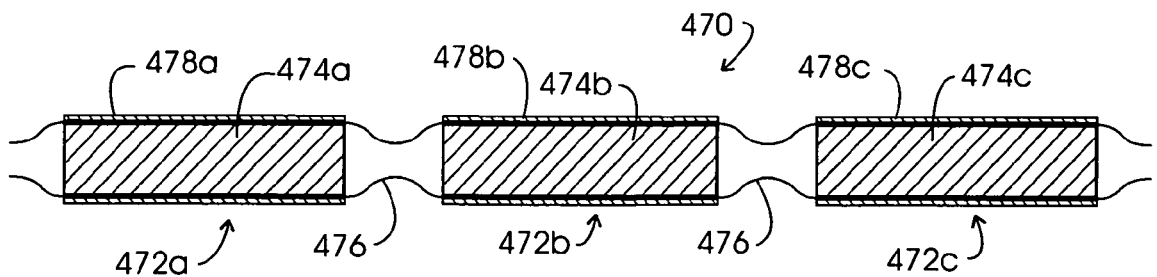
FIG. 25 is a schematic representation of the string-like interconnection of auto-regulating, ferrite-based heater implants which are interconnected with shrink wrap material.

Referring to FIG. 25, another approach to stringing together heater implants or components is revealed in general at 470. In the figure, three heater components are revealed at 472a-472c. Each of these components is configured with a respective ferrite core 474a-474c. These cores 474a-474c are coupled together in string-like fashion to develop a strand by a polymeric shrink wrap 476. Over this electrically insulative shrink wrap 476 there are positioned non-magnetic metal sleeves shown respectively at 478a-478c.

Figure 26A:
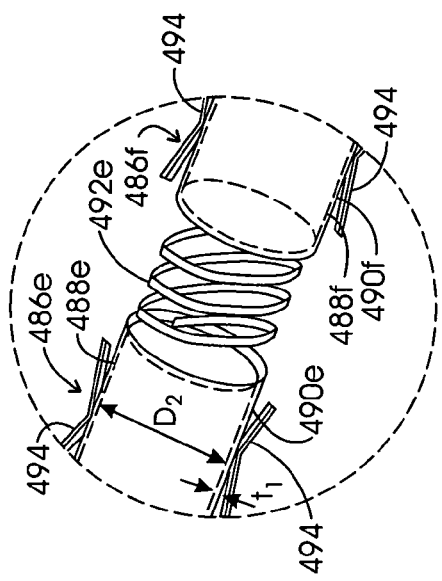
FIG. 26A is an enlarged partial perspective view of the heater components of FIG. 26 and their interconnection.

The instant implants also can be configured to additionally function as a suspension thread in the manner described above in connection with publications 9 and 10. With such an arrangement, there are tissue-anchoring barbs affixed to the surfaces of the heater components such that tissue can be manipulated by the clinician to cause it to contract and retain its contracted state by virtue of the tissue-anchoring barbs. Looking to FIG. 26, such an implant is represented in general at 484. Similar to the embodiment of FIG. 14, implant 484 is configured with ferrite core implemented heater components represented generally at 486a-486j. Each of these heater components is configured with a ferrite core shown respectively at 488a-488j. Those cores are surmounted by non-magnetic metal sheaths identified respectively at 490a-490j. As before, components 486a-486j are flexibly interconnected by integrally formed helical portions or connectors 492a-492i. The configuration of these connectors is shown in enlarged scale in FIG. 26A. That figure also reveals the structuring of barbs formed within the sheaths, certain of which are identified at 494. Attached to heater component 486j is a temperature sensing implant represented generally at 496. Implant 496 is configured in the manner described in connection with FIGS. 16 and 17 and is represented somewhat schematically in the instant figure. Connection is, as before, with helical connector 492j, for example, employing a biocompatible epoxy adhesive. As in the earlier implant embodiments, implant 484 may be installed using an elongate introducer needle in conjunction with some form of attachment, for instance a pull thread or suture 498 coupled at a sheath extension 500.

It may be observed that there is no retraction fiber or suture attached to the implant 484 inasmuch as it is intended to leave it embedded in tissue following the heating and collagen shrinkage procedure for a period that may range from several days to several months. In the latter regard it may be left in the tissue indefinitely.

Figure 21:
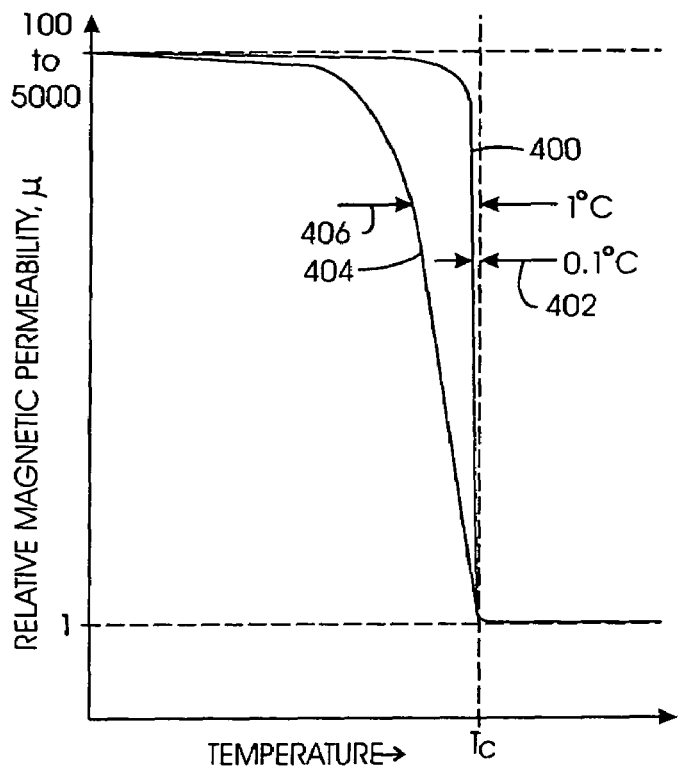
FIG. 21 is a graph relating relative magnetic permeability with temperature.

In their general operation, the ferrite core-based heater components or implants perform in an auto-regulating mode in conjunction with Curie transition phenomena as discussed in connection with FIGS. 18 and 21. In this regard, a magnetic field of appropriate field strength is applied such that the magnetic field lines are approximately aligned (+/−30°) with the longitudinal axis of the ferrite-based implant. Due to the high "conductance" of the high magnetic permeability of the ferrite component to the applied magnetic flux when the ferrite temperature is below its intrinsic Curie temperature, $T_c$, i.e., at monitor temperatures, the applied magnetic flux lines become highly concentrated within the ferrite core. By virtue of the high concentration of magnetic flux lines within that core, a circumferential current is induced in its associated metallic sleeve. The current flow becomes sufficiently large to generate resistance (Joulean) heating within the sleeve. Concentration of magnetic flux lines within the ferrite core continues until the core approaches its intrinsic Curie temperature, $T_c$, (to the right of the knee 292 in FIG. 18). As the Curie temperature is approached more closely, the relative magnetic permeability continues to decrease and the associated resistive heating decreases as well. By virtue of the specially formulated ferrite material, a significant change in the ferrite core's magnetic permeability occurs over a narrow temperature range. As a consequence, the heater component self-regulates over a very narrow temperature range. Importantly, the heater cannot be heated above the intrinsic Curie temperature, $T_c$, of the ferrite core since resistive heating is significantly reduced at or above the Curie temperature.

As a consequence of the noted auto-regulation, the heater components of the implant achieve localized tissue heating through an externally applied electromagnetic field which selectively heats tissue up to but not exceeding a predetermined temperature which is established by the Curie transition temperature. In compliment, the temperature sensor components of the implants serve to provide wireless, non-contact monitoring of the tissue temperature to assure that a minimum predetermined temperature or target temperature has been reached. When used in combination, the auto-regulating heater components and temperature sensor components achieve the heating of targeted tissue within the narrow temperature range determined by the Curie temperature of the ferrite cores.

Figure 27:
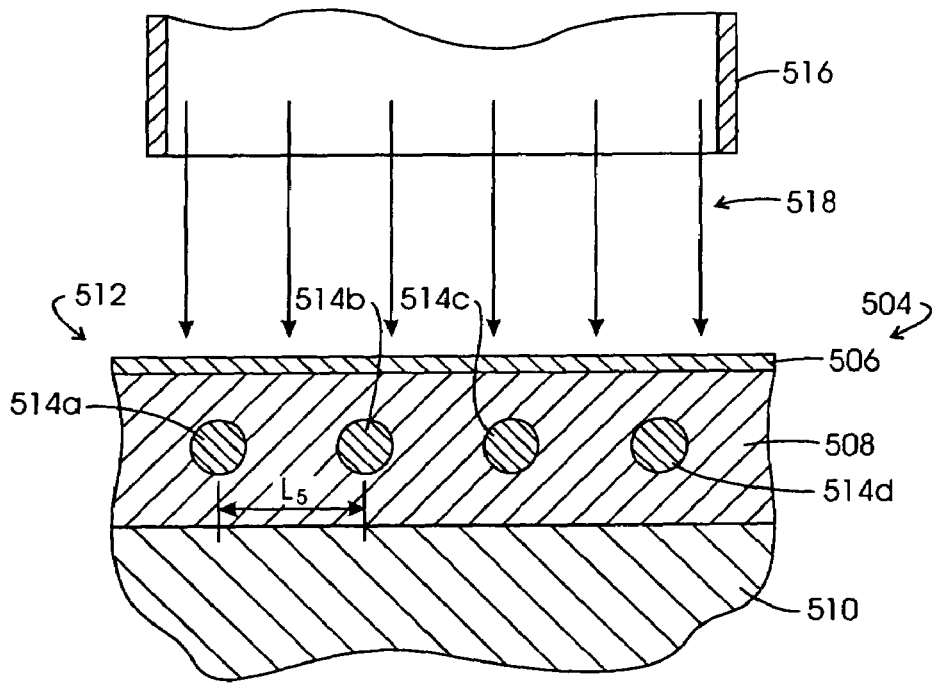
FIG. 27 is a schematic representation of the system of the invention showing skin structure, interdermis implant positioning and skin surface cooling.

Referring to FIG. 27, a skin layer is represented schematically in general at 504. Skin 504 includes epidermis 506 which is located over a dermis layer 508 which, in turn, is supported upon a next adjacent subcutaneous layer which, in general, will be a layer of fatty tissue as represented at 510. A linear array of implants is shown at 512, the implants being illustrated as parallel strings of heaters which may include heat sensors shown at 514a. The temperature of the surface of the skin at epidermis 506 may be controlled by the forced convection of flow of fluid from one or more nozzles as at 516 at temperature, $T_{fluid}$, required to maintain the epidermis below the threshold of unwanted thermal injury. Cooling fluid is represented by arrows 518. The preferred ranges for the various parameters shown thus far are listed as follows:

$L_1$=1 to 50 centimeters
$L_2$=4 to 20 millimeters
$L_3$=4 to 20 millimeters
$L_4$=0.5 to 4 millimeters
$L_5$=2 to 10 millimeters
$L_6$=6 to 24 millimeters
$D_1$=0.5 to 2.0 millimeters
$D_2$=0.4 to 1.9 millimeters
$D_3$=0.5 to 2.0 millimeters
$t_1$=0.02 to 0.2 millimeters
$T_{fluid}$=20 to 45° C.
$T_{heater}$=50 to 80° C.

A rather large range is indicated for the parameter, $L_1$, inasmuch as it is contemplated that the system at hand may be employed in the abdominal region. Correspondingly, the low initial value for $T_{heater}$ is present to accommodate conditions wherein the practitioner wishes to promote neocollagenesis without necessarily shrinking collagen fibrils, i.e., developing scaffold.

The ferrite composition for the heaters is selected so that the maximum allowed tissue treatment temperature is not exceeded. In this regard, a maximum temperature of 65° C. may be selected for the case of collagen shrinkage. Due to self regulation, the ferrite composition can be formulated so that the heater temperature will never rise above a predetermined limit level. The implant array 512 may include temperature sensors and, the temperature sensors may be provided, for example, in alternating ones of the row. Where such temperature sensor components are combined, they may be formulated to detect a minimum tissue treatment temperature, for example, about 62° C. for the case of collagen shrinkage. Thus this lower detected temperature represents a threshold value for shrinkage therapy. Where the passive resonant implant indicates that threshold temperature has been reached, then procedure timing may ensue in correspondence with the computational components of the treatment as discussed in connection with FIG. 4. The temperatures 65° C. and 62° C. described above are given as an example of upper limits and lower threshold temperatures and do not imply a limitation of the values.

Figure 28:
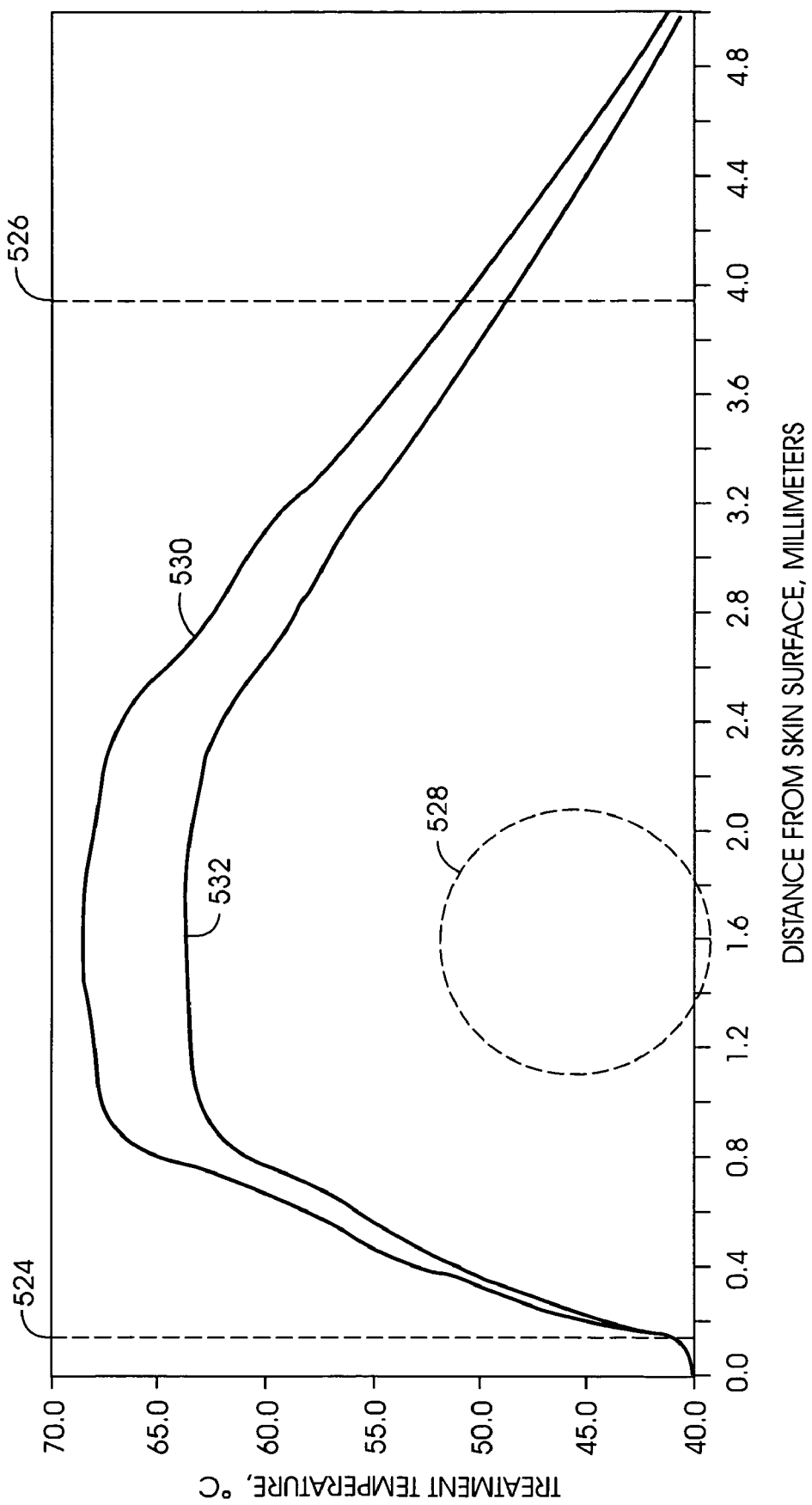
FIG. 28 is a calculated temperature profile within a schematically portrayed skin within which a dermis located implant is positioned.

Referring to FIG. 28, a calculated temperature profile in a vertical plane at the locus of a heater implant, for example, as described at 190 in FIG. 14 is provided. In the figure, the boundary between epidermis and dermis is represented at dashed line 524, while the corresponding boundary between dermis and next adjacent subcutaneous tissue such as fat is represented at dashed line 526. The cross-section of a heater implant is represented at dashed circle 528. Curve 530 represents a computation of temperature distribution generally within the dermis and adjacent fatty layer for a heater temperature of 70° C. Correspondingly, curve 532 is a computed representation of temperature distribution for a heater implant temperature of 65° C. A forced convection cooling of the epidermis at its surface allows it to be maintained, for example, below about 45° C. and therefore below a threshold of unwanted thermal injury. Dermis is intentionally heated in the range from 50° C. to about 70° C. to effect collagen shrinkage, new collagen generation (neocollagenesis) and associated aesthetic skin tightening. The layer of subcutaneous fat preferably is maintained below about 50° C. to avoid unwanted thermal injury.

Figure 4:
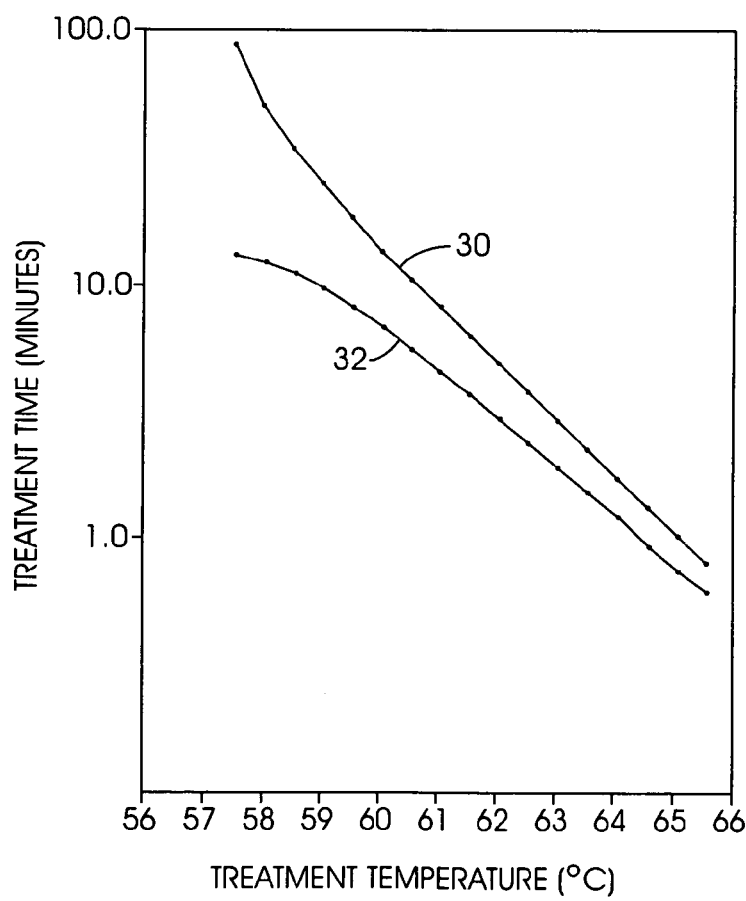
FIG. 4 is a semi-log plot of iso-shrinkage curves relating treatment time in minutes versus treatment temperature for a 20% contraction and a 10% contraction.
Figure 29:
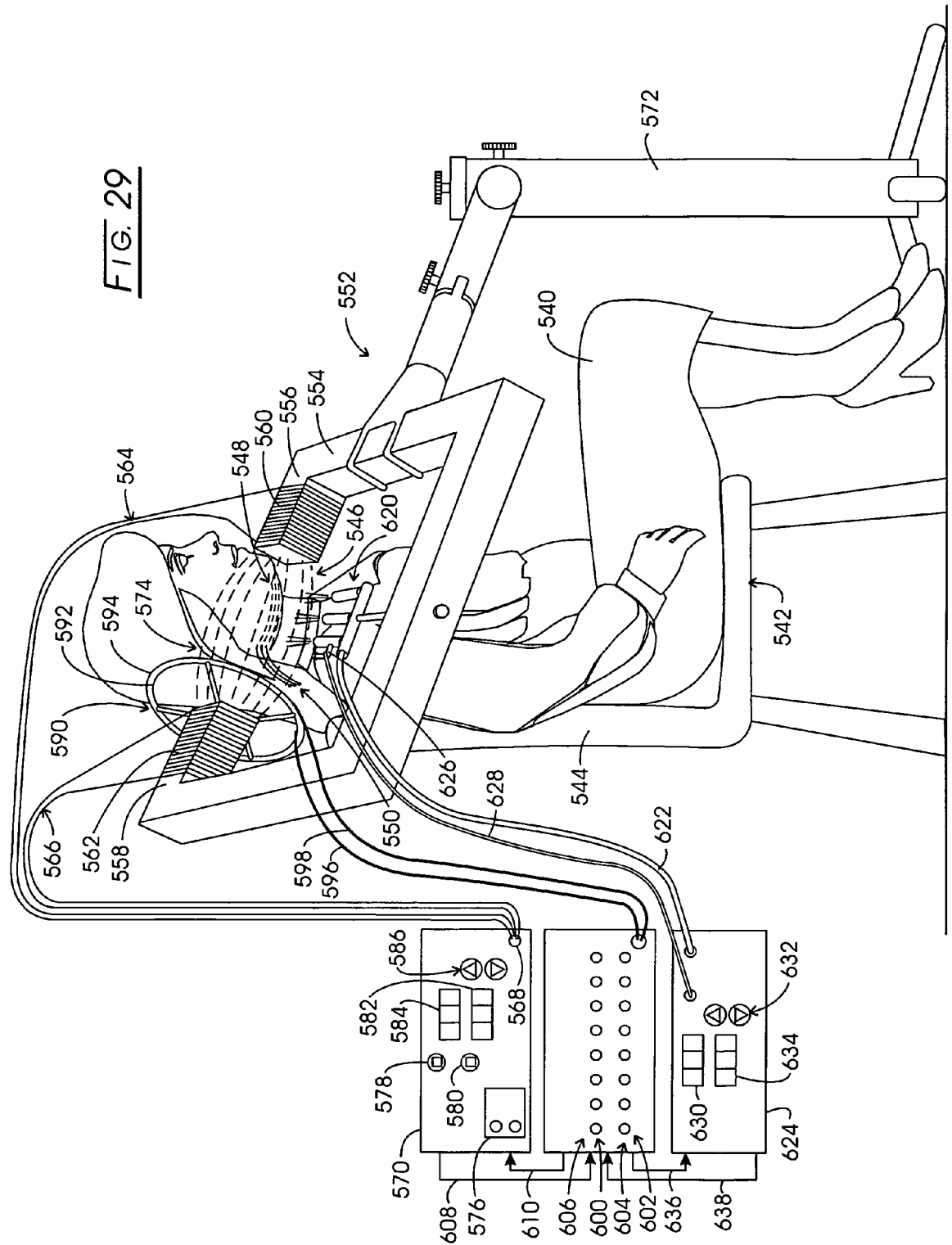
FIG. 29 is a schematic representation of the system wherein the ferrite-based temperature sensing and auto-regulating heater implants are employed.

Referring to FIG. 29, a system and procedure are illustrated wherein ferrite based heater implants and temperature sensors are employed, for example, in the manner discussed in FIG. 27 in conjunction with procedures predicated upon the discussion associated with FIG. 4. In the figure, a patient is represented at 540 seated upon a chair represented generally at 542, at least the back 544 of which is formed of an electrically insulative material. In treating skin laxities, the practitioner will determine a skin region for carrying out a controlled shrinkage of the collagen of the dermis. For instance, one such region is represented generally at 546. While not shown in the figure, a visually discernable matrix or pattern of dots may be located in regions as at 546 such that the instantaneous extent of shrinkage can be both visually and computationally analyzed. Within that region 546, the practitioner will determine the extent (percentage) of collagen shrinkage desired to achieve an improved facial contour and the amount of that shrinkage may be varied, for example, in terms of target/Curie temperature values. In this regard, as shrinkage occurs adjacent the borders of the defined region 546, less shrinkage may be desirable, thus lower temperatures may be employed. Generally, a determination is made as to the number and position of heating channels to be established within which the implants are to be positioned. This may be done with visibly discernable lines at the surface of the skin of the patient. Then, following the administration of a local anesthetic such as lidocaine, ferrite-based heater implants as well as temperature sensor implants, for example, as described in connection with FIG. 14 are implanted. Implantation is carried out utilizing elongate introducer needles which may be coupled with sutures such as described at 204 in FIG. 14. Other tethering approaches will occur to those skilled in the art, for instance bayonet joint technology. In the figure, a linear array of three such implants which are generally parallel to one another are represented in general and in phantom at 548, the sutures which were attached to the introducer needle being represented in general at 550. Patient 540 is then seated upon chair 542 and a magnetic field generating apparatus as represented generally at 552 is brought into operative position. Apparatus 552 is seen to be comprised of a flux conductive C-core having oppositely disposed spaced-apart legs 556 and 558 carrying respective inductive windings 560 and 562. The start/stop leads from winding 560 are represented in general at 564 while the corresponding start/stop leads associated with winding 562 are represented generally at 566. Leads 564 and 566 extend to connector 568 of an alternating current power supply. C-core 554 is retained in position by a support stand 572 in a manner wherein the magnetic flux path represented at dashed lines 574 is appropriately aligned. Power supply 570 is seen to incorporate an on/off switch assembly 576; a start therapy switch 578; a stop therapy switch 580; a display of the practitioner selected maximum therapeutic heating time 582; a display of the current cumulative therapeutic heating time 584; and an up/down switch 586 for selecting maximum heating time.

C-core 554 is constructed using a low-loss ferrite material suitable for operation in the frequency range from about 25 kHz to about 1,000 kHz, or preferably in a range from about 50 kHz to about 250 kHz. One such low-loss ferrite material is designated 3C94 and is manufactured by Ferroxcube/Philips of Sudbury, Mass.

Mounted adjacent C-core leg 558 is an implant interrogator antenna assemblage represented generally at 590. Assembly 590 includes an excitation antenna 592 which corresponds to antenna 302 described in connection with FIG. 19 and a sense antenna 594 which corresponds with antennae 308 of that figure. Cables 596 and 598 extend respectively from antenna 592 and 594 to a temperature sensor implant excitation and monitoring system represented generally at 600. System 600 is configured with an array of paired upper and lower lights, each pair representing the condition of a given temperature sensor implant within the array 548. In this regard, where a light is illuminated in the lower row shown generally at 604 then that illuminated light represents that the temperature sensor implant is at a monitoring temperature below target temperature. On the other hand, where a light within the upper row shown generally at 606 is illuminated, then the corresponding temperature sensor implant is indicating that the target temperature has been reached. As discussed above, that target temperature may be a lower threshold temperature while the autoregulating heater implant will reach a slightly higher upper limit temperature. As represented by arrows 608 and 610, the system 600 and control power supply 570 are interactive. In this regard, when the temperature sensing implant indicates that therapy temperatures have been reached, then timing can ensue and the current cumulative therapeutic heating time will be displayed at display 584.

It is important that the procedure cause no thermal damage to the epidermis. Accordingly, cooling fluid is directed to the surface of the skin from the 3-nozzle array represented generally at 620. Array 620 is mounted upon the C-core back leg and receives cooling fluid such as room temperature air which may be combined with a water mist from conduit 622 extending from a coolant control system represented in general at 624. Skin surface temperature input to system 624 is by an infrared temperature sensor 626 which is coupled via multi-lead cable 628 to system 624. The skin surface temperature measured by sensor 626 is displayed at 630 in system 624. A maximum allowable temperature value may be set within system 624 by up/down switches 632 which perform in concert with a display 634. System 624 interacts with system 600 as represented by arrows 636 and 638. In this regard, should the maximum temperature permitted be exceeded, the system will shut down a procedure.

The general procedure for carrying out temperature measurement with system 600 is intermittent wherein the magnetic field generating apparatus 552 is turned off and excitation antenna 592 is driven for a short interval sufficient to develop a resonant ring in the temperature sensing implant.

Then the excitation antenna 592 is turned off and sense antenna 594 is enabled. Such enablement will be for a short interval sufficient to detect the resonant center frequencies of the sensor implants as they resonate for a short interval. Field generating apparatus 552 then is turned on while the system 600 is turned off.

Figure 26:
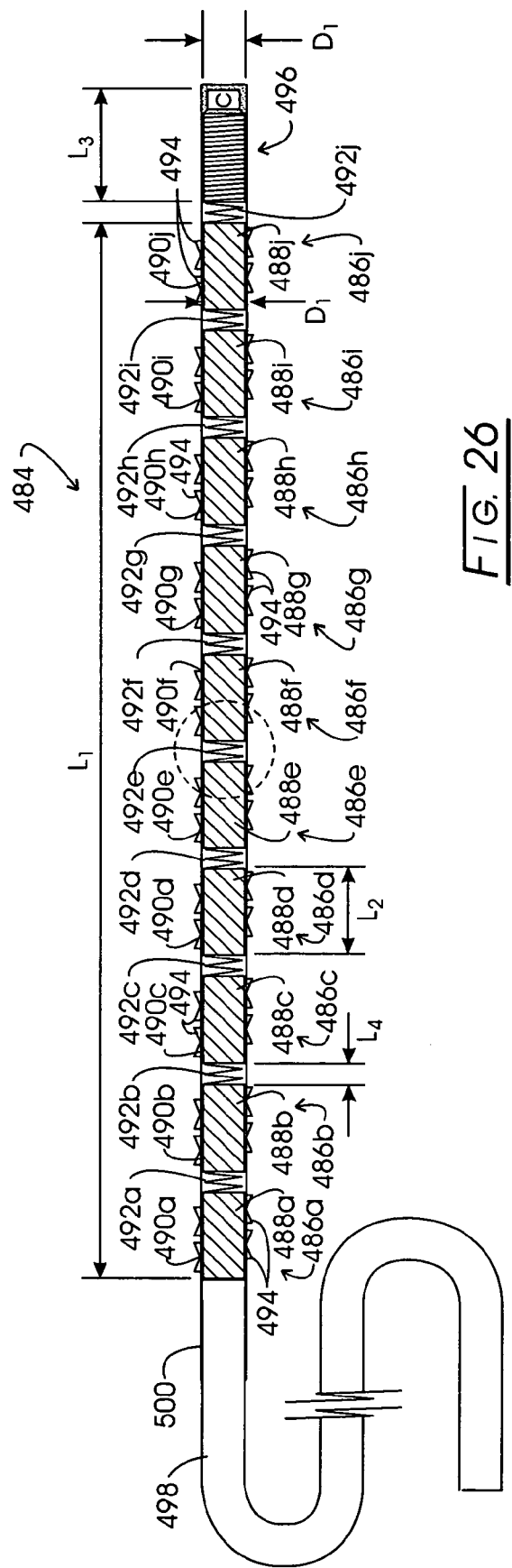
FIG. 26 is a schematic representation of a string-like linear array of ferrite-based auto-regulating implants and passive temperature sensor configured with barbed exteriors.

As an alternative arrangement, the passive temperature sensing implant can be positioned beneath the skin, for example, in between the linear array of heater components such as that described at FIG. 24 and FIG. 26. To be effective, such a temperature sensor implant should be arranged such that its core axis is generally parallel to the corresponding core axes of the ferrite-based heater components. Further, the passive temperature sensors may be attached to the surface of the skin rather than below the surface of the skin. Again, positioning will be such that the core axis of the temperature sensor is approximately parallel with the core axes of adjacent heater components. Temperature sensing may be accomplished with other temperature sensing approaches, for instance, one or more fiberoptic, thermocouple or thermistor sensors inserted into the tissue or placed on the surface of the tissue. Alternatively, infrared sensors as described at 626 may be employed for non-contact measurement of the surface temperature of the skin to determine the effectiveness of the tissue heating carried out by the implanted heater components.

FIGS. 30A-30D should be considered together in the manner labeled thereon. The figures provide a flow chart approach to the therapy associated with, for example, FIG. 29. Looking to FIG. 30A, the procedure is seen to commence at block 650 wherein the skin region which would be subject to collagen shrinkage is determined. Such a region has been described at 546 in FIG. 29. Next, as represented at line 652 and block 654, the practitioner determines the percentage extent of linear collagen shrinkage to be effected at the skin region as discussed in connection with FIG. 3. In order to develop a collagen fibril matrix or scaffold of adequate strength or persistence, that determination of percentage shrinkage should be about 20% or less. As the collagen shrinkage occurs at locations approaching the border of the elected skin region, the practitioner may want to lower the percentage of shrinkage to achieve what may be termed a "feathering" into unaffected skin to improve the resultant facial contour. Such a determination is represented at line 656 and block 658. Percentage of heating having been determined, then as represented at line 660 and block 662 the practitioner determines and marks heating channel locations at the noted region of skin which will be effective to achieve the determined shrinkage. Inasmuch as shrinkage may be observed by the practitioner during the procedure, some aid in evaluating the extent of shrinkage may be established by providing a pattern of imageable shrinkage evaluating indicia at the region. This, for example, may be a regular matrix pattern of water resistant but alcohol dissolvable ink dots. Accordingly, as represented at line 664 and block 666, a pattern of imageable shrinkage evaluating indicia at the region is provided. Recorded imaging such as digital imaging is optional. Next, as represented at line 668 and block 670, therapy temperature(s) and associated time interval(s) for the determined shrinkage percent(s) are determined. It may be recalled that this treatment time and temperature has been discussed in connection with FIG. 4. Protection of the epidermis then is considered as represented at line 672 and block 674 where a determination and setting of an upper bounded or limited maximum permissible skin surface temperature is made. To avoid skin surface (epidermis) injury, this setting likely will be from about 40° C. to about 42° C. Then, as represented at line 676 and block 678 (FIG. 30B) the practitioner selects flexible implants of ferrite-based heater components which will be self regulating about the predetermined temperature(s). As a component of this selection, as represented at line 680 and block 682 these selected heater implants may be combined with ferrite-based passive resonant temperature sensor implants as described above. These temperature sensor implants have resonant outputs of given intensity at monitor temperatures below the determined temperatures or target temperatures. The completed implant may be inserted by attachment or tethering to an introducer needle. Accordingly, as represented at line 684 and block 686 each combined implant is attached to or tethered to an introducer needle. Then, as represented at line 688 and block 690, a local anesthetic such as lidocaine or the like is administered at the skin region to be treated. Following such administration, as indicated at line 692 and block 694 introducer needles are employed to position the combined implants along the identified heating channel locations at a depth or depths suited for evolving a controlled transfer of thermal energy into the dermis while avoiding thermal damage to the subcutaneous fat layer. Location of the implants has been discussed in connection with FIGS. 27 and 28. Line 696 and block 694 provide for the application of a ferrite responsive magnetic field for the implants to commence the heating procedure. As this heating procedure ensues, the practitioner will want the opportunity to shut it down, for instance, by pressing a stop therapy button on a control console as described earlier at 580 in connection with FIG. 29. Accordingly, as represented at line 700 and block 702 a query is posed as to whether a stop therapy signal has been generated. In the event that it has, then as represented at line 704 and block 706 the procedure is terminated. In the event that such a signal has not been generated, then as represented at line 708 and block 710 skin surface temperature is monitored at the region of interest as described in connection with infrared temperature sensor 626 in FIG. 29. In conjunction with this monitoring and the excitation of the ferrite heater component, cooling fluid is applied to the skin region as represented at line 712 and block 714 (FIG. 30C). While this cooling is being carried out, as represented at line 716 and block 718 the cooling fluid flow rate may be modulated to maintain the skin surface temperature at the maximum or lower value established in connection with block 674. Next, as represented at line 720 and block 722 a query is made as to whether the skin temperature so monitored is greater than the maximum permissible temperature. In the event that it is above the maximum permissible temperature, then as represented at line 724 and block 726 the procedure is terminated. Where the skin temperature maximum permissible value is not succeeded, then as represented at line 728 and block 730 the passive resonant temperature sensors within the implant are monitored for a short interval while the ferrite responsive magnetic field is turned off. During this quiet sampling interval the temperature sensor excitation and monitoring system 600 is operated as discussed in connection with FIG. 29. With that sampling, as represented at line 732 and block 734 a query is posed as to whether the therapy temperature or target temperature(s) have been reached. In the event they have not, then as represented at line 736, the program loops to line 728. Where the target temperature has been reached, then as represented at line 738 and block 740, therapy timing is commenced. During this therapy interval, as represented at line 742 and block 744 (FIG. 30D) the practitioner monitors the shrinkage evaluating indicia as discussed in connection with block 666 for relative movement. As an option, this monitoring may be undertaken with digital imaging media which will record and display initial positions of the indicia as well as the relative movement of the indicia in the course of therapy.

This shrinkage monitoring and evaluation leads to the query posed as represented at line 746 and block 748 wherein a determination is made as to whether the predetermined extent of shrinkage has been reached. Where it has been reached, then as represented at line 750 and block 752, the procedure is terminated and, as indicated at line 754 and block 756 the implant(s) are removed. Subsequent to this completion of the therapy, as represented at line 758 and block 760 the practitioner will examine the patient at a later time to determine whether successful neocollagenesis has been achieved.

Returning to block 748, where the percentage extent of shrinkage as predetermined has not been reached, then as represented at line 762 and block 764, a query is posed as to whether the therapy time interval as predetermined has expired. In the event that it has, then as represented at line 766 and block 752, the procedure is terminated, the implants are removed and post therapy review for neocollagenesis is carried out. Where the query posed at block 764 indicates that the therapy time interval has not expired, then as represented at line 768 the program loops to line 742 leading to block 744 and the monitoring of the extent of shrinkage.

Figure 31:
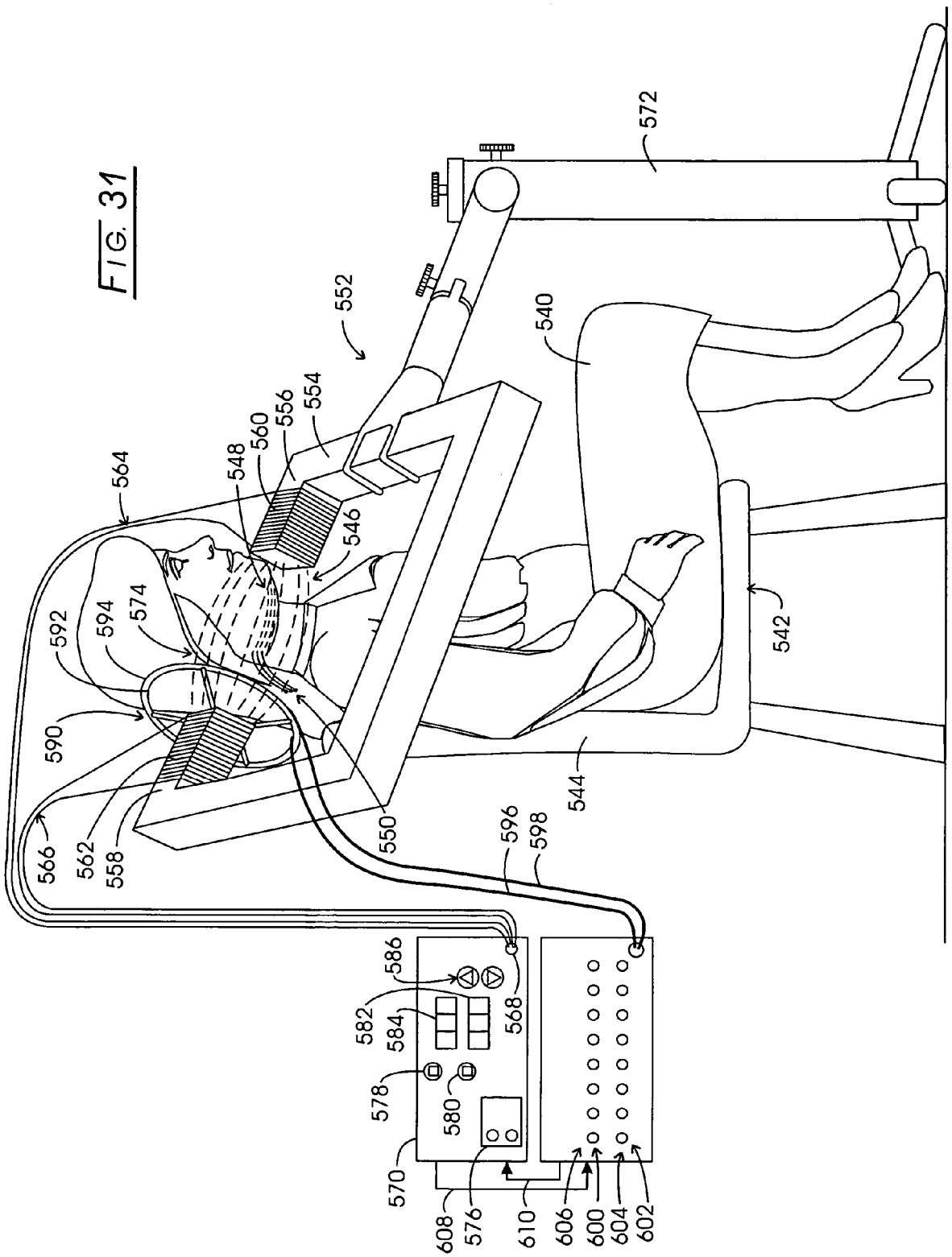
FIG. 31 is a schematic representation similar to FIG. 29 but not including the skin surface cooling feature.

Referring to FIG. 31, a therapy arrangement essentially identical to that at FIG. 29 is presented. Accordingly, where common elements are present they are identified with the same numeration as is present in FIG. 29. Note in the figure that there is no active control of the skin surface temperature. Earlier described cooling control system 624, 3-nozzle array 620 and infrared temperature sensor 626 are not present. While this approach is workable it is not recommended.

Figure 32:
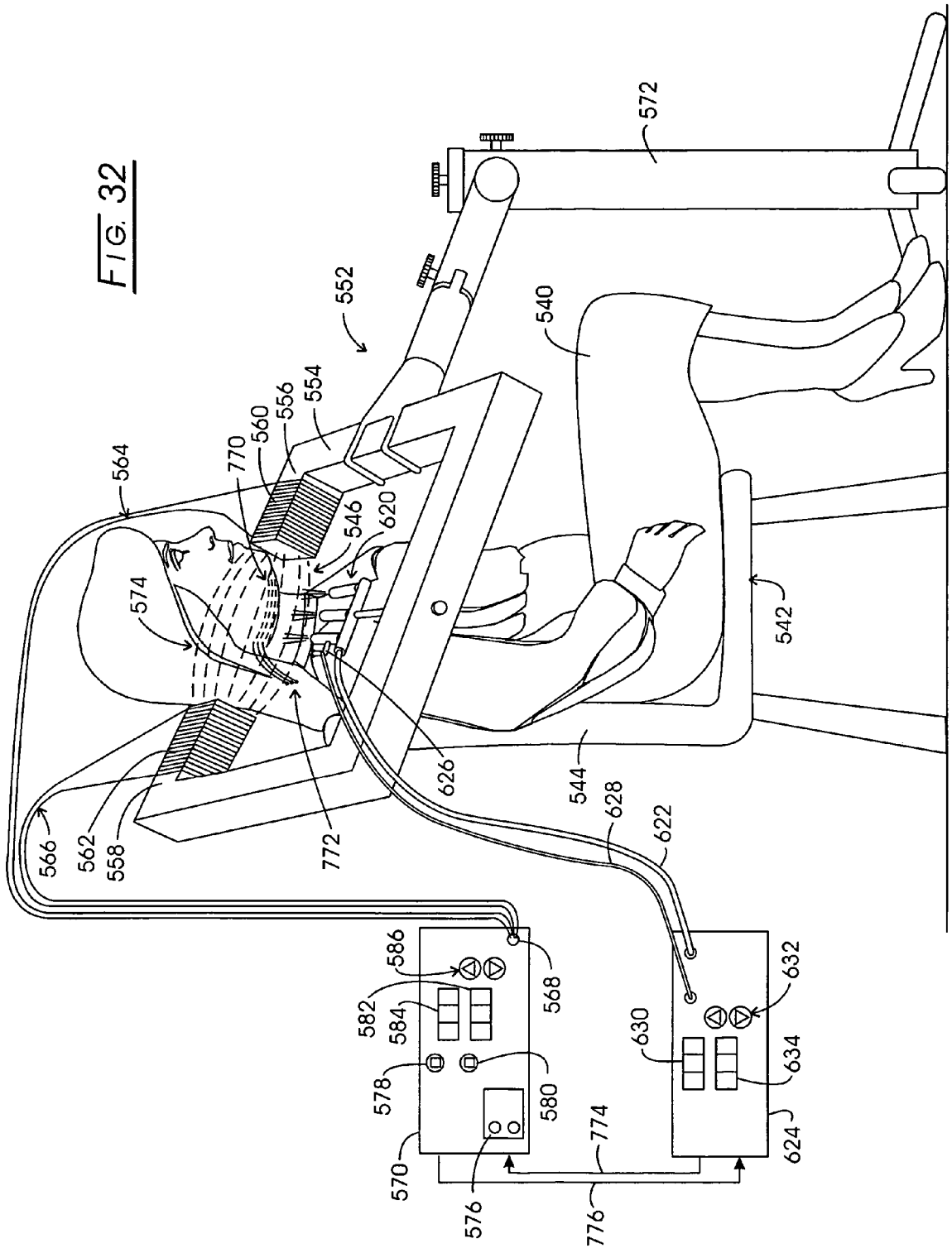
FIG. 32 is a schematic representation of the system of the invention similar to FIG. 29 but not including implants incorporating a passive ferrite-based temperature sensing component.

Referring to FIG. 32, a therapeutic procedure is illustrated which, in general, is identical to that described in connection with FIG. 29. Accordingly, where appropriate, the same identifying numeration is employed in the instant figure as with FIG. 29. However, with the instant approach, the ferrite-based temperature sensor implant components are not employed. Instead, the implants are formed of linear arrays of self regulating ferrite heater components as described, for example in connection with FIGS. 15 and 24. Accordingly, the temperature sensing system 600 described in FIG. 29 is not shown, however, the skin surface cooling 3-nozzle array remains in conjunction with its control 624. The array of linear implants now is represented at 770 while the implantment sutures are identified at 772. Skin surface cooling system 624 now is shown to be interactive with power supply 570 as represented at arrow 774 and 776. In this regard, the infrared skin surface temperature monitor 626 may provide a signal which may be extrapolated to determine the temperature at the heater array 770 inasmuch as the array 770 is quite close to the surface of the epidermis.

Referring to FIG. 33 an illustration of therapy procedure is presented wherein cooling fluid nozzle array 628, infrared skin surface temperature sensor 626 and coolant control system 624 remain. However, skin region 546 is configured with an array of electrically heated implants represented in general at 780. These implants may be provided as described in conjunction with FIGS. 7, 9, 10, and 11. The flexible implants of array 780 are shown having electrical leads represented generally at 782 which are electrically connected to a corresponding array of cables represented generally at 784. Each cable of array 784 is interconnected with one channel of a multichannel power supply 786. In this regard, three of the channel connectors are represented at 788-790. Temperature sensing data may be supplied to the power supply 786 to provide a temperature feedback control. In this regard, temperature sensors such as one or more thermocouples or the like positioned within an implant may be provided. Where resistant heating devices as described in FIG. 7 are employed, temperature may be monitored and controlled through resistance feedback control, e.g., by constructing heating elements within the flexible heater implants using electrically conductive material which has a large temperature coefficient of resistance (e.g., nickel, copper, platinum). Additionally, as described above, the infrared skin surface temperature sensor 626 may provide an output which can be extrapolated to determine heater implant temperature. Accordingly, an interactive association between cooling control system 624 and power supply 786 is represented by arrows 792 and 794. The infrared sensor and nozzle array 628 is seen supported from an arm 796 extending from a support pedestal 798.

The implants thus far described are located within dermis with somewhat elongate surgical needles. A suture is attached to the leading end of the flexible implant and extends to the trailing end of the surgical needle. Such surgical needles are currently employed to correct ptosis as described in publications Nos. 9 and 10 above and illustrated in connection with FIG. 1. For the above procedures a similar needle-based approach is utilized.

Looking to FIGS. 34 and 35, an introducer needle is represented generally at 810 which extends a distance, $L_n$, from its forward end point 812 to its trailing end shown generally at 814. Trailing end 814 is configured for attachment to a pull thread or suture, here such attachment is represented as an eyelet 816 to which is attached a schematically represented pull thread 818. In general, the length of these needles, $L_n$, will range from about 50 mm to about 500 mm and will fall within a preferred range of about 100 mm to 200 mm. The needle diameter, $D_n$, as seen in FIG. 35 will range from about 0.2 mm to about 3.0 mm and preferably will fall in a range of about 0.8 mm to about 1.5 mm. Other configurations of needles as at 810 will provide for a swageing attachment of the pull thread or suture 818 as opposed to an eyelet approach.

In the disclosure to follow the implants will be configured as one or more heater segments mounted upon a thin polymeric thermal barrier designed to protect the subcutaneous fat layer from thermal damage. These thermal barriers act as a support which, while flexible, are rigid in compression. This permits untethered implantment at the junction of dermis and subcutaneous fat without formation of an exit wound from within. Following therapy the implant is pulled from the introducer needle formed heating channel. Because of the physical-textural nature of dermis as compared to adjacent adipose tissue, preferably the needles aren't surgically sharp and may be somewhat uplifted during insertion. The heating channel to be thus formed will be comparatively wide.

Looking to FIGS. 36 and 37, an introducer needle which has been modified to accommodate the geometry of thermal barrier-based implant is represented generally at 820. The forward end represented generally at 822 is configured as a flat point and the device extends to a trailing end represented generally at 824. Trailing end 824 is configured with an eyelet 826. Needle 820 will exhibit a width, $W_m$, of from about 0.08 inch to about 0.15 inch and will be about 4 inches to about 10 inches long. The thickness of the needle, $T_m$, as seen in FIG. 37 will be from about 0.005 inch to about 0.030 inch. A suture 828 is seen extending from connection through eyelet 826, however, it is doubtful that such a component is required.

The width of the implant thermal barrier also can be accommodated for with an introducer needle configured with a bladed tip. Referring to FIGS. 38 and 39, such an introducer needle is represented generally at 830. As seen in FIG. 39, the body represented generally at 832 of needle 830 is of an elongate cylindrical configuration having a channel extending through it. The forward end of needle 830 as represented generally at 834 has received the shank portion 836 of a non-surgically sharpened blade 838. Body 832 is flattened at its forward end and the shank 836 of blade 838 is adhesively embedded. The flattened portion of the forward end is seen in FIG. 39 at 840. To facilitate its pulled removal from the heating channel which it formed, the protruding trailing edges of blade 838 are rounded over. Blade 838 will exhibit a maximum width of from about 0.10 inch to about 0.15 inch and the body portion 832 will exhibit a diameter, $D_n$, within a range of about 0.060 inch to about 0.080 inch. Of additional interest, end 834 of an introducer needle 830 is configured to carry a very small light emitting diode 842 having a light output in the red to blue spectral region. The light is energized from two leads 844 and 846 extending outwardly from the swaged trailing end of the needle as represented generally at 848. When in use, the illuminated LED 842 can be observed through the skin such that the practitioner is readily aware of the location of forward end 834. Additionally, variations of the depth of the needle from the skin surface can be observed as either a brightening or attenuation of the extent of brightness of red to blue light seen through the skin. In general, the tissue penetration capability depends upon wavelengths elected. Positioning of the leading ends of the introducer needles at the junction between dermis and the underlying fatty layer is facilitated by the nature of those tissues. In this regard, dermis is composed of collagen fibril which exhibits a density greater than the adipose tissue next to it. The practitioner will readily locate the tissue interface by tactile response.

Referring to FIG. 40, an initial embodiment of an implant incorporating a thermal barrier is represented generally at 860. Implant 860 is formed with a thin, flat and flexible polymeric support represented generally at 862. Adhesively mounted upon the support side 864 are eleven ferrite-based heater segments 866a-866k. To permit flexibility of implant 860 along its length, note that these heater segments are mutually spaced apart and extend between a leading end of support 862 represented generally at 868 and a trailing end represented generally at 870. An aperture or eyelet hole is illustrated at 872 to which is attached one end of a pull thread or suture 874. The opposite end of this pull thread is tied or swaged to the trailing end represented generally at 876 of an introducer needle represented generally at 878 which extends to a leading end represented generally at 880 which is pointed. Introducer needle 878 is seen to be configured in a manner of introducer needle 820 described in connection with FIGS. 36 and 37.

While implant 860 is illustrated as being tethered to introducer needle 878 such that both entrance and exit wounds would be formed, it needn't be. Device 860 may be both inserted and removed through an entrance wound. To facilitate these maneuvers adjacent the dermis, the interstices between adjacent heater segments 866a-866k may be filled with a biocompatible, flexible material such as a silicone.

FIG. 41 reveals that the heater segments 866a-866k exhibit a flat low profile with a generally rectangular periphery. FIG. 42 reveals a cross-section of segment 866a which is seen to be flat and rectangular incorporating a ferrite core 882 surmounted by a nonmagnetic metal sheath 884. In general, the flat ferrite core is about 0.4 mm thick; 2.5 mm wide; and 6 mm long. While these heater segments are mounted upon the support surface or side 864 of the support, the opposite surface is designated a "thermally insulated side" 886. A key benefit of this configuration resides in the ability to place the thermally insulated side in an orientation facing the subcutaneous fat layer adjacent the dermis thereby providing directional heating, i.e., outwardly and into the dermis. Correspondingly, heat flow to the subcutaneous fat layer will be minimized.

Support 870 may be formed of adhesively joined layers of electrically and thermally insulative polyimide film. For instance, this film is synthesized by polycondensation reaction between an aromatic dianhydride and an aromatic diamine and is marketed under the trade designation Kapton®. In general, five such polyamid films may be joined together, each having a thickness of 0.005 inch to provide a total thickness of about 0.025 inch. Preferably, support 870 is formed of a Kapton® substrate of 0.005 inch thickness upon the support surface of which segments 866a-866k are mounted. That substrate, in turn, is bonded at its oppositely disposed bonding surface to a polymeric thermal barrier support. The barrier support may be formed of a polymeric resin such as a polyetherimide available under the trade designation "Ulten" from the Plastics Division of General Electric Company of Pittsfield, Mass. Implant 860 may be coated with an electrically insulative biocompatible conformal layer such as the earlier-described Parylene.

The preferred embodiments of the implants of the instant system employ the polymeric thermal barrier in combination with one or more resistive heating segments located upon the support surface of the thermal barrier. Referring to FIGS. 43 and 44, such an implant carrying a single resistive heater segment is represented in general at 890. FIG. 44 reveals a cross-section of the elongate polymeric support represented generally at 892. Support 892 may be configured having a support side 894 spaced from a thermally insulative side 896 and may be configured with combined film layers of the earlier-described Kapton® which are adhesively adhered together. Preferably, support 892 is configured with a support surface substrate formed of Kapton® having a thickness of about 0.005 inch which is bonded to a polymeric thermal barrier support formed, for instance, of the above-described polyetherimide resin, "Ulten". FIG. 43 reveals a very thin copper resistive heating segment or element represented generally at 898. Element 898 is in the general shape of an elongate U extending between a leading end represented generally at 900 and a trailing end represented generally at 902. Electrical leads are seen at 904 and 906 extending from trailing end 902. Leading end 900 is seen to incorporate an attachment through-hole or aperture 908 through which a pull thread or suture may be attached for the less preferred implantment approach. Additionally, the leading end 902 may be configured to define a sharpened point as represented at 910. In general, the resistance exhibited by heater 898 should be about 4 ohms or greater at 20° C. and it should exhibit a temperature coefficient of resistance greater than about 0.0030 per degree centigrade.

Figure 46:
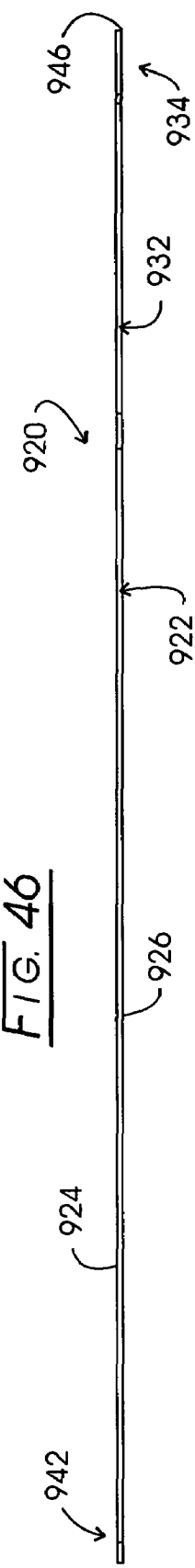
FIG. 46 is a side view of the implant of FIG. 45.
Figure 47:
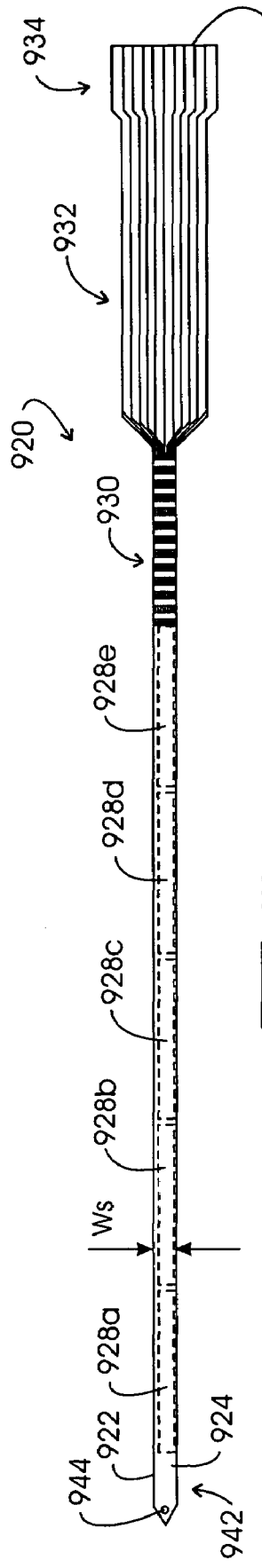
FIG. 47 is a top view of the implant of FIG. 45.
Figure 48:
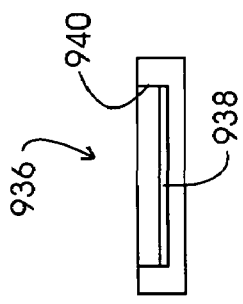
FIG. 48 is an end view of the polymeric connector component shown in FIG. 45.

Referring to FIGS. 45-47, a thermal barrier supported electrical resistance implemented implant is represented generally at 920. At a seen in FIGS. 45 and 46, device 920 is configured with a polymeric support represented generally at 922 having a support side 924 and an oppositely disposed thermally insulative side 926 as seen in FIG. 46. Support 922, as before, may be configured with a 0.005 inch thick Kapton® substrate, the outward surface of which provides the support side 924. That substrate may be combined with four generally identical Kapton® layers which are adhered together. Preferably the Kapton® substrate is bonded to a polymeric thermal barrier support formed for instance of the above-described "Ulten" material. For a physical embodiment, the overall length of the support is about seven inches and its width, $W_s$, will be about 0.110 inch. Support surface 924 carries five resistive heater segments 928*a*-928*e*. In FIGS. 45 and 47, these segments are identified by rectangular dashed boundaries having a widthwise extent of 0.100 inch segment 928*a* has a length of 0.798 inch while each of the remaining segments have a length of about 0.8 inch. Dashed boundaries illustrate the five identified segments inasmuch as for the scale represented in these figures, magnification would be required to observe the elements forming the individual segments. The segments are formed of copper having a thickness of between about 0.0005 inch and about 0.0015 inch. They are electrically addressed by an initial lead region represented generally at 930 confined within the width, $W_s$, which then transitions to an expanded feed region represented generally at 932. Region 932 again is expanded at an electrical contact region seen in FIG. 47 at 934. Region 934 is seen in FIG. 48 as being supported by a polymeric connector component 936. An end of component 936 as seen in FIG. 48. The device is configured with a forward slot 938 and an electrical contact access opening 940. The leading end of device 920 is pointed, having an included angle with the range of about 45° to about 70° and, as seen in FIGS. 45 and 47 is configured with a hole or aperture 944 utilized for optional attachment of a pull thread or suture. However, that approach to implantation is not preferred.

Implant 920 is coated with a biocompatible electrically insulative conformal layer, for instance, the earlier described Parylene which extends from the forward region 942 to a location slightly spaced inwardly from the rearward edge 946. Such inward spacing may, for example, be about 0.25 inch.

Figure 49:
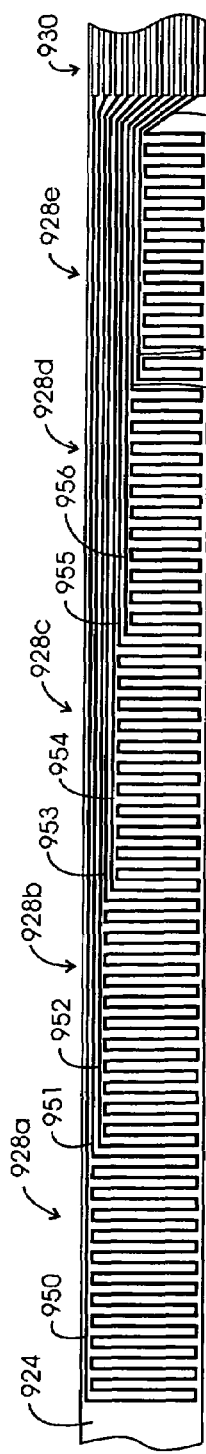
FIG. 49 is a schematic representation of a portion of an implant similar to that of FIG. 45 and showing the lead topology associated with isolated heater segments.

Heater segments 928*a*-928*e* may be configured with different circuit topologies. Referring to FIG. 49, the general location of each of the heater segments 928*a*-928*e* again is represented. In these drawings, such segments are represented somewhat schematically as lines in the interest of clarity. Each segment is addressed by what may be considered input and output leads. In this regard, segment 928*a* is configured with leads 950 and 951 which extend to lead region 930 along one edge of the device. Heater segment 928*b* is coupled with leads 952 and 953. Heater segment 928*c* is connected with leads 954 and 955. Heater segment 928*d* is connected with leads 956 and 957; and, segment 928*e* is coupled with leads 958 and 959. Within the heater region the resistance elements will exhibit a line width of about 0.003 inch and a spacing of about 0.003 inch. Within lead region 930 the lead width or line width will be about 0.010 inch with a spacing of about 0.003 inch. Within the expanded lead region 932 (FIGS. 45, 47 and 53) the leads 950-959 will expand in width, for example, to a line width of about 0.035 inch and a spacing of about 0.003 inch. Within the contact region 934 the heater leads expand in width to about 0.040 inch with a spacing at about 0.005 inch. These values are exemplary and will vary among implant designs. However, the topology demonstrated in the figure is one wherein the leads are isolated as they extend from each of the heater segments.

Figure 50:
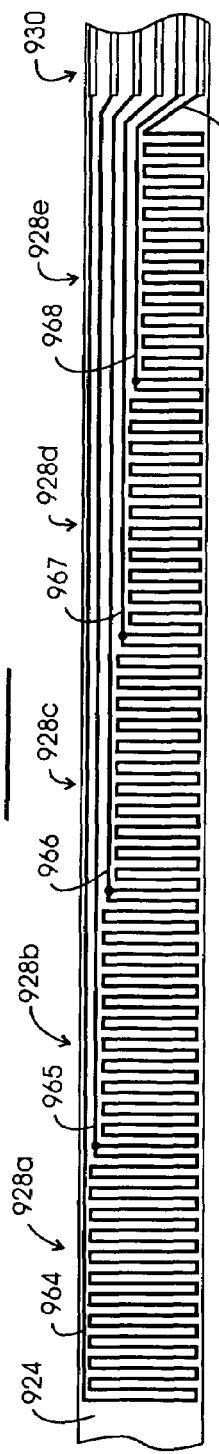
FIG. 50 is a partial schematic view of a heater implant similar to that shown in FIG. 45 but illustrating a shared lead topology.

Referring to FIG. 50 a shared lead topology is represented. Again, heater segments 928*a*-928*e* are identified in general. Heater segment 928*a* is coupled with leads 964 and 965. Heater segment 928*b* is coupled with leads 965 and 966. Heater segment 928*c* is coupled with leads 966 and 967. Heater segment 928*d* is coupled with leads 967 and 968; and heater segment 928*e* is coupled with leads 968 and 969. This shared arrangement results in six leads within lead region 930, lead 969, in effect, being common to all segments. For this shared topology, the expanded width leads in region 930 will, for example, have a lead width of about 0.020 inch with a spacing of about 0.003 inch. Within the expanded lead region 932 (FIGS. 45, 47) the lead or line width may be about 0.035 inch with a spacing of about 0.003 inch.

Figure 51:
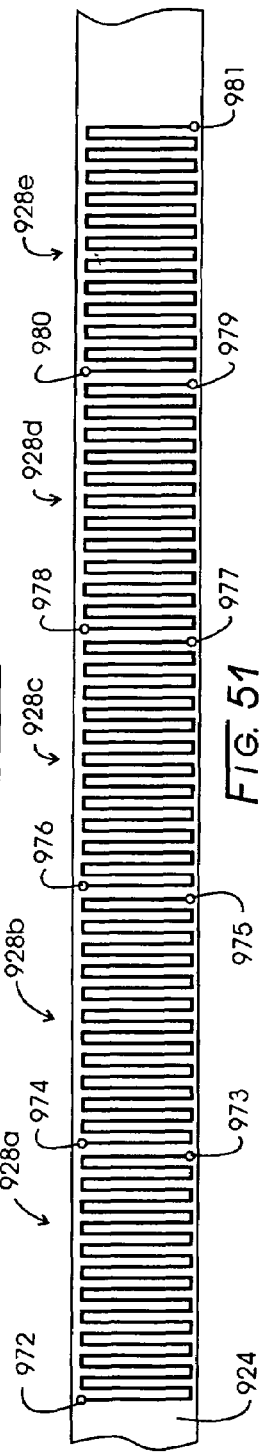
FIG. 51 is a top view of an implant similar to that shown in FIG. 45 showing isolated heater segments developed with a multilayer construction.
Figure 52:
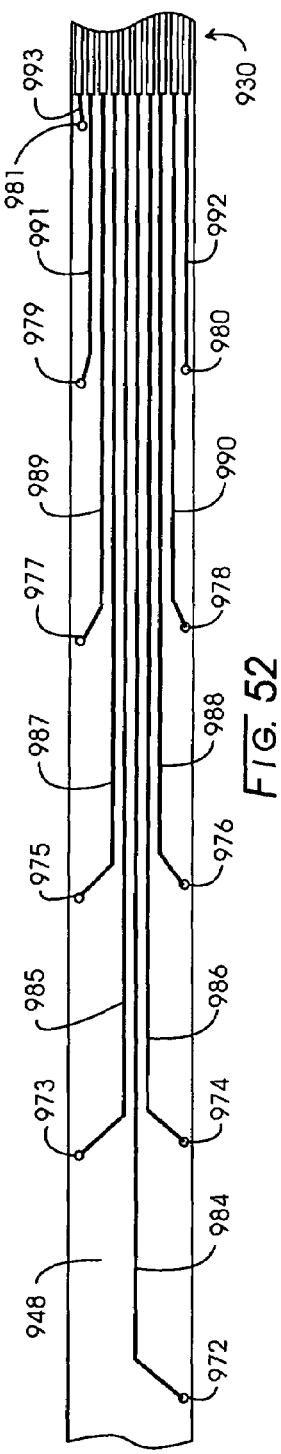
FIG. 52 is a schematic representation of the bottom of the implant of FIG. 51.

Referring to FIGS. 51 and 52, a topology providing for isolated heater segments developed with a multilayer construction is schematically portrayed. Heater segments 928*a*-928*e* again are represented in general as they are supported upon a support surface provided by a substrate formed of the above-described Kapton® having a thickness of about 0.005 inch. Heater segment 928*a* is seen to extend between via 972 and via 973. Heater segment 928*b* is seen to extend between via 974 and via 975. Heater segment 928*c* extends between via 976 and via 977. Heater segment 928*d* extends from via 978 to via 979; and heater segment 928*e* extends from via 980 to via 981. For the instant topology, while the heater segments are formed on the support side 924 of the substrate, the leads extending to these isolated segments are formed upon its back side or surface 948. Looking to FIG. 52, side 948 is shown in conjunction with vias 972-981. Heater segment 928*a* is coupled with leads 984 and 985 extending from electrical connection through respective vias 972 and 973. Heater segment 928*b* is coupled with leads 986 and 987 extending from respective vias 974 and 975. Heater segment 928*c* is coupled with leads 988 and 989 extending from respective vias 976 and 977. Heater segment 928*d* is coupled with leads 990 and 991 extending from respective vias 978 and 979; and heater segment 928*e* is coupled with leads 992 and 993 extending from respective vias 980 and 981. Following the formation of the leads 984-993, side 948 is adhesively bonded to a polymeric thermal barrier support formed of material such as the above-described "Ulten" polyetherimide resin.

Figure 53:
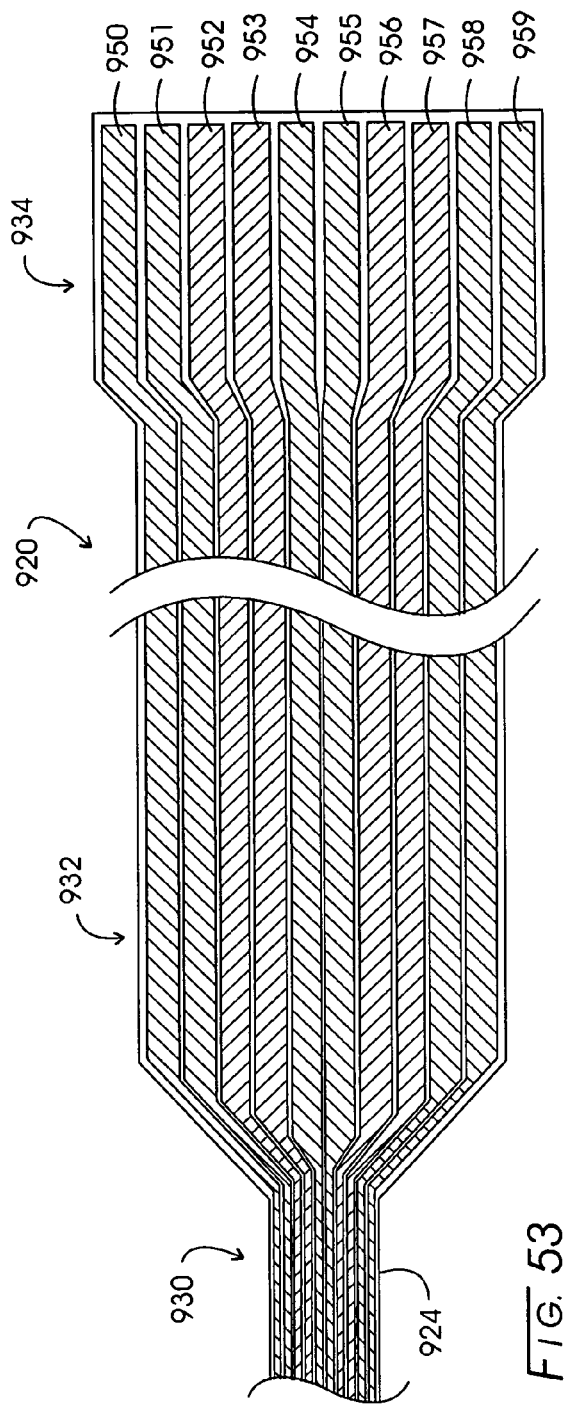
FIG. 53 is a broken away enlarged view of the leader topology of the implant described in connection with FIGS. 45 and 49.
Figure 54:
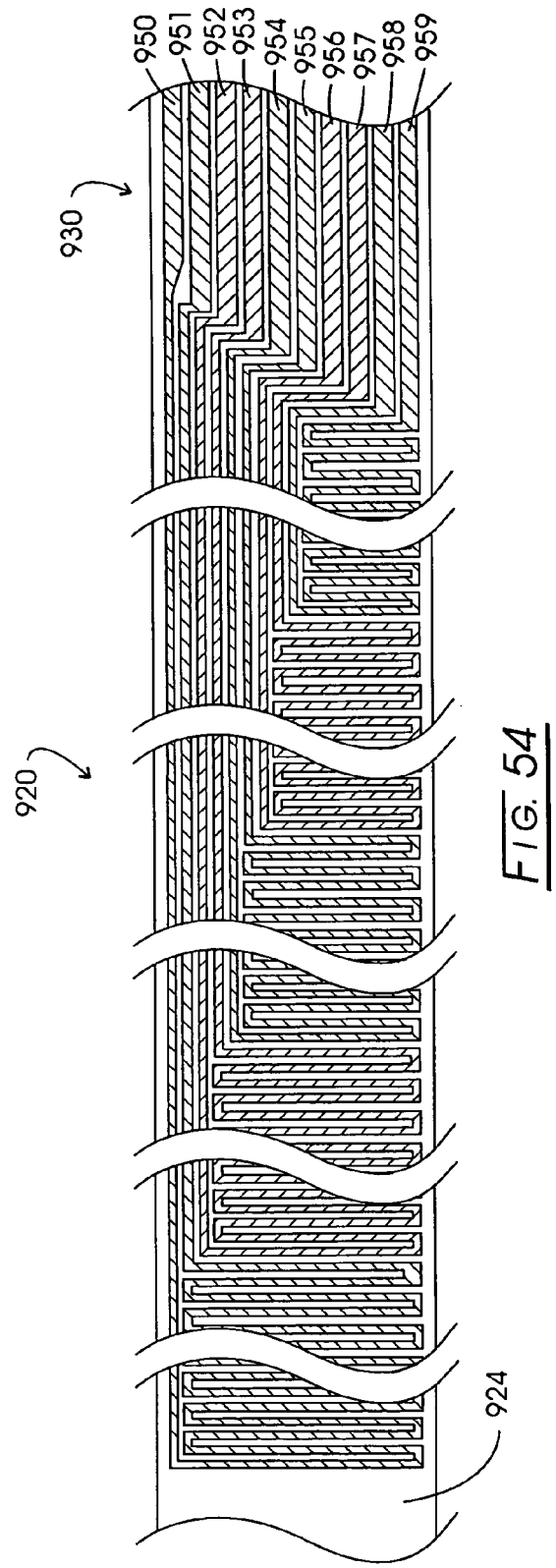
FIG. 54 is a highly enlarged view of the heater segment region and portions of the lead region of the implant of FIG. 53.

Referring to FIG. 53 a substantially enlarged view of regions 930, 932 and 934 of implant 920 is provided. The figure is a representation of the lead topography shown schematically in FIG. 49 but now illustrated as it would actually appear under substantial magnification. Leads 950-959 are again identified. Looking to FIG. 54, an even greater magnification of the heater segment region and lead region 930 is presented. Again, the geometry associated with leads 950-959 is revealed in this partial view.

Thermal barrier-based implants as at 920 can be located in thermal relationship along a heating channel by establishing the heating channel with an introducer needle which is tethered by a pull thread or suture to the leading end of the implant and then drawing the implant into that needle established channel. This approach to locating the implant necessarily involves the formation of not only an entrance wound but an exit wound into the skin. Looking to FIG. 55, an assemblage is shown generally at 1000 wherein an implant as at 920 is tethered to an introducer needle represented generally at 1002. Needle 1002, for instance, may be provided as described earlier at 820 in connection with FIG. 36 or at 830 as described in connection with FIG. 38. A pull thread or suture form of tether is schematically represented at 1004. The leading end 942 of the implant 920, for the instant embodiment, is seen to be configured with a bladed tip represented generally at 1006. Looking additionally to FIG. 57 the bladed tip 1006 is formed with a surgically sharp steel tip component 1008 which is adhesively attached to polymeric support 922 which is terminated at its forward end as represented at dashed end boundary 1010. Tip component 1008 may also be formed with a non-surgically sharp edge, for example, formed of type 304 stainless steel. Reinforcement of attachment of the blade may be provided by so positioning the aperture 944 that it passes both through the support 922 and the stainless steel blade 1008.

Avoidance of an exit wound when locating the implant as at 920 represents a preferable approach. With this approach, the elongate introducer needles are employed to create a heating channel adjacent the underside of the dermis. Once this channel is formed, the introducer needle is removed and the implant is inserted in a manner wherein its support side carrying one or more heater segments is in general contact with the dermis and is facing away from the subcutaneous fat layer.

The polymeric heater segment and thermal barrier architecture of the instant implant embodiment is somewhat ideal for this preferred method of implantation. While the polymeric support will readily flex along its length extent, it is quite strong in compression where its longitudinal edges are restrained from excessive flexure. This is the case inasmuch as the introducer needle preformed heating channel will retain the polymeric support in a fixed orientation of flexure while the practitioner's hand controls flexure outside of the entrance wound.

Looking to FIGS. 58-60, an untethered implant 920 is illustrated. The leading end 942 of the implant is seen to be configured with a bladed tip shown generally at 1016 which has no tethering aperture as earlier described at 944. However, the tip 1016 is formed with a non-surgically sharpened tip component 1018 as seen in FIGS. 59 and 60 which extends over the polymeric support 922 and is adhesively attached thereto. As before, the end of support 922 is represented by dashed edge 1020.

Where an appropriate introducer needle is employed to form a heating channel, the polymeric structure of the implant alone is sufficiently rigid for insertion within the channel. For such configuration, no sharpened tip component is required. Referring to FIG. 61, a pointed tip 1021 of implant 920 is depicted. Tip 1021 has no "sharpness" and is slideably insertable within a pre-formed heating channel.

Figure 64:
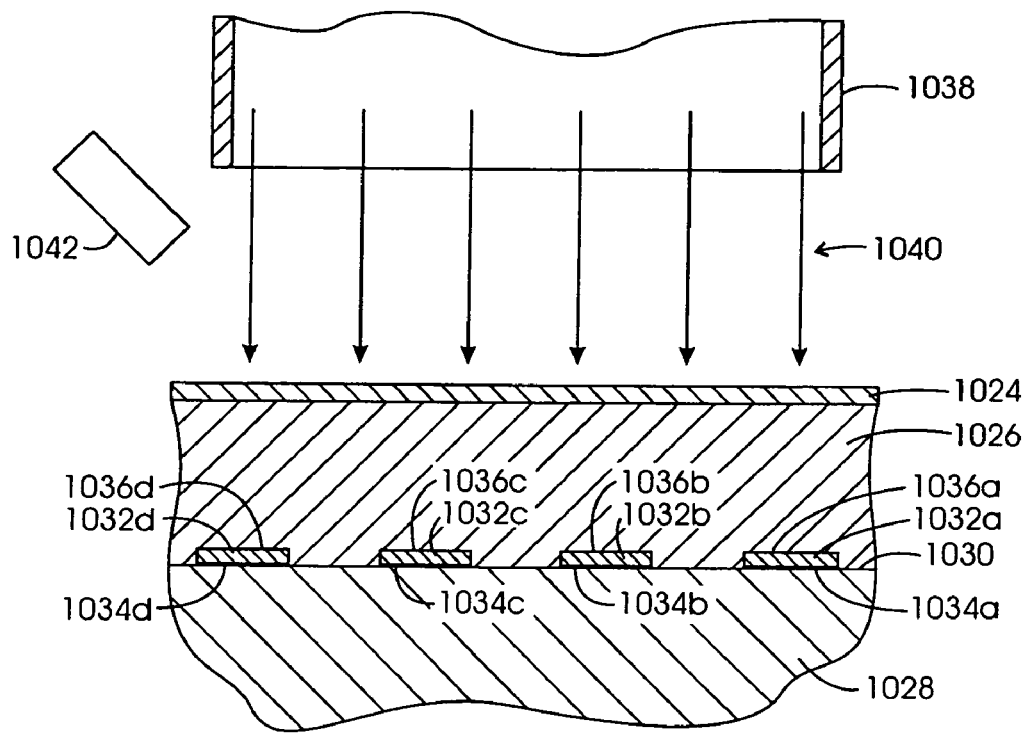
FIG. 64 is a schematic representation of implants as shown in FIG. 60 as they are embedded within a skin and subcutaneous fat structure, the figure additionally showing passage of cooling fluid against the skin surface and the monitoring of skin surface temperatures.

Looking to FIG. 62, tip 1022 of implant 920 is seen to be "rounded off" to facilitate insertion within a pre-formed heating channel. Inasmuch as the preferred location of these implants is at the interface of the dermis and next adjacent (fat) subcutaneous tissue it is beneficial for the implant tips to be slightly tapered from the thermally insulative side 926 toward the support side 924. During insertion of the implant, this taper tends to mechanically bias the implant against the inner boundary of the dermis, i.e., a "sleding" effect is evoked. Looking to FIG. 63, this tapered tip is schematically revealed. A Kapton® substrate carrying heater segments is seen at 945 adhesively bonded at 947 to the top surface of polymeric thermal barrier support 944. The tip 1023 of support 949 is seen to be configured with the above-discussed taper. Turning to FIG. 64, a schematic representation of the instant implants within their formed heating channel is schematically represented. In the figure, epidermis is represented at 1024 extending over dermis 1026 which, in turn, extends over subcutaneous fat 1028. The junction between fat 1028 and the dermis 1026 is schematically represented at 1030. Implant cross-sections are shown at 1032a-1032d. As thus implanted, the thermally insulative sides of these devices are respectively represented at 1034a-1034d, while their respective support sides are shown at 1036a-1036d. A source of cooling fluid is represented generally at 1038 blowing fluid comprised of gas such as air which may optionally include a misting fluid such as water at the surface of epidermis 1024. Such cooling flow is represented by the arrow array 1040. While the skin surface is cooled as represented at array 1040, its temperature is monitored, for instance, with an infrared temperature sensor as represented schematically in the figure at 1042. Particularly for the preferred approach to locating the implants with a single entrance wound, the polymeric support thickness should be from about 0.020 inch to about 0.040 inch.

A preferred control over heater segments as at 928a-928b is one which is based upon an intermittent measurement of heater segment resistance. Such resistance, exhibited while the implant has been positioned adjacent the dermis will be of a value developed in correspondence with an auto-calibration procedure. That procedure is carried out while the implants are imbedded, skin surface cooling is carried out and skin surface temperature monitoring is carried out as discussed in connection with FIG. 64.

Before any of the heating segments are energized but while they are in the circumstance represented at FIG. 64, then there is a predetermined initial Heater Segment Temperature, $T_{HS,to}$, based on an algorithm related to the measured Skin Surface Temperature, $T_{skin,to}$ $$T_{HS,to} = f(T_{skin,to}) \qquad (4)$$

That algorithm is associated with a controller by being preprogrammed into it. For example, if measured Skin Surface Temperature, $T_{skin,to}$ is 33° C., the $T_{HS,to}$ may be computed to be 35.5° C. for all heater segments. The treatment or target temperature (i.e., the Heater Segment Temperature) throughout the entire treatment interval or period, $T_{HS,t}$ is predetermined and fixed within the controller, for example, $T_{HS,t}$ for all Heater Segments may be established at 70.5° C.

Once the auto-calibration button on the controller is pushed, the following procedure is carried out:

a. The controller measures the resistance of each heater segment preferably employing a low-current DC resistance measurement to prevent current induced heating of the subject heater segment to obtain, $R_{HSi,to}$ where i=1 to 50 Heater Segments or more.

b. Since the heater is metal having a well-known, consistent and large temperature coefficient of resistance, α having a value preferably greater than 3000 ppm/° C. (a preferred valve is 3800 ppm/° C.), then the target resistance for each Heater Segment, $R_{HSi,target}$ can be calculated using the relationship:

$$R_{HSi,target} = R_{HSi,to}(1 + \alpha^*(T_{HS,t} - T_{HS,to})) \qquad (5)$$

where:

$R_{HSi,to}$=measured resistance of Heater Segment, i at imputed temperature of Heater Segment under skin, $T_{HS,to}$ α=temperature coefficient of resistance of heater element.

$T_{HS,t}$=fixed treatment temperature (i.e., target heater temperature).

$T_{HS,to}$=Imputed temperature of Heater Segments while residing under skin and prior to start of any heating of them.

c. As an assumption-based example, the following parameters are selected:

α=5,000 ppm/° C. (known)

$T_{HS,to}$=35.5° C. (imputed based on measured skin temperature)

$R_{HSi,to}$=10 ohms (for i=1, Heater Segment No. 1)

$T_{HSt}$=70.5° C.

Then:

$R_{HSi,target} = R_{HSi,to}(1 + \alpha(T_{HS,t} - T_{HS,to}))$
=10 ohms (1+0.005 (70.5−35.5))
=10 ohms (1+0.005 (35.0))
=11.75 ohms d. Hence, for Heater Segment No. 1 of a given implant, the controller will use the target resistance value of 11.75 ohms to control power delivery until the Heater Segment under measurement produces a resistance of 11.75 ohms. An approach to carrying out the heating of the Heater Segments to their target temperatures is to provide for intermittent temperature measurement utilizing the above approach.

Figure 65:
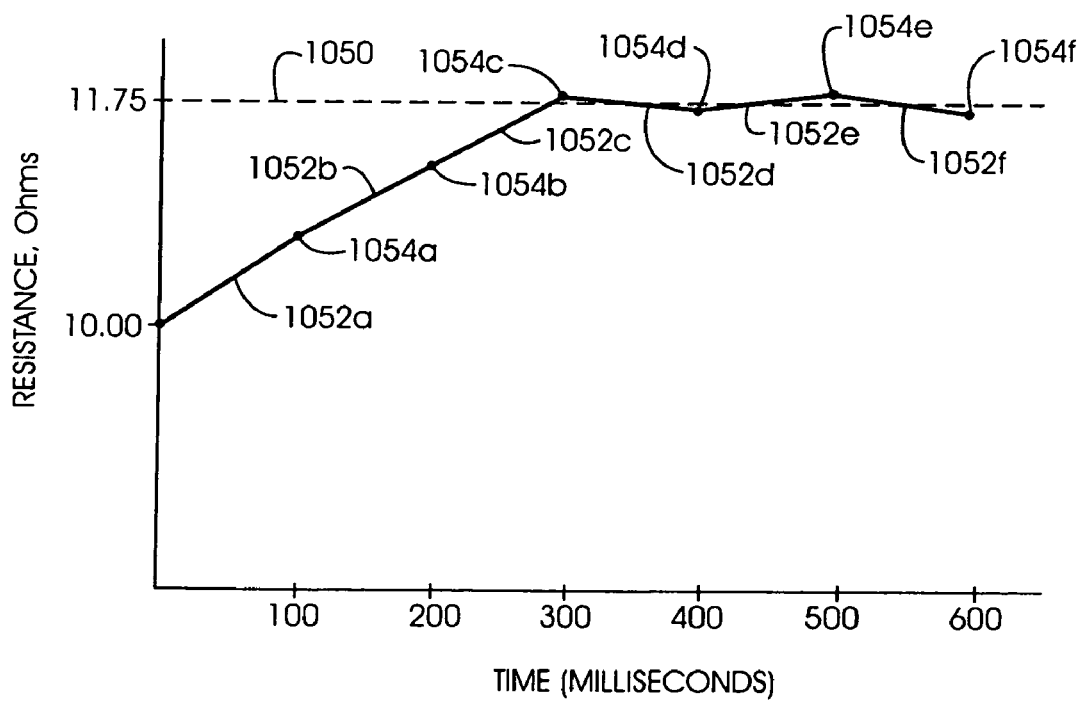
FIG. 65 is a plot relating heater segment resistance measurements with time.
Figure 66A:
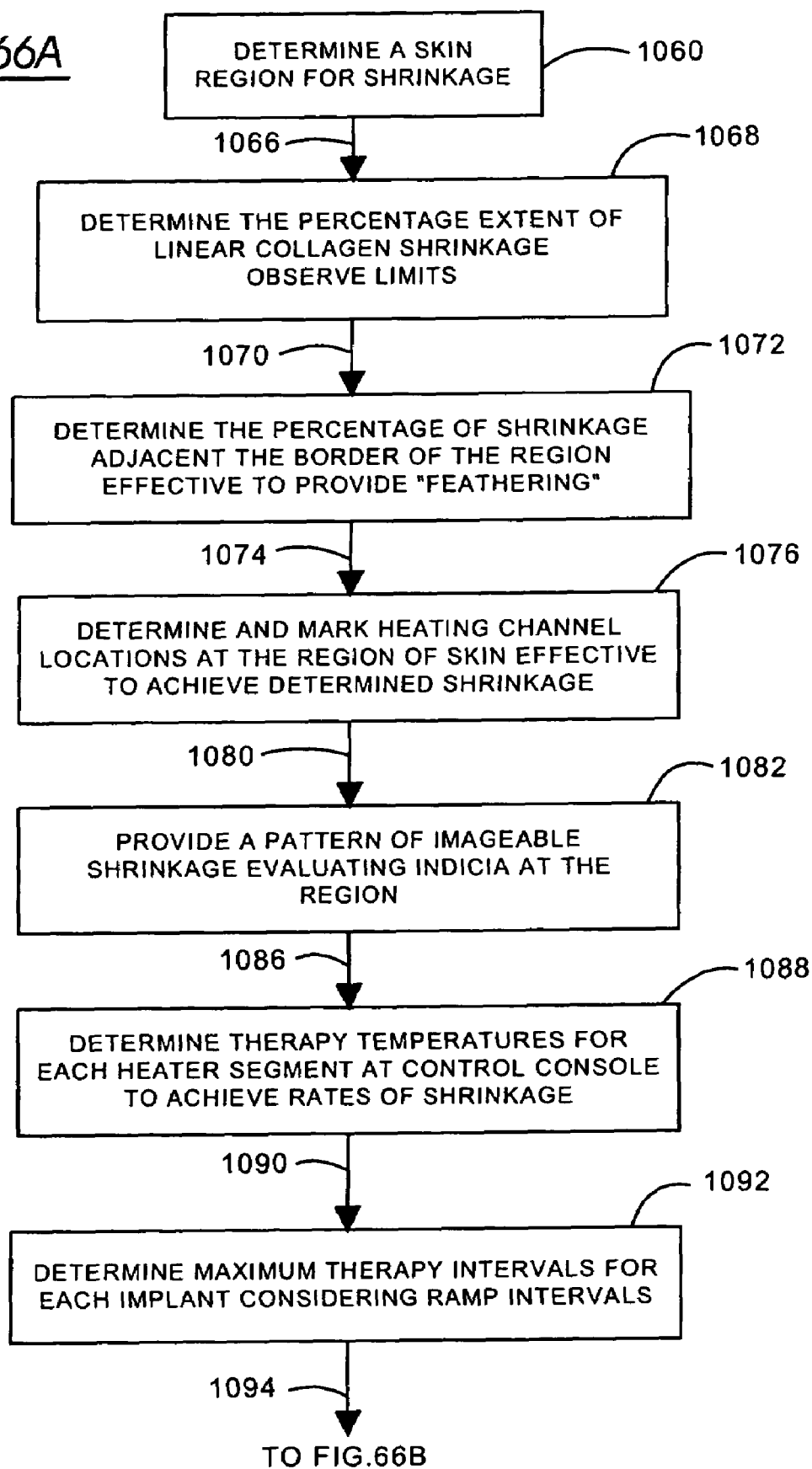

Looking to FIG. 65, the target resistance in ohms, for example, at 11.75 ohms is represented at dashed level 1050. Assuming that application of current to a heater segment occurs at time zero when the segment will exhibit a resistance of 10 ohms, then with the application of current the heater segment will commence to be heated, for example, for an interval of about 100 milliseconds as represented at heating curve component 1052a. Notice that the resistance is ramping toward level 1050 at the termination of a 100 millisecond heating interval, as represented at sampling interval component 1054a, resistance is measured for an interval of about 1 millisecond. Following that sampling interval, as represented at curve component 1052b current again is applied to the heater segment for a 100 millisecond interval, whereupon, as represented at sampling interval 1054b resistance again is measured and will have a higher value as it approaches level 1050. Following that sampling interval, as represented at curve component 1052c resistance will have ramped to the target level 1050 and slightly exceeded it during a heating interval of another 100 milliseconds. Next, as represented at sampling interval component 1054c, a determination is made that the target level 1050 has been slightly exceeded. Therefore, as represented at 100 millisecond heating curve component 1052d, no power is supplied to the heater segment and resistance drops just below the target level 1050, whereupon another sampling interval is carried out as represented at 1054d based upon that slightly lower resistance, current again is applied to the heater segment for a 100 millisecond interval as represented at heating curve component 1052e which ramps slightly upwardly for 100 milliseconds whereupon sampling interval 1054e will indicate that the target level 1050 again has been exceeded. Accordingly, no current is applied to the subject heater segment for the next 100 millisecond interval as represented at curve component 1052f, whereupon at the termination of the 100 millisecond interval, as represented at sampling interval 1054f measured resistance will be slightly below the target resistance value at level 1050.

The above control performs under the following conditions:

If $R_{HSi,t} < R_{HSi,target}$, then power is applied for a next heating interval of time δt.

Applied voltage can be reduced as this target temperature of the heater segment is approached to minimize overshoot.

Figure 2:
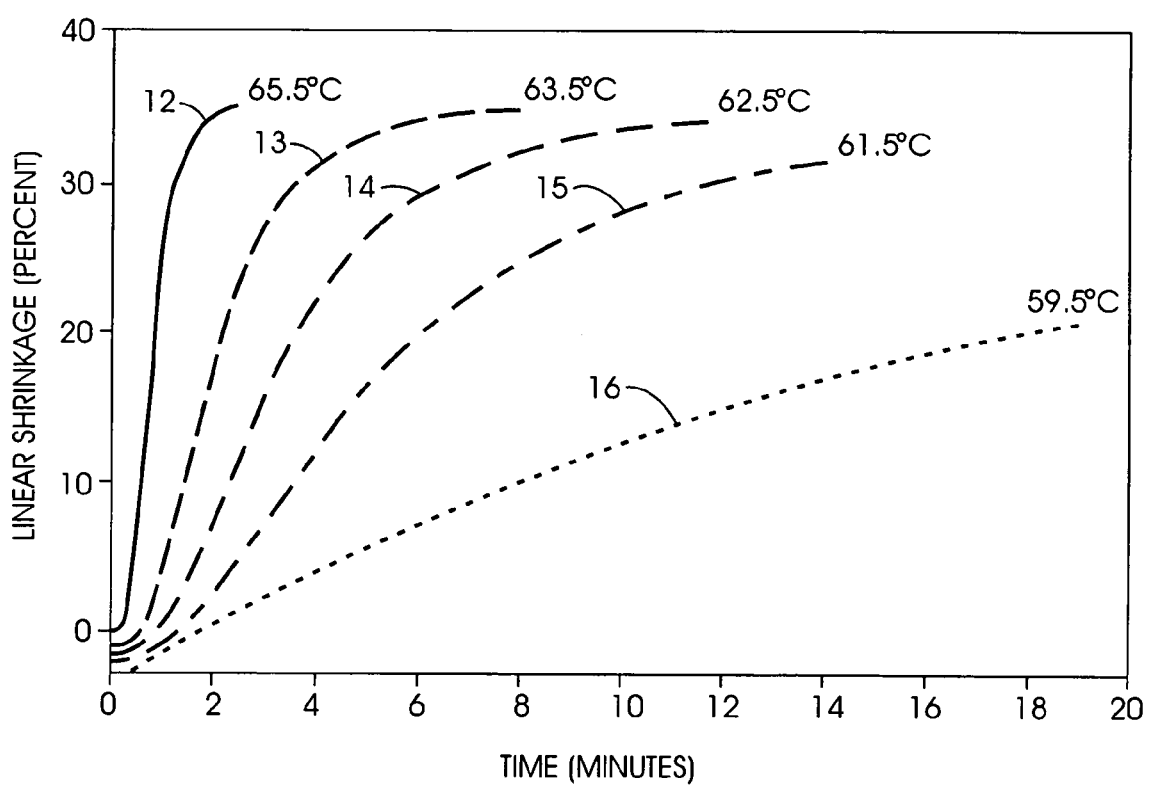
FIG. 2 is a family of curves relating linear shrinkage of dermis with time and temperature.
Figure 67:
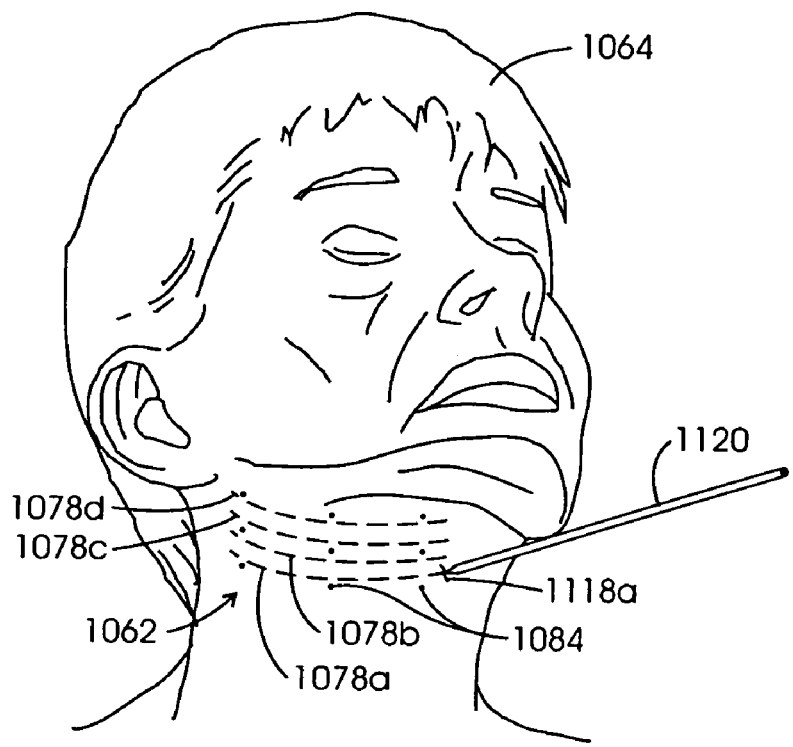
FIG. 67 is a perspective schematic representation of a human head and neck region showing the location of heater channels, indicia patterns and an introducer needle.

FIGS. 66A-66F combine to provide a flow chart describing the utilization of thermal barrier-based heater implants. The figures should be considered together as labeled thereon. Looking to FIG. 66A, the procedure commences with block 1060 providing for a determination of the region of the patient's skin selected for carrying out a collagen shrinkage at the dermis. Referring additionally to FIG. 67, such a region is represented in general at 1062 with respect to patient 1064. As represented at line 1066 and block 1068 in FIG. 66A, a determination is made as to the maximum average percentage extent of linear collagen shrinkage which is to be carried out. As discussed in connection with FIGS. 1-4, the amount of shrinkage should not be excessive so as to assure the development of a collagen matrix having tensile strength integrity effective to support neocollagenisis. As an example, about a 25% linear shrinkage may be elected. As part of this shrinkage determination, and as represented at line 1070 and block 1072 the practitioner may consider an aspect of "feathering" to reduce shrinkage at the border of region 1062. Accordingly, a determination may be made for the percentage of shrinkage adjacent that border. Inasmuch as the heater implants are formed with multiple heater segments, temperature values and/or heating duration at target temperature may be considered. Upon determining the extent of shrinkage, as represented at line 1074 and block 1076 the locations of the heating channels within the elected regions are determined and marked. As seen in FIG. 67, a marking of such heating channel locations is represented at 1078a-1078d. As represented at line 1080 and block 1082 a pattern of imageable shrinkage evaluating indicia may be located at the region. In FIG. 67 certain of these indicia are shown as dots 1084. This pattern of dots may be observed by the practitioner during the course of the procedure to establish and observe the extent of shrinkage. An advantage of the multiple heater segment architecture as described at 928a-928e in connection with FIGS. 45-47 is that each such segment may produce a unique or different target temperature. Accordingly, as represented at line 1086 and block 1088 in FIG. 66A the therapy temperatures may be determined for each heater segment at a control console to achieve different rates of shrinkage. This effect is observable from FIG. 2 showing that the temperature of the segment determines rate of shrinkage.

Figure 68:
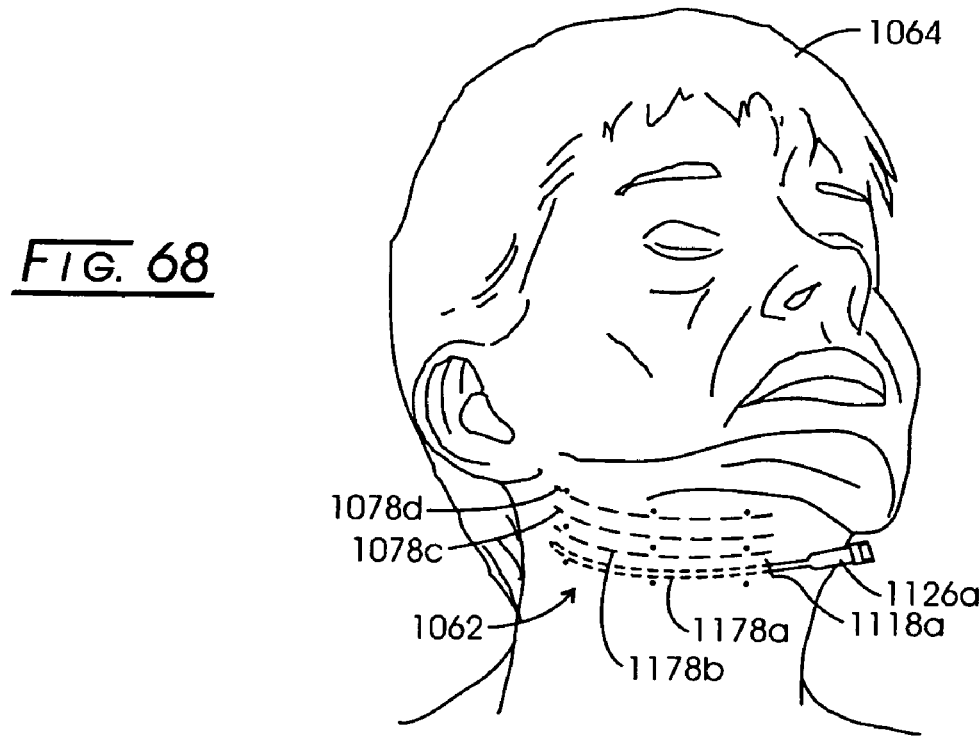
FIG. 68 is a schematic representation of the human head and neck region shown in FIG. 67 and showing the positioning of a thermal barrier/electrical heater segment-based implant installed within a heater channel.

In concert with the determination of therapy temperatures, as represented at line 1090 and block 1092 the practitioner determines and sets the maximum therapy intervals for each implant. In determining these intervals, the heating effect during ramp-up to the target temperature as well as ramping down should be considered. Such ramping is represented in terms of resistance in connection with FIG. 52. Next, as represented at line 1094 and block 1096 (FIG. 66B) the practitioner determines and sets bounded maximum permissible skin region surface temperatures. This determination is to avoid skin surface injury and more than likely will be set with upper limits from about 40° C. to about 42° C. The procedure continues with line 1098 and block 1100 providing for the selection of those thermal barrier based implants with their associated lead topology to be employed within the region as at 1062. Lead topology has been discussed in connection with FIGS. 49-52. Once selected, as represented at line 1102 and block 1104 implants may be plugged into cables from the controller such that an automatic test will be carried out for circuit continuity. While this same test will be carried out when the cables are connected following placement of the implants, the practitioner may wish to carry out this test before implantation. Next, as represented at line 1106 and block 1108 a local anesthetic (for instance, epinephrine) is administered to the patient. As represented at line 1110 and block 1112 the practitioner selects one or more introducer needles having widths which correspond with the widthwise extent of the active region of the thermal barrier based implant. This will result in an incision adjacent the dermis and above the layer of subcutaneous fat which will be wide as compared to the channel formed by a conventional cylindrical needle. The widened incisional channel functions, inter alia, to support the implant against excessive flexure about its widthwise extent. However, it has been determined that an introducer needle may not be required, a bladed implant being capable of forming the heating channel as it is inserted. Next, as represented at line 1114 and block 1116, for each heating channel, using a scalpel, the practitioner forms an entrance opening in the skin providing access to the interface between dermis and subcutaneous fat. /that incision may be about 2.5 mm wide and about 3.0 mm deep. Using the selected introducer needle, the heating channel is formed along the marked heating channel location. In FIG. 67, such an incision is represented at 1118*a* and the selected introducer needle is represented at 1120. Generally, the practitioner will apply a slight outward pressure upon the introducer needle 1120 to assure maintenance of the channel depth at the dermis-subcutaneous fat interface. Upon forming the channel, as represented at line 1122 and block 1124 the active region of each implant is inserted within the needle-formed heating channel in an orientation wherein the heater segments face outwardly, i.e., away from the subcutaneous fat layer. Looking momentarily to FIG. 68, implant 1126*a* is shown positioned within the heating channel marked at 1078*a* and through the small incision 1118*a*. Note that there is no exit wound, the implant 1126*a* being sufficiently rigid to position manually.

Upon locating the implants for therapy, as represented at line 1128 and block 1130, cables from the controller are electrically coupled with each heater segment for each implant through the utilization of removable connectors. Looking momentarily to FIG. 69, patient 1064 reappears and entrance incisions 1118*a*-1118*d* are seen with the active regions of implants 1126*a*-1126*d* inserted therethrough and into the associated heating channel. Connector components 1132*a*-1132*d* have been coupled to the electrical contact region of each implant. It may be recalled that the electrical contact region has been described in FIGS. 45 and 47 at 934 and that the connector has been described in FIGS. 45 and 48 at 936. For the isolated heater segment embodiment as described in conjunction with FIG. 49, two leads extend to each heater segment for a five heater segment embodiment described, for example, in FIGS. 45-47. While four such connectors are shown, ten channels are made available to drive a corresponding ten implants and thus, an additional six connectors are made available as represented by the dotted sequence of connectors 1132*e*-1132*j* extending from a cabling harness arrangement represented generally at 1134.

Returning to FIG. 66B, as represented at line 1140 and block 1142, an infrared temperature sensor is positioned at the region 1062. Such positioning may be aided by guiding light emitting diode "pointer" light. The IR temperature sensing arrangement is seen in general at 1144 in FIG. 69. While not shown in that figure, the control and monitoring of the temperature sensing arrangement 1144 is carried out from a control system represented in the figure by a control console shown generally at 1146. Console 1146 is seen to be configured with ten channels, the cable terminals of which are represented generally at 1148 and are numbered 1-10. Above each of these numbered cable connectors for each channel there is a columnar array of manually adjustable heat level switches represented at 1150*a*-1150*j*. Above each of the switch arrays 1150*a*-1150*j* there is located a light emitting diode shown respectively at 1151*a*-1151*j* which is energized to produce a red spectrum cue showing that all segments of that particular heater segment array have been de-energized. The arrayed switches may be adjusted by the practitioner to set an off (O) position; a low temperature position (L); a medium temperature position (M); and a high temperature position (H). The temperature values represented by these positions preferably are established by the system manufacturer. An on/off switch is represented at 1152 above which is located a light emitting diode which emits a green light when the system is turned on. Adjacent switch 1152 is a button-type auto-calibration switch 1156 above which a light emitting diode 1158 is located having an output in the yellow spectrum when the auto-calibration procedure discussed above is underway. Adjacent switch 1156 is a button-type start therapy switch 1160 above which is a light emitting diode 1162.

Diode 1162 emits in the green spectral region during therapy. A liquid crystal display is shown at 1164. Display 1164 publishes prompts to the practitioner during setup and therapy procedures.

Treatment duration is set with an up/down switch pair represented generally at 1168. Switch pair 1168 operates in concert with a three digit treatment duration display 1170 and a channel select arrangement comprised of an up/down switch pair represented generally at 1172 which performs in conjunction with a channel select display 1174. For each channel, where a treatment duration is selected, that selection may be entered by pressing the button-type enter switch 1176. When all target temperatures have been reached a green light emitting diode 1178 is energized and the elapsed time at target temperature is displayed at three digit display 1180. The setting of maximum permissible skin region surface temperature is carried out with up/down switch pair represented generally at 1182. Switch pair 1182 performs in conjunction with a three digit display 1184. Entry of the temperature selected with switch pair 1182 is made with button-type switch 1186. In the event a skin over-temperature is detected with temperature sensor 1144, then a cue is provided with the energization of a red region light emitting diode 1188.

The practitioner may stop the therapy while in progress by pushing button-type switch 1190. When that switch is so actuated, then a light emitting diode 1192 is energized to provide a red light output. Adjacent switch 1190 is a vertical array of light emitting diodes which may generate light in the red region. These diodes include a cable fault cue 1194; an auto-calibration fault cue 1196; an elected percentage shrinkage reached cue 1198; and a maximum therapy interval reached cue 1200. Energization of one of these latter cues may be accompanied by a prompt to the operator at display 1164.

Figure 69:
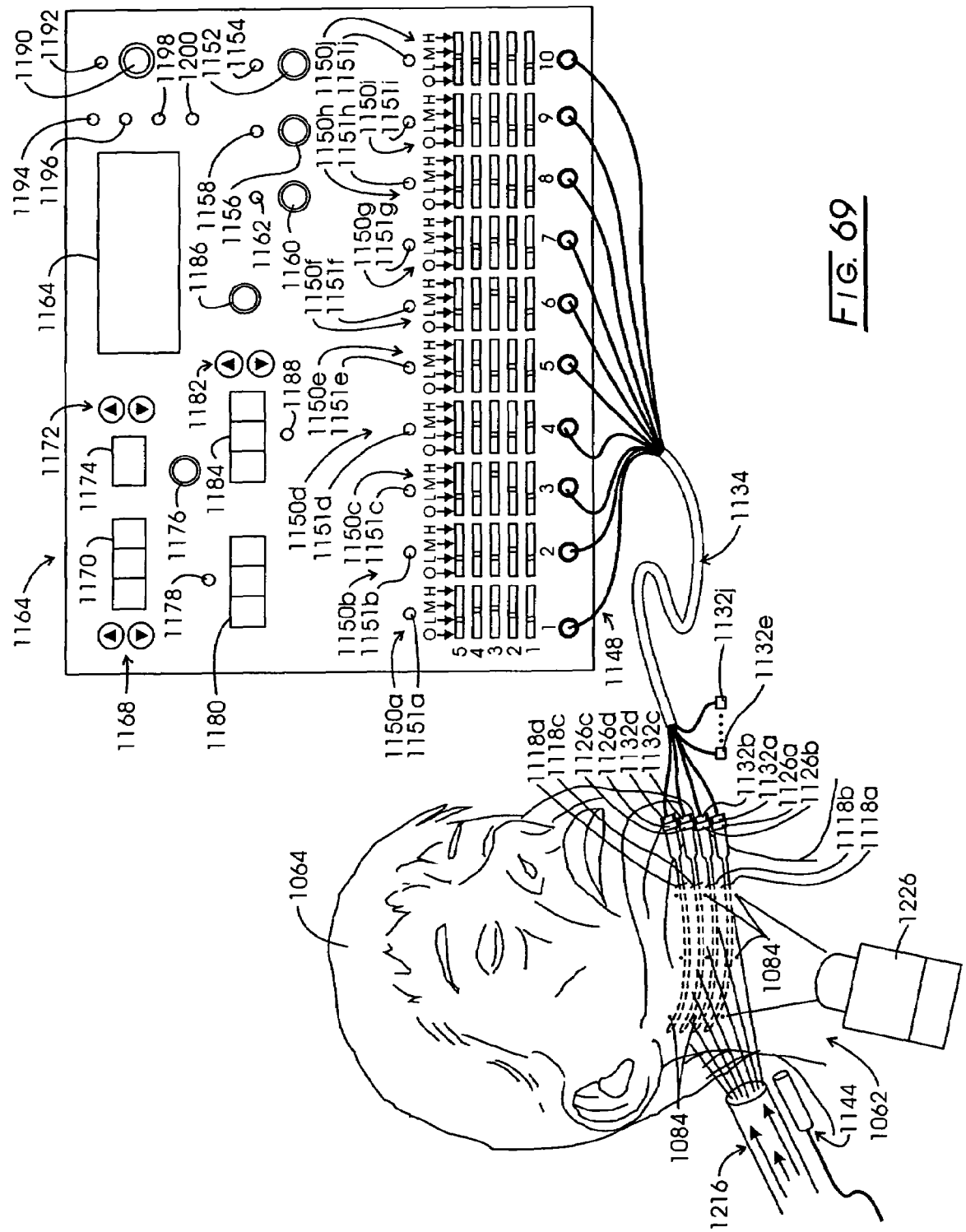
FIG. 69 is a schematic representation of the system and method of the invention utilizing thermal barrier and electrical heater segment-based implants.

Returning to FIG. 66B, as represented at line 1202 and block 1204 (FIG. 63C) a query is posed as to whether all cables are securely connected to the controller 1146 and to the heater segment leads. In the event they are not, then as represented at line 1206 and block 1208 the operator is cued with red LED 1194 and prompted at display 1164 to recheck the connection of cables. The program then loops as represented at line 1210 extending to line 1202.

Where all cables are appropriately connected, then as represented at line 1212 and block 1214 cooling fluid flow is directed toward the skin region 1062 from a cooling system represented generally at 1216 in FIG. 69. At this juncture in the procedure, the practitioner may observe the initial position of the shrinkage evaluating indicia within the region, for example, as represented by the pattern of dots, certain of which have been identified at 1084. This observation is represented in FIG. 66C at line 1218 and block 1220. As an optional arrangement, as represented by line 1222 extending to block 1224 a pattern of indicia such as dots 1084 may be digitally imaged and positionally recorded as start or initial positions. Such a digital imaging device is shown in FIG. 69 at 1226.

Returning to FIG. 66C, the program continues as represented by line 1228 extending to block 1230. At block 1230, auto-calibration is started with the operator actuation of switch 1156 and the energization of yellow cueing light emitting diode 1158. Following software-based computation, as represented at line 1232 and block 1234 the computed resistance values as have been discussed in connection with FIG. 65 are submitted to memory. The program then continues as represented at line 1236 and block 1238 where a query is posed as to whether auto-calibration has been successfully completed. In the event that it has not, then as represented at line 1240 and block 1242, light emitting diode 1196 is illuminated and the program continues as represented at line 1244 and block 1246 to provide a prompt at display 1164 calling for the rechecking of connections of cables to the controller and the replacement of any faulty implant. The program then loops as represented at line 1248 which extends to line 1232 resulting in a retest.

Where the query posed at block 1238 results in an affirmative determination, then as represented by line 1250 and block 1252 (FIG. 66D), treatment is initiated by pressing button-type start switch 1160 with the resulting illumination of light emitting diode 1162. Therapy having been initiated, the program then proceeds as represented at line 1254 and block 1256. As illustrated in connection with FIG. 62, temperature sampling is carried out every 10 to 100 milliseconds for about a 1 millisecond sampling interval for each heater segment. Additionally, as represented at line 1258 and block 1260, temperature sampling utilizing the infrared skin surface temperature sensor 1144 commences. In this regard, with the information or data thus gleaned, as represented at line 1262 and block 1264, the control system may modulate the flow rate of cooling fluid to maintain the skin surface temperature at a predetermined level or a level below a maximum value. Next, as represented at line 1266 and block 1268 a query is made as to whether the stop therapy button-type switch 1190 has been actuated. In the event that it has, light emitting diode 1192 is energized and as represented at line 1270 and block 1272 the procedure is terminated. Where the stop therapy button-type switch has not been actuated, then as represented at line 1274 and block 1276, the practitioner may observe the indicia pattern within the subject skin region 1062 to note the progress of collagen shrinkage at the dermis. Line 1278 extends to an option represented at block 1280 wherein an imaging system as at 1226 shown in FIG. 66 may display both the initial and the instantaneous positions of shrinkage evaluating indicia to determine the extent of shrinkage. The program then may continue as represented at dashed line 1282 and block 1284 (FIG. 66E). At block 1284, a query is made as to whether all heater segment target temperatures have been reached. In the event they have not, then as represented by loop line 1286 extending to line 1282, the system dwells until those target temperatures are reached. Where the query posed at block 1284 results in an affirmative determination, then as represented at line 1288 and block 1290, therapy timing is commenced. In FIG. 69, the reaching of target temperatures is cued by the illumination of light emitting diode 1178 and a timer displaying the elapsed time at such target temperatures is published at display 1180. Next, as represented at line 1292 and block 1294 a query is made as to whether the skin surface temperature as measured with sensing system 1144 is greater than the maximum limiting temperature, $T_{MAX}$. Where it is not less than that temperature, then as represented at line 1296 and block 1298, the procedure is terminated with an attendant cue to the practitioner represented by the energization of red light emitting diode 1188 (FIG. 69). Where skin temperatures are below the maximum limit, then as represented at line 1300 and block 1302, a query is posed as to whether the operator or practitioner has turned off the heater segment, for example, by manipulating one of the switches in the vertically arrayed switches 1150a-1150j. In the event of such a de-energization, then as represented at line 1304 and block 1306 the system terminates the energization of that selected segment. When the query posed at block 1302 results in a negative determination, then as represented at line 1308 and block 1310 a query is made as to whether the maximum average percentage extent of linear shrinkage has been reached. In the event of an affirmative determination, then as represented at line 1312 and block 1314 the procedure is terminated. As described in connection with FIG. 69, light emitting diode 1198 is illuminated to provide a red lighted cue. Where the noted percentage of extent of shrinkage has not been reached, then as represented at line 1316 and block 1318 (FIG. 66F) a query is posed as to whether the maximum therapy interval for a given implant has been completed. In the event of an affirmative determination, then as represented at line 1320 and block 1322 the implant is de-energized and, as represented at line 1324 and block 1326 the operator is cued by the illumination of a light emitting diode within the array 1151a-1151j as described in connection with FIG. 69.

Returning to block 1318, where the maximum therapy interval has not elapsed, then as represented at line 1328 and block 1330 a query is posed as to whether all implants have been de-energized. Where all implants have not been de-energized, then the program loops as represented by loop line 1332 extending to line 1316. In the event of an affirmative determination that all implants have been de-energized, then as represented at line 1334 and block 1336 the procedure is terminated and light emitting diode 1200 is energized. The procedure then continues as represented at line 1338 and block 1340 wherein if imaging data of the indicia pattern has been produced, then that data is submitted to memory. Next, as represented at line 1342 and block 1344, the implants are removed and, as represented at line 1346 and block 1348 a post therapy review of the patient for the development of neocollagenisis is carried out.

Figure 70:
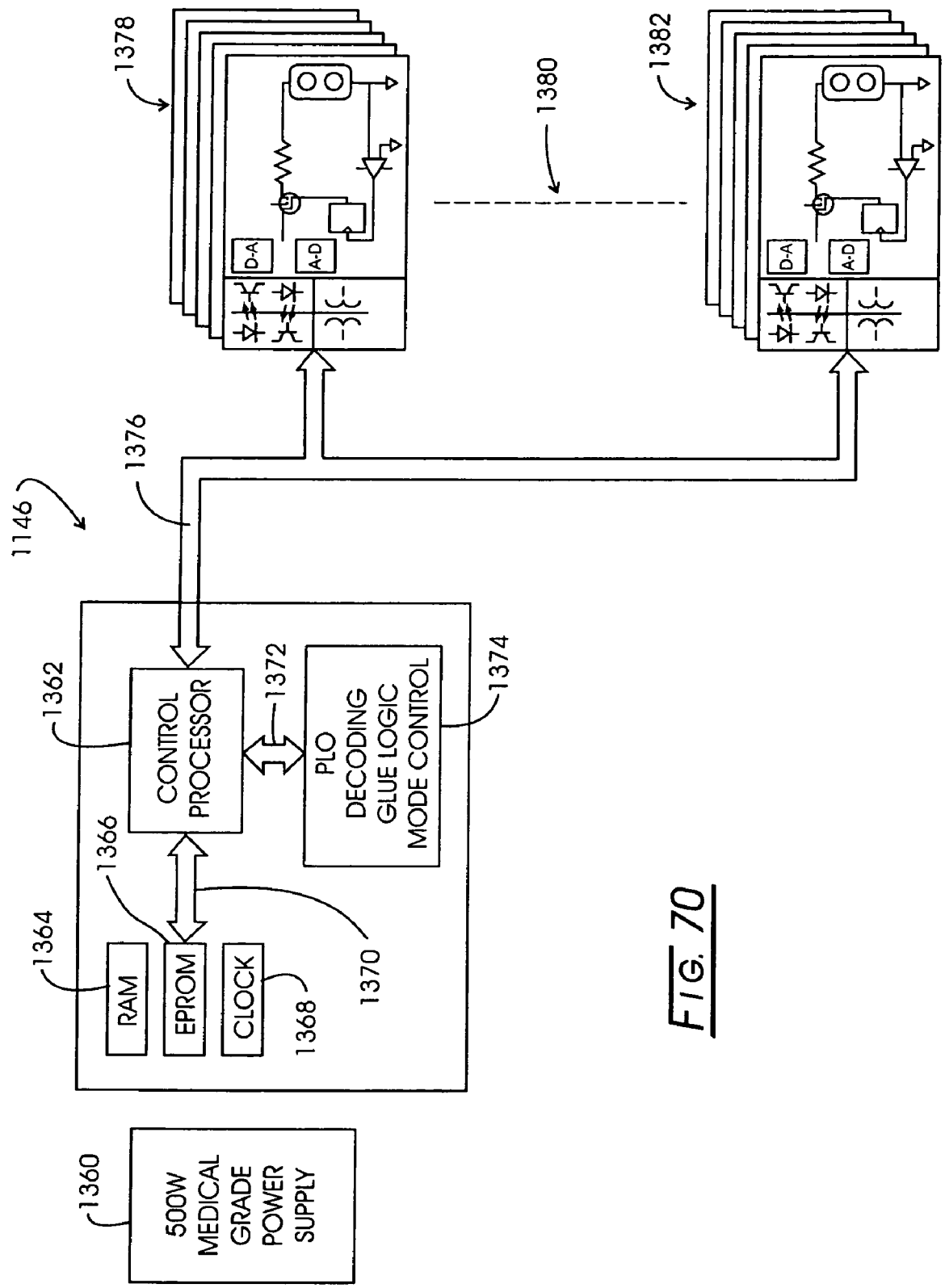
FIG. 70 is a schematic block diagram of a heater controller according to the invention.

Referring to FIG. 70, a schematic representation of the functional features of controller 1146 is presented. The controller performs in conjunction with a 500 watt medical-grade power supply represented at block 1360. Component 1360 performs in conjunction with a control processor 1362. Processor 1362, in conventional manner interactively performs with random access memory (RAM) 1364; erasable programmable read-only memory (EPROM) 1366; and a clock 1368. The noted interaction is represented by dual arrow 1370. Also in conventional fashion, the processor 1362 performs, as represented by dual arrow 1372 with the functions of block 1374 which include a programmable logic device (PLD); decoding; glue logic; and load control. Photo-isolated interactive functioning with each of the heater segments is represented by bus arrow 1376. In this regard, bus 1376 is seen directed to five heater segment control cards represented generally at 1378 which represent segments 1-5 of a heater channel one. As represented by dashed line 1380, ten such sets of control circuit cards are provided in the controller 1146, the tenth set being represented generally at 1382. As represented on the cards, digital heating data is received and converted to an analog signal format for carrying out both the energizaton of the heater elements and resistance measurement. The latter measurements are returned to the controller 1362 following the digitization of their values.

Figure 71:
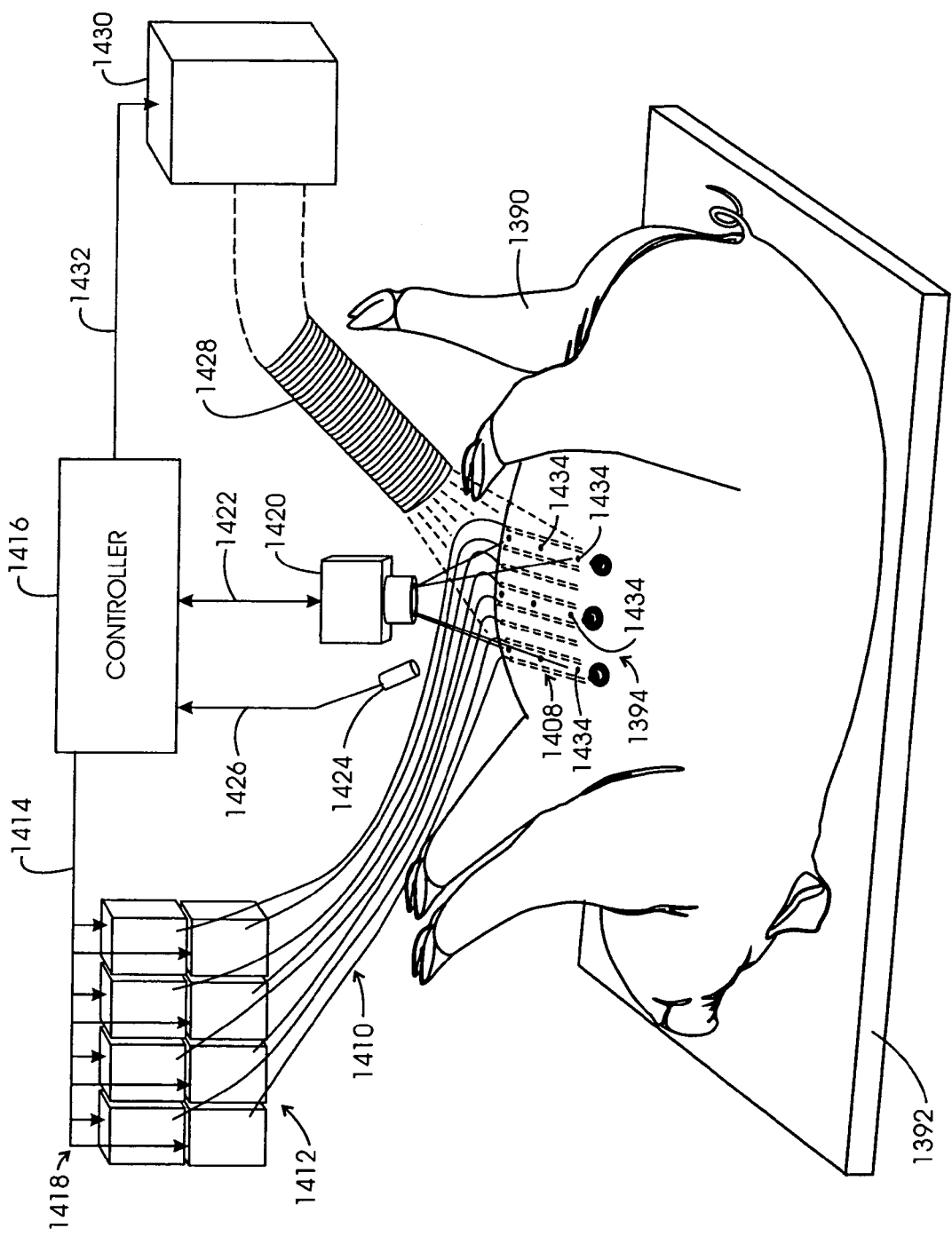
FIG. 71 is a schematic representation of a porcine study of the system of the invention.
Figure 72:
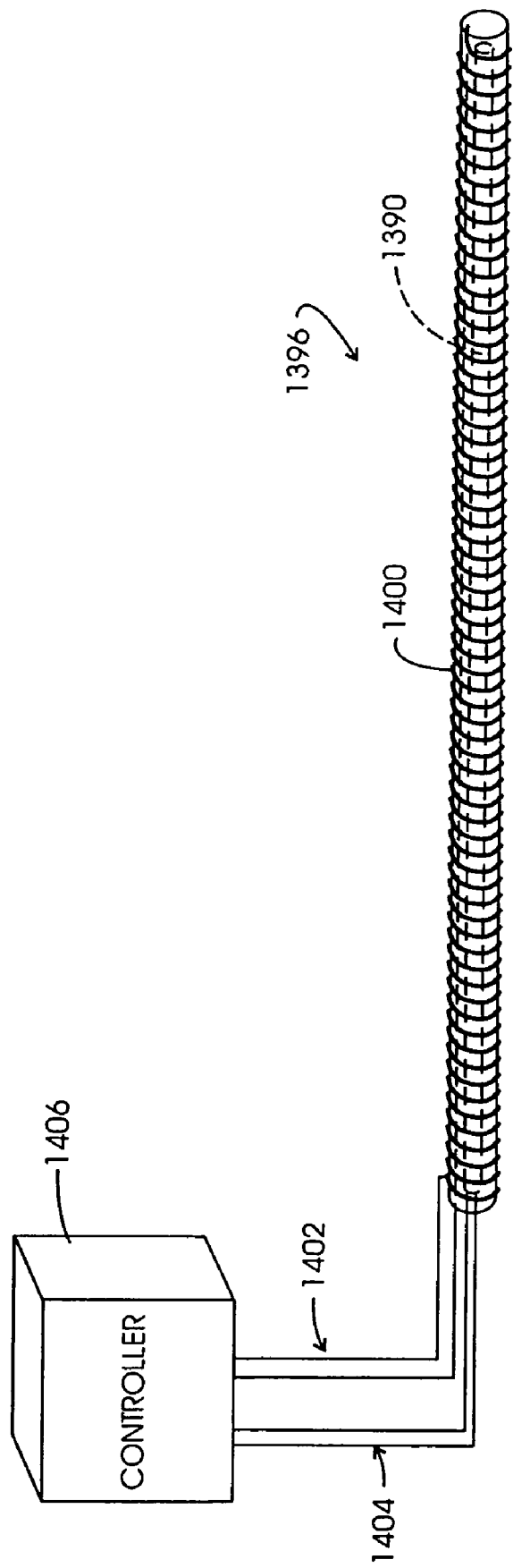
FIG. 72 is a perspective view of an RTD sensor/heater employed with the studies associated with FIG. 71.

In the course of development of the instant system, animal (pig) studies were carried out to evaluate the shrinkage of collagen within the dermis under conditions of heater contact as opposed to energy being introduced, for instance through the epidermis. Referring to FIG. 71, a porcine skin heating procedure is schematically portrayed. Here, the anesthetized animal 1390 is supported upon a surgical table 1392. A region of the skin was selected for the experiment here represented generally at 1394. Eight RTD heaters/sensors were implanted within the dermis in this region with an inter-heater spacing of 4 mm. Looking additionally to FIG. 72, an RTD (resistance-temperature-detector) heater/sensor is represented generally at 1396. Device 1396 is comprised of a platinum resistance element 1398 wrapped with a 0.003 inch diameter heating wire 1400. The device has a length of 25 mm and wire lead pairs carrying heater current and returning temperature data are shown at 1402 and 1404 extending to a controller 1406.

Returning to FIG. 71, eight of such RTD heater/sensors have been implanted in porcine dermis. The devices generally are in parallel with the above-noted widthwise spacing. The eight implants are represented in phantom in general at 1408. Lead pairs extending from these implants 1408 are represented schematically and in general at 1410 extending to eight controller units represented in general at 1412. Control over the controllers 1412 is represented at line 1414 extending from block 1416 to an arrow array represented generally at 1418. A digital microscope 1420 is shown controlled by controller 1416 as represented by dual arrow 1422. The temperature at the surface of region 1394 was monitored by an infrared temperature sensor 1424 shown operationally associated with controller 1460 by arrow 1426. Cooling air was directed to the region 1394 via conduit 1428 which receives air under pressure from blower 1430. Control over the blower 1430 is represented at arrow 1432 extending from controller 1416. Seen at region 1394 are visible and imageable indicia arranged as a pattern of tattoo formed dots, certain of which are represented at 1434. These dots were initially imaged by device 1420 and such imaging continued during the dermis heating procedure.

Figure 73:
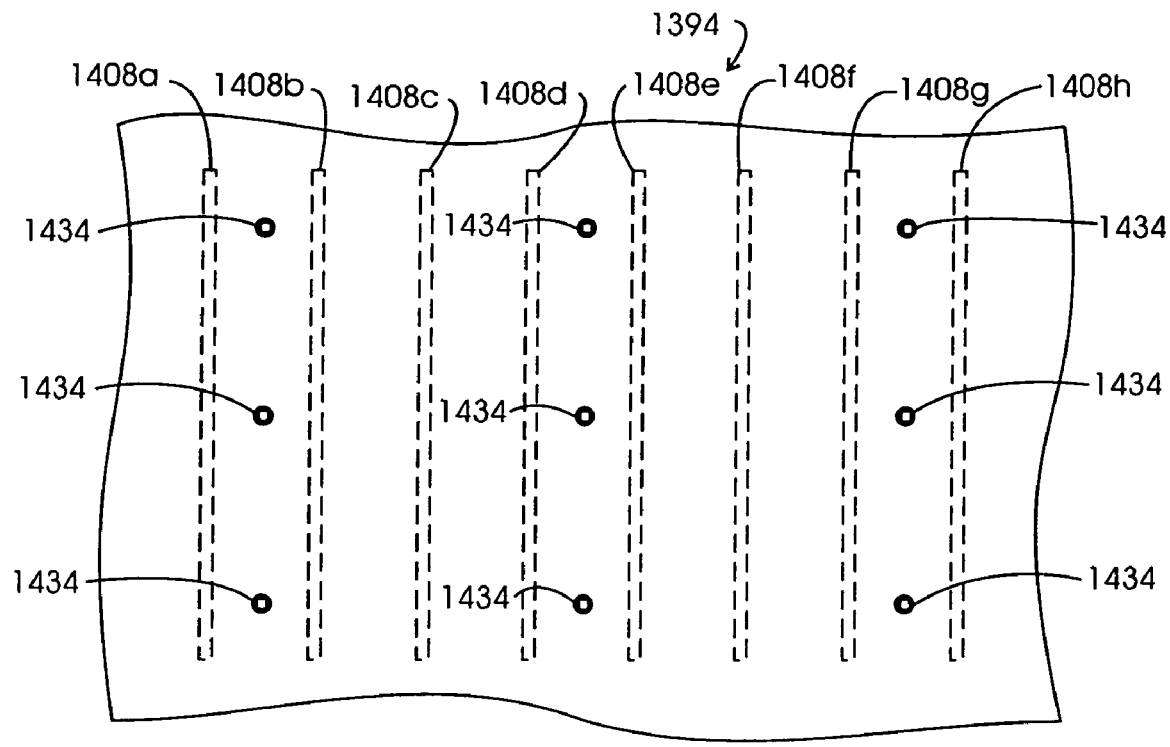
FIG. 73 is an enlarged schematic view of a skin region shown in FIG. 71.
Figure 74:
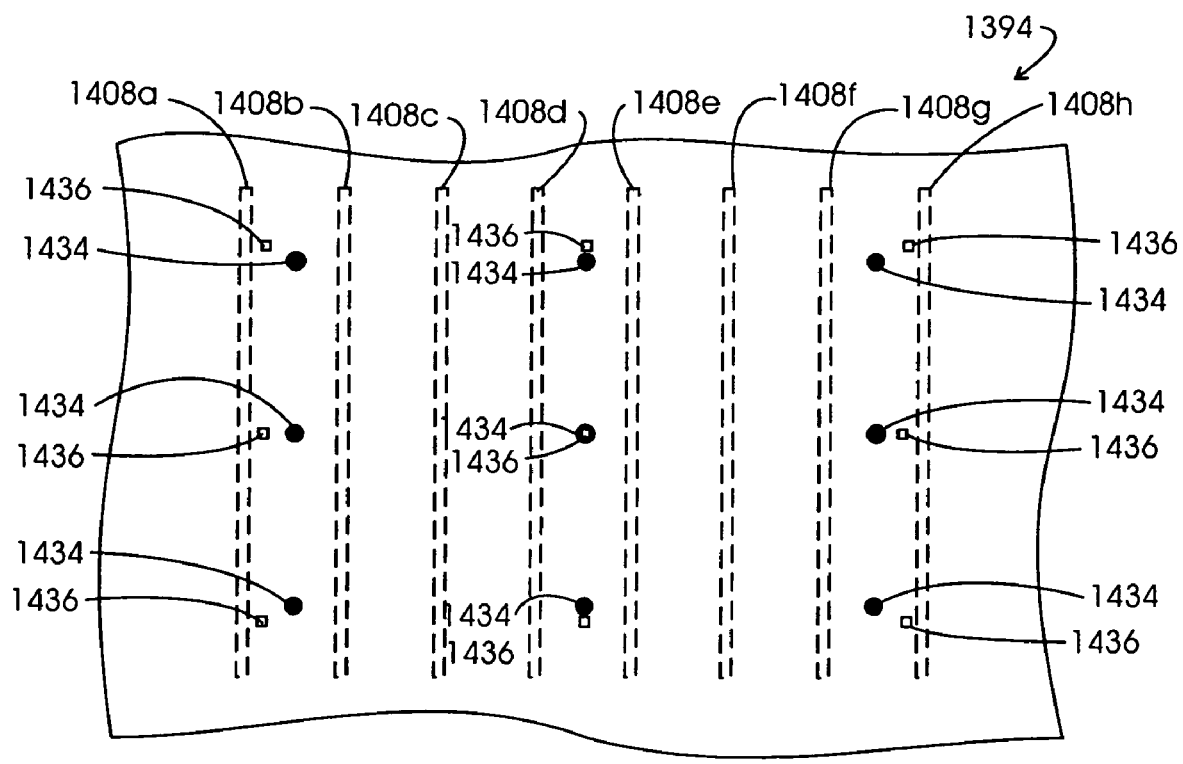
FIG. 74 is a schematic representation showing indicia migration occurring with shrinkage of dermis.

Referring to FIG. 73, the initial positions of the tattoo marks 1434 are shown in conjunction with RTD heater/sensor implant positions 1408*a*-1408*h*. Digital imaging device 1420 superimposed a small square indicia image over each of these tattoo marks. The tattoo marks were spaced apart in columnar fashion a distance of about 1 cm and in row fashion a distance of about 1 cm. Heater and sensor components 1408*a*-1408*h* were elevated in temperature to 75° C. Looking to FIG. 74, the movement of the tattoo indicia 1434 is illustrated following five minutes at the noted heating temperature. The digitally imaged and stationary white squares are seen at 1436. Relative movement of the indicia indicates a shrinkage of the dermis of about 20%. Later in-vivo larger animal experiments demonstrated average linear contraction levels of 10% to 16% and maximum levels up to 22% utilizing heating elements of round cross-section. Where flat heating elements employed with implants similar to that of 920 shown in FIG. 45 were employed an average linear contraction level of 18% was observed with a maximum level up to 21%. The maximum temperature in the subcutaneous fat layer was measured as less than 47° C. utilizing a flat heater design.

Since certain changes may be made in the above-described system, apparatus and method without departing from the scope of the invention herein involved, it is intended that all matter contained in the above description or shown in the accompanying drawings shall be interpreted as illustrative and not in a limiting sense.

We claim:

1. The method for effecting a controlled shrinkage of collagen within the dermis of skin comprising the steps:

(a) determining a skin region for shrinkage;

(b) providing one or more heater implants controllable to provide a heating output and dimensioned for location at dermis substantially only between epidermis and subcutaneous tissue;

(c) determining the extent of collagen shrinkage to be effected at said skin region;

(d) determining one or more heating channel locations along said skin region;

(e) determining a target temperature to be developed within the dermis at said heating channels to achieve said extent of collagen shrinkage with a developed collagen matrix having tensile strength integrity effective to support neocollagenisis;

(f) locating said one or more heater implants in thermal treatment relationship with dermis along said one or more heating channel locations;

(g) controllably effecting a heating of said one or more heater implants to said target temperature or temperatures; and (h) monitoring the extent of collagen shrinkage.

2. The method of claim 1 in which:

said step (b) provides said heater implant with one or more temperature sensible attributes having a temperature monitoring output; and said step (g) controllably effects said heating in correspondence with said monitoring output.

3. The method of claim 2 in which:

said step (b) provides said heater implant as one or more auto-regulating implant components, each comprising a non-magnetic metal sheathed ferrite material core exhibiting a Curie transition temperature substantially corresponding with said target temperature; and said step (g) effects the heating of said heater implant by the extra body application of an alternating current derived electromagnetic field.

4. The method of claim 3 in which:

said step (b) provides said heater implant as a generally flexible assemblage of interconnected and spaced apart auto-regulating implant components, one or more of which is configured with a tissue engaging barbed non-magnetic metal sheath.

5. The method of claim 3 in which:

said step (b) provides said heater implant with one or more passive resonant implants having an electromagnetic response to an extra body applied excitation electromagnetic field, said response exhibiting a predetermined resonant center frequency when said implant is at a monitor temperature or temperatures below a said target temperature; and said step (g) intermittently applies said electromagnetic field in correspondence with said electromagnet response.

6. The method of claim 3 in which:

said step (b) provides said heater implant as a generally flexible assemblage of interconnected and spaced apart auto-regulating implant components.

7. The method of claim 6 in which:

said step (b) provides said heater implant as a string-like assemblage wherein said spaced apart auto-regulating implant components are interconnected by spring-like helical configurations formed of a non-magnetic metal.

8. The method of claim 6 in which:

said step (b) provides said heater implant as a string-like assemblage wherein said spaced apart auto-regulating implant components are interconnected with one or more temperature sensors.

9. The method of claim 8 in which:

said step (b) provides said one or more temperature sensors as a resonant sensor having an electromagnetic response to an extra-body applied excitation electromagnetic field, said response exhibiting a predetermined resonant center frequency in the presence of a monitor temperature below a said target temperature or temperatures; and said step (g) intermittently applies said electromagnetic field in correspondence with said electromagnetic response.

10. The method of claim 3 in which:
said step (b) provides said heater implant as having one or more auto-regulating implant components mounted in mutually flexure promoting spaced relationship upon a surface of a flat polymeric thermal barrier; and
said step (f) locates the one or more heater implants generally at the junction between the dermis and next adjacent subcutaneous tissue.

11. The method of claim 3 in which:
said step (b) provides a said heater implant as an assemblage of two or more ferrite material cores flexibly interconnected in spaced apart relationship by a polymeric shrink wrap, each wrapped core being surmounted by a non-magnetic metal sheath.

12. The method of claim 1 in which:
said step (b) provides a said heater implant as one or more temperature elevating components supported upon a surface of a flexible thin flat thermal barrier.

13. The method of claim 12 in which:
said step (f) locates the one or more heater implants generally at the juncture between the dermis and next adjacent subcutaneous tissue.

14. The method of claim 1 in which:
said step (b) provides a heater implant comprising a flexible polymeric carrier supporting an electrical resistance heater extending from a terminal assembly; and
said step (g) effects the controllable electrical energization of said resistance heater from said terminal assembly.

15. The method of claim 1 in which:
said step (b) provides a heater implant comprising a flexible fluid conduit having an entrance port and an exit port and
said step (g) effects said heating by the delivery of heated fluid between said entrance port and exit port.

16. The method of claim 1 in which:
said step (b) provides a heater implant comprising an auto-regulating ferromagnetic alloy having an electrical input assembly and auto-regulating with respect to a said target temperature; and
said step (g) effects said heating by the application of high frequency current to said electrical input assembly.

17. The method of claim 1 in which:
said step (b) provides a heater implant comprising a wire electrode responsive to a radiofrequency power input to evoke electrosurgical heating; and
said step (g) effects said heating by the application of radiofrequency current to said input in conjunction with a remote return electrode.

18. The method of claim 1 in which:
said step (b) provides a heater implant comprising two or more electrodes responsive to a bipolar power input to evoke electrosurgical heating; and
said step (g) effects said heating by the application of radiofrequency current and voltage across said electrodes.

19. The method of claim 1 in which:
said step (b) provides a heater implant comprising a thermally and electrically insulative flat support having a support surface of given lengthwise dimension said support extending between leading and trailing ends, one or more resistance heater segments mounted upon said support surface spaced inwardly from said trailing end, and an electrical lead assemblage extending from connection with each said segment to terminals adjacent said trailing end;
said step (f) is carried out by tethering the support leading end to a channel forming introducer needle inserted along a heating channel location and drawing the heater implant into position with the support surface outwardly facing; and
said step (g) is carried out by applying electrical energy to each resistive heater segment effective to derive a said target temperature.

20. The method of claim 19 in which:
said step (f) locates the heater implant generally at the junction between the dermis and next adjacent subcutaneous tissue.

21. The method of claim 1 in which:
said step (b) provides a heater implant comprising a thermally insulative flat support having a support surface, said support having a given lengthwise dimension extending between leading and trailing ends, one or more mutually spaced apart heater segments each comprising a non-magnetic metal sheathed ferrite material core exhibiting a Curie transition temperature substantially corresponding with said target temperature mounted upon said support surface;
said step (f) is carried out by tethering the support leading end to a channel forming introducer needle inserted along a heating channel location and drawing the heater implant into position with the support surface outwardly facing; and
said step (g) effects the heating of each heater segment by the extra-body application of an alternating current derived electromagnetic field.

22. The method of claim 21 in which:
said step (f) locates the heater implant between the dermis and next adjacent subcutaneous tissue.

23. The method of claim 1 in which:
said step (b) provides a heater implant comprising a thermally and electrically insulative polymeric substrate with a support surface supporting one or more electrical resistance heater segments extending from a terminal assembly and having a bonding surface opposite said support surface and a flexible polymeric thermal barrier support having a surface bonded with said bonding surface; and
said step (g) effects the controllable electrical energization of said one or more heater segments.

24. The method for effecting a controlled shrinkage of collagen within the dermis of skin, comprising the steps:
(a) determining a skin region for shrinkage;
(b) providing one or more heater implants each comprising a thermally insulative flat support having a lengthwise dimension extending between leading and trailing ends and a widthwise dimension, having a support surface supporting one or more electrically energizable heater segments each controllable to provide a heating output;
(c) determining the extent of collagen shrinkage to be effected at said skin region;
(d) determining one or more heating channel locations along said skin region;
(e) determining a target temperature for each said heating output and the corresponding anticipated interval of treatment at said heating channel locations to achieve said extent of collagen shrinkage;
(f) locating each heater implant along a heating channel generally at the interface between dermis and next adjacent subcutaneous tissue in an orientation wherein said heater segments are in thermal exchange relationship with dermis and thermal insulative relationship with said next adjacent subcutaneous tissue; and
(g) effecting an energization of said one or more heater segments substantially to said target temperature.

25. The method of claim 24 further comprising the step:
(h) monitoring the extent of collagen shrinkage.

26. The method of claim 24 in which:
said step (e) determines said target temperature and corresponding interval of treatment to achieve said extent of collagen shrinkage with a developed collagen matrix having tensile strength integrity effective to support neocollagenisis.

27. The method of claim 25 in which:
said step (a) further comprises the step: providing a pattern of visible indicia at said skin region; and
said step (h) monitors the relative movement of the indicia from said initial locations in consequence of said step (g) to evaluate the extent of collagen shrinkage.

28. The method of claim 27 in which:
said step (h) is carried out by digitally imaging said visible indicia.

29. The method of claim 24 in which:
said step (g) further comprises the step of directing a flow of cooling fluid against the surface of skin at said skin region.

30. The method of claim 29 in which:
said step (g) directs said flow of cooling fluid as a combination of gas and liquid.

31. The method of claim 30 in which:
said step (g) directed liquid is water.

32. The method of claim 30 in which:
said step (g) directed gas is air.

33. The method of claim 24 in which:
said step (g) further comprises the steps:
(g1) determining a maximum value for temperature at the surface of skin within said skin region,
(g2) monitoring the temperature at the surface of the skin within said skin region, and
(g3) deriving a perceptible warning cue when the monitored temperature at the skin region exceeds said maximum value.

34. The method of claim 33 in which:
said step (g) further comprises the step (g4) directing a flow of cooling fluid against the surface of skin at said skin region.

35. The method of claim 24 further comprising the step:
(i) removing said one or more implants subsequent to step (g).

36. The method of claim 35 in which:
said step (g) derives said target temperature while monitoring the temperature of at least a portion of said determined skin region to ascertain the attainment of said target temperature.

37. The method of claim 24 in which:
said step (f) is carried out by forming a said heating channel with an introducer needle having a cutting width corresponding with said flat support widthwise dimension, said channel extending from a skin entrance generally at the junction between dermis and next adjacent subcutaneous tissue, then inserting said support leading end through said skin entrance to effect said heater implant location.

38. The method of claim 37 in which:
said step (b) provides said one or more heater implants comprising a thermally insulative flat support having a said support surface and an oppositely disposed thermally insulative surface, said leading end being tapered from said thermally insulative surface towards said support surface effective to mechanically bias said support surface toward said dermis during said step (f).

39. The method of claim 37 in which:
said step (b) provides said one or more heater implants comprising a said insulative flat support which is structurally rigid in compression to an extent effective to enter a skin entrance incision and move under compressive urging to be located within said heating channel.

40. The method of claim 37 in which:
said step (g) includes the step of removing said one or more heater implants through said skin entrance subsequent to said energization of said one or more heater segments.

41. The method of claim 24 in which:
said step (b) provides said one or more heater implants comprising a said insulative flat support with a bladed leading end, and structurally rigid in compression to an extent effective to enter a skin entrance incision and guidably move under compressive urging along said interface between dermis and next adjacent subcutaneous tissue to form and be located within said heating channel.

42. The method of claim 41 in which:
said step (g) includes the step of removing said one or more heater implants through said skin entrance subsequent to said energization of said one or more heater segments.

43. The method of claim 24 in which:
said step (f) is carried out by tethering the leading end of said flat support to an introducer needle having a cutting width corresponding with said widthwise dimension, then forming a said heating channel with said introducer needle between skin entrance and exit locations and drawing the support into the formed heating channel from the tether.

44. The method of claim 43 in which:
said step (b) provides said support leading end as having a bladed configuration.

45. The method of claim 43 in which:
said step (b) provides a heater implant wherein each said heater segment is a resistance heater segment coupled with a segment electrical lead assemblage extending toward said trailing end; and
said step (g) applies electrical energy to said segment lead assemblage to derive said target temperature.

46. The method of claim 45 in which:
said step (g) derives said target temperature while monitoring the temperature of each said resistance heater segment.

47. The method of claim 46 in which:
said step (g) determines the target resistance value exhibited by each said resistance heater segment when at said target temperature, intermittently determines a monitor value of resistance for each resistance heater segment and applies said electrical energy to each said resistance heater segment in correspondence with said target resistance value and monitor value of resistance.

48. The method of claim 47 in which:
said step (g) determines the target resistance value exhibited by each said resistance heater segment when at said target temperature, determines a monitor value of resistance for each resistance heater segment and applies said electrical energy to each said resistance heater segment in correspondence with said target resistance value and monitor value of resistance.

49. The method of claim 46 in which:
said step (b) provides a heater implant having a temperature sensor mounted at said support surface adjacent each said heater segment electrically coupled with a sensor lead assemblage extending toward said trailing end and providing a monitor temperature signal; and said step (g) applies said electrical energy to each said heater segment in correspondence with said target temperature and each said monitor temperature signal.

50. The method of claim 46 in which:

said step (b) provides said heater implant as further comprising an electrically insulative biocompatible layer disposed over said resistance heater segments and at least those portions of said segment lead assemblage contactable with tissue.

* * * * *